US007056518B2

(12) United States Patent
Druilhe et al.

(10) Patent No.: US 7,056,518 B2
(45) Date of Patent: Jun. 6, 2006

(54) MALARIAL PRE-ERYTHROCYTIC STAGE POLYPEPTIDE MOLECULES

(75) Inventors: Pierre Druilhe, Paris (FR); Pierre Daubersies, Paris (FR)

(73) Assignee: Institut Pasteur, Paris (FR)

( * ) Notice: Subject to any disclaimer, the term of this patent is extended or adjusted under 35 U.S.C. 154(b) by 676 days.

(21) Appl. No.: 09/742,096

(22) Filed: Dec. 22, 2000

(65) Prior Publication Data

US 2002/0155441 A1    Oct. 24, 2002

Related U.S. Application Data

(62) Division of application No. 08/973,462, filed as application No. PCT/FR96/00894 on Jun. 12, 1996, now Pat. No. 6,191,270.

(30) Foreign Application Priority Data

Jun. 13, 1995    (FR) .................................. 95/07007

(51) Int. Cl.
*A61K 39/015* (2006.01)
*C07K 14/445* (2006.01)
*C01N 33/569* (2006.01)

(52) U.S. Cl. ............... 424/191.1; 424/268.1; 424/272.1; 435/7.22; 530/350; 530/395; 530/822

(58) Field of Classification Search ............ 424/185.1, 424/191.1, 268.1, 272.1; 435/7.22; 436/518, 436/523, 531, 534; 514/8; 530/324, 326, 530/328, 350, 395, 822

See application file for complete search history.

(56) References Cited

U.S. PATENT DOCUMENTS 6,191,270 B1 *    2/2001    Druilhe et al. ............. 536/23.7

FOREIGN PATENT DOCUMENTS

FR    2679909    2/1993

(Continued)

OTHER PUBLICATIONS

David A. Fidock, et al., *Cloning and Characterization of a Novel Plasmodium Falciparum Sporozoite Surface Antigen, Starp, Molecular and Biochemical Parasitology*, 64, pp. 212-232, 1994.

(Continued)

*Primary Examiner*—Long V. Le
*Assistant Examiner*—James L. Grun
(74) *Attorney, Agent, or Firm*—Oblon, Spivak, McClelland, Maier & Neustadt, P.C.

(57) ABSTRACT

Polypeptide molecules containing at least 10 consecutive amino acids of the amino acid sequence shown in FIG. 2, representing the LSA3 antigen, the following peptides being excluded:

RDELFNELLNSVDVNGEVKENILEESQVNDDIFNSLVKSVQQEQQHNVEE

VEESVEENDEESVEENVEENVENNDDGSVASSVEESIASSVDESIDSSIE-

ENVAPTVEEIVAPTVEEIVAPSVVEKCAPSVEESVAPSVEESVAEMLKER (729S)

RDELFNELLNSVDVNGEVKENILEESQVNDDIFNSLVKSVQQEQQHN

DELFNELLNSVDVNGEVKENILEESQ, (NRI)

LEESQVNDDIFSNSLVKSVQQEQQHNV, (NRII)

VESVAPSVEESVAPSVEESVAENVESSV. (729RE)

2 Claims, 30 Drawing Sheets

U.S. PATENT DOCUMENTS 6,270,771 B1 * 8/2001 Guerin-Marchand et al. ....... 424/191.1
6,319,502 B1 * 11/2001 Guerin-Marchand et al. ....... 424/191.1

FOREIGN PATENT DOCUMENTS

| WO | 92/13884 | 8/1992 |
| WO | 94/09140 | 4/1994 |
| WO | 96/41877 | 12/1996 |

OTHER PUBLICATIONS

Debra A. Barnes, et al., *Plasmodium Falciparum: D260. An Intraerythrocytic Parasite Protein, is a Member of the Glutamic Acid Dipeptide-Repeat Family of Proteins*, Experimental Parasitology, 81, pp. 79-89, 1995.

* cited by examiner

```
ATTTATTTAT TTTTATTGTT TTATTTCTTT TTTTTCTTTA AATTGTATAT TTATAAATAT    60

TTTAAAAAGT TAGAAAATGA CAAATAGTAA TTACAAATCA AATAATAAAA CATATAATGA   120

AAATAATAAT GAAGAAATAA CTACCATATT TAATAGAACA AATATGAATC CGATAAAAAA   180

ATGTCATATG AGAGAAAAAA TAAATAAGTA CTTTTTTTTG ATCAAAATTT TGACATGCAC   240

CATTTTAATA TGGGCTGTAC AATATGATAA TAACGTAAGA TAAAAAACTA AATAATAAAT   300

ATAAATAAAA AAAAAAAAAA AAAAAAAAAA ATCAACTATA TAGTATGTAT AATATATATA   360

TATATATATA TATATATATA TATATATATA TATTTATTTT TATTTATTTA TTAATTTTTT   420

TTTTTTTATA TTATCTTTTT AGTCTGATAT AAACAAGAGT TGGAAAAAAA ATACGTATGT   480

AGATAAGAAA TTGAATAAAC TATTTAACAG AAGTTTAGGA GAATCTCAAG TAAATGGTGA   540

ATTAGCTAGT GAAGAAGTAA AGGAAAAAAT TCTTGACTTA TTAGAAGAAG GAAATACATT   600

AACTGAAAGT GTAGATGATA ATAAAAATTT AGAAGAAGCC GAAGATATAA AGGAAAATAT   660

CTTATTAAGT AATATAGAAG AACCAAAAGA AAATATTATT GACAATTTAT TAAATAATAT   720

TGGACAAAAT TCAGAAAAAC AAGAAAGTGT ATCAGAAAAT GTACAAGTCA GTGATGAACT   780

TTTTAATGAA TTATTAAATA GTGTAGATGT TAATGGAGAA GTAAAAGAAA ATATTTTGGA   840

GGAAAGTCAA GTTAATGACG ATATTTTTAA TAGTTTAGTA AAAAGTGTTC AACAAGAACA   900

ACAACACAAT GTTGAAGAAA AAGTTGAAGA AAGTGTAGAA GAAAATGACG AAGAAAGTGT   960

AGAAGAAAAT GTAGAAGAAA ATGTAGAAGA AAATGACGAC GGAAGTGTAG CCTCAAGTGT  1020

TGAAGAAAGT ATAGCTTCAA GTGTTGATGA AGTATAGAT TCAAGTATTG AAGAAAATGT  1089

AGCTCCAACT GTTGAAGAAA TCGTAGCTCC AAGTGTTGTA GAAACTGTGG CTCCAAGTGT  1140

TGAAGAAAGT GTAGAAGAAA ATGTTGAAGA AAGTGTAGCT GAAAATGTTG AAGAAAGTGT  1200
```

*FIG. 1a*

```
AGCTGAAAAT GTTGAAGAAA GTGTAGCTGA AAATGTTGAA GAAAGTGTAG CTGAAAATGT  1260

TGAAGAAATC GTAGCTCCAA CTGTTGAAGA AATCGTAGCT CGAACTGTTG AAGAAATTGT  1320

AGCTCCAAGT GTTGTAGAAA GTGTGGCTCC AAGTGTTGAA GAAAGTGTAG AAGAAAATGT  1380

TGAAGAAAGT GTAGCTGAAA ATGTTGAAGA AAGTGTAGCT GAAAATGTTG AAGAAAGTGT  1440

AGCTGAAAAT GTTGAAGAAA GTGTAGCTGA AAATGTTGAA GAAAGTGTAG CTGAAAATGT  1500

TGAAGAAATC GTAGCTCCAA CTGTTGAAGA AATCGTAGCT CCAACTGTTG AAGAAATTGT  1560

AGCTCCAAGT GTTGTAGAAA GTGTGGCTCC AAGTGTTGAA GAAAGTGTAG AAGAAAATGT  1620

TGAAGAAAGT GTAGCTGAAA ATGTTGAAGA AAGTGTAGCT GAAAATGTTG AAGAAAGTGT  1680

AGCTGAAAAT GTTGAAGAAA GTGTAGCTGA AAATGTTGAA GAAAGTGTAG CTGAAAATGT  1740

TGAAGAAAGT GTAGCTGAAA ATGTTGAAGA AAGTGTAGCT GAAAATGTTG AAGAAATCGT  1800

AGCTCCAACT GTTGAAGAAA TCGTAGCTCC AACTGTTGAA GAAATTGTAG CTCCAAGTGT  1860

TGTAGAAAGT GTGGCTCCAA GTGTTGAAGA AAGTGTAGAA GAAAATGTTG AAGAAAGTGT  1920

AGCTGAAAAT GTTGAAGAAA GTGTAGCTGA AAATGTTGAA GAAAGTGTAG CTGAAAATGT  1980

TGAAGAAAGT GTAGCTGAAA ATGTTGAAGA AATCGTAGCT CCAACTGTTG AAGAAATCGT  2040

AGCTCCAACT GTTGAAGAAA TTGTAGCTCC AAGTGTTGTA GAAAGTGTGG CTCCAAGTGT  2100

TGAAGAAAGT GTAGAAGAAA ATGTTGAAGA AAGTGTAGCT GAAAATGTTG AAGAAAGTGT  2160

AGCTGAAAAT GTTGAAGAAA GTGTAGCTGA AAATGTTGAA GAAATCGTAG CTCCAACTGT  2220

TGAAGAAATC GTAGCTCCAA CTGTTGAAGA AATTGTAGCT CCAAGTGTTG TAGAAAGTGT  2280

GGCTCCAAGT GTTGAAGAAA GTGTAGAAGA AAATGTTGAA GAAAGTGTAG CTGAAAATGT  2340

TGAAGAAAGT GTAGCTGAAA ATGTTGAAGA AAGTGTAGCT GAAAATGTTG AAGAAAGTGT  2400
```

*FIG. 1b*

```
AGCTGAAAAT GTTGAAGAAA TCGTAGCTCC AACTGTTGAA GAAATCGTAG CTCCAACTGT   2460

TGAAGAAATT GTAGCTCCAA GTGTTGTAGA AAGTGTGGCT CCAAGTGTTG AAGAAAGTGT   2520

AGAAGAAAAT GTTGAAGAAA GTGTAGCTGA AAATGTTGAA GAAAGTGTAG CTGAAAATGT   2580

TGAAGAAAGT GTAGCTGAAA ATGTTGAAGA AAGTGTAGCT GCAACTGTTG AAGAAATTGT   2640

AGCTCCAAGT GTTGAAGAAA GTGTAGCTCC AAGTGTTGAA GAAAGTGTTG CTGAAAACGT   2700

TGCAACAAAT TTATCAGACA ATCTTTTAAG TAATTTATTA GGTGGTATCG AAACTGAGGA   2760

AATAAAGGAC AGTATATTAA ATGAGATAGA AGAAGTAAAA GAAAATGTAG TCACCAGAAT   2820

ACTAGAAAAC GTAGAAGAAA CTACAGCTGA AAGTGTAACT ACTTTTAGTA ACATATTAGA   2880

GGAGATACAA GAAAATACTA TTACTAATGA TACTATAGAG GAAAAATTAG AAGAACTCCA   2940

CGAAAATGTA TTAAGTGCCG CTTTAGAAAA TACCCAAAGT GAAGAGGAAA AGAAAGAAGT   3000

AATAGATGTA ATTGAAGAAG TAAAAGAAGA GGTCGCTACC ACTTTAATAG AAACTGTGGA   3060

ACAGGCAGAA GAAAAGAGCG CAAATACAAT TACGGAAATA TTTGAAAATT TAGAAGAAAA   3120

TGCAGTAGAA AGTAATGAAA ATGTTGCAGA GAATTTAGAG AAAATTAAACG AAACTGTATT   3180

TAATACTGTA TTAGATAAAG TAGAGGAAAC AGTAGAAATT AGCGGAGAAA GTTTAGAAAA   3240

CAATGAAATG GATAAAGCAT TTTTTAGTGA AATATTTGAT AATGTAAAAG GAATACAAGA   3300

AAATTTATTA ACAGGTATGT TTCGAAGTAT AGAAACCAGT ATAGTAATCC AATCAGAAGA   3360

AAAGGTTGAT TTGAATGAAA ATGTGGTTAG TTCGATTTTA GATAATATAG AAAATATGAA   3420

AGAAGGTTTA TTAAATAAAT TAGAAAATAT TTCAAGTACT GAAGGTGTTC AAGAAACTGT   3480

AACTGAACAT GTAGAACAAA ATGTATATGT GGATGTTGAT GTTCCTGCTA TGAAAGATCA   3540

ATTTTTAGGA ATATTAAATG AGGCAGGAGG GTTGAAAGAA ATGTTTTTTA ATTTGGAAGA   3600
```

*FIG. 1c*

```
TGTATTTAAA AGTGAAAGTG ATGTAATTAC TGTAGAAGAA ATTAAGGATG AACCGGTTCA    3660

AAAAGAGGTA GAAAAAGAAA CTGTTAGTAT TATTGAAGAA ATGGAAGAAA ATATTGTAGA    3720

TGTATTAGAG GAAGAAAAAG AAGATTTAAG AGACAAGATG ATAGATGCAG TAGAAGAATC    3780

CATAGAAATA TCTTCAGATT CTAAAGAAGA AACTGAATCT ATTAAAGATA AGAAAAAGA    3840

TGTTTCACTA GTTGTTGAAG AAGTTCAAGA CAATGATATG GATGAAAGTG TTGAGAAAGT    3900

TTTAGAATTG AAAAATATGG AAGAGGAGTT AATGAAGGAT GCTGTTGAAA TAAATGACAT    3960

TACTAGCAAA CTTATTGAAG AAACTCAAGA GTTAAATGAA GTAGAAGCAG ATTTAATAAA    4020

AGATATGGAA AAATTAAAAG AATTAGAAAA AGCATTATCA GAAGATTCTA AAGAAATAAT    4080

AGATGCAAAA GATGATACAT TAGAAAAAGT TATTGAAGAG GAACATGATA TAACGACGAC    4140

GTTGGATGAA GTTGTAGAAT TAAAAGATGT CGAAGAAGAC AAGATCGAAA AAGTATCTGA    4200

TTTAAAAGAT CTTGAAGAAG ATATATTAAA AGAAGTAAAA GAAATCAAAG AACTTGAAAG    4260

TGAAATTTTA GAAGATTATA AGAATTAAAA AACTATTGAA ACAGATATTT TAGAAGAGAA    4320

AAAAGAAATA GAAAAAGATC ATTTTGAAAA ATTCGAAGAA GAAGCTGAAG AAATAAAAGA    4380

TCTTGAAGCA GATATATTAA AGAAGTATC TTCATTAGAA GTTGAAGAAG AAAAAAAATT    4440

AGAAGAAGTA CACGAATTAA AGAAGAGGT AGAACATATA ATAAGTGGTG ATGCGCATAT    4500

AAAAGGTTTG GAAGAAGATG ATTTAGAAGA AGTAGATGAT TTAAAAGGAA GTATATTAGA    4560

CATGTTAAAG GGAGATATGG AATTAGGGGA TATGGATAAG GAAAGTTTAG AAGATGTAAC    4620

AACAAAACTT GGAGAAAGAG TTGAATCCTT AAAAGATGTT TTATCTAGTG CATTAGGCAT    4680

GGATGAAGAA CAAATGAAAA CAAGAAAAAA AGCTCAAAGA CCTAAGTTGG AAGAAGTATT    4740

ATTAAAAGAA GAGGTTAAAG AAGAACCAAA GAAAAAAATA ACAAAAAAGA AAGTAAGGTT    4800
```

*FIG. 1d*

```
TGATATTAAG GATAAGGAAC CAAAAGATGA AATAGTAGAA GTTGAAATGA AAGATGAAGA   4860

TATAGAAGAA GATGTAGAAG AAGATATAGA AGAAGATATA GAAGAAGATA AAGTTGAAGA   4920

TATAGATGAA GATATAGATG AAGATATAGG TGAAGACAAA GATGAAGTTA TAGATTTAAT   4980

AGTCCAAAAA GAGAAACGCA TTGAAAAGGT TAAAGCGAAA AAGAAAAAAT TAGAAAAAAA   5040

AGTTGAAGAA GGTGTTAGTG GTCTTAAAAA ACACGTAGAC GAAGTAATGA AATATGTTCA   5100

AAAAATTGAT AAAGAAGTTG ATAAAGAAGT ATCTAAAGCT TTAGAATCAA AAAATGATGT   5160

TACTAATGTT TTAAAACAAA ATCAAGATTT TTTTAGTAAA GTTAAAAACT TCGTAAAAAA   5220

ATATAAAGTA TTTGCTGCAC CATTCATATC TGCCGTTGCA GCATTTGCAT CATATGTAGT   5280

TGGGTTCTTT ACATTTTCTT TATTTTCATC ATGTGTAACA ATAGCTTCTT CAACTTACTT   5340

ATTATCAAAA GTTGACAAAA CTATAAATAA AAATAAGGAG AGACCGTTTT ATTCATTTGT   5400

ATTTGATATC TTTAAGAATT TAAAACATTA TTTACAACAA ATGAAAGAAA AATTTAGTAA   5460

AGAAAAAAAT AATAATGTAA TAGAAGTAAC AAACAAAGCT GAGAAAAAAG GTAATGTACA   5520

GGTAACAAAT AAAACCGAGA AAACAACTAA AGTTGATAAA AATAATAAAG TACCGAAAAA   5580

AAGAAGAACG CAAAAATCAA AATAAAAAAT TGCAGAAGAG TGAAATGATT GGAGGGAACA   5640

ATAAAATTAA TCGATAAAAA ATATAAAAAT GTATATATTA TGTAAATATA TATAAATAAA   5700

TAAATAAATA CATACATATA TATATATATA TATATGTATC TTTTTACAAA ATTTTAAAAT   5760

TTTAAAATTT ATATATATTA ATATTTATAT TTTTCCATAT ATAATTTTAT TTTCAATATT   5820

TTATTTTTAA TTATAAATGT TTTTTACAGA GTTTATGTTT TTTAATTAAT ATATAGATTT   5880

CTGTAAGAAA CTGTATATTA TTCATACGAT ATATGTAATA TTAATTATTT GTGTTTTATT   5940
```

*FIG. 1e*

```
AAAATTTATA TTATATAATA TATATATATA TATATATGTA TATATATTAG AAGATAAAAA   6000

TTTAGCTTAT TTTGCTTGTT ATGCAAATAA GCTTTTTTTT TTTTTTTTTT TTTTTTTTTC   6060

ATATAAACGA TGTTTAATTT TTAATTTTTA ATATTTTATA TAAAATATTT TTCCTAAAAA   6120

AAAAAAAAAT TAAAAAAAAC TTATATTTCG AA                                6152
```

FIG. 1f

```
ATG ACA AAT AGT AAT TAC AAA TCA AAT AAT AAA ACA TAT AAT GAA AAT      48
Met Thr Asn Ser Asn Tyr Lys Ser Asn Asn Lys Thr Tyr Asn Glu Asn
 1           5                  10                  15

AAT AAT GAA CAA ATA ACT ACC ATA TTT AAT AGA ACA AAT ATG AAT CCG      96
Asn Asn Glu Gln Ile Thr Thr Ile Phe Asn Arg Thr Asn Met Asn Pro
             20                  25                  30

ATA AAA AAA TGT CAT ATG AGA GAA AAA ATA AAT AAG TAC TTT TTT TTG     144
Ile Lys Lys Cys His Met Arg Glu Lys Ile Asn Lys Tyr Phe Phe Leu
         35                  40                  45

ATC AAA ATT TTG ACA TGC ACC ATT TTA ATA TGG GCT GTA CAA TAT GAT     192
Ile Lys Ile Leu Thr Cys Thr Ile Leu Ile Trp Ala Val Gln Tyr Asp
     50                  55                  60

AAT AAC TCT GAT ATA AAC AAG AGT TGG AAA AAA AAT ACG TAT GTA GAT     240
Asn Asn Ser Asp Ile Asn Lys Ser Trp Lys Lys Asn Thr Tyr Val Asp
 65                  70                  75                  80

AAG AAA TTG AAT AAA CTA TTT AAC AGA AGT TTA GGA GAA TCT CAA GTA     288
Lys Lys Leu Asn Lys Leu Phe Asn Arg Ser Leu Gly Glu Ser Gln Val
                 85                  90                  95

AAT GGT GAA TTA GCT AGT GAA GAA GTA AAG GAA AAA ATT CTT GAC TTA     336
Asn Gly Glu Leu Ala Ser Glu Glu Val Lys Glu Lys Ile Leu Asp Leu
             100                 105                 110

TTA GAA GAA GGA AAT ACA TTA ACT GAA AGT GTA GAT GAT AAT AAA AAT     384
Leu Glu Glu Gly Asn Thr Leu Thr Glu Ser Val Asp Asp Asn Lys Asn
         115                 120                 125

TTA GAA GAA GCC GAA GAT ATA AAG GAA AAT ATC TTA TTA AGT AAT ATA     432
Leu Glu Glu Ala Glu Asp Ile Lys Glu Asn Ile Leu Leu Ser Asn Ile
     130                 135                 140

GAA GAA CCA AAA GAA AAT ATT ATT GAC AAT TTA TTA AAT AAT ATT GGA     480
Glu Glu Pro Lys Glu Asn Ile Ile Asp Asn Leu Leu Asn Asn Ile Gly
 145                 150                 155                 160
```

*FIG. 2a*

```
CAA AAT TCA GAA AAA CAA GAA AGT GTA TCA GAA AAT GTA CAA GTC AGT      528
Gln Asn Ser Glu Lys Gln Glu Ser Val Ser Glu Asn Val Gln Val Ser
                165             170             175

GAT GAA CTT TTT AAT GAA TTA TTA AAT AGT GTA GAT GTT AAT GGA GAA      576
Asp Glu Leu Phe Asn Glu Leu Leu Asn Ser Val Asp Val Asn Gly Glu
                180             185             190

GTA AAA GAA AAT ATT TTG GAG GAA AGT CAA GTT AAT GAC GAT ATT TTT      624
Val Lys Glu Asn Ile Leu Glu Glu Ser Gln Val Asn Asp Asp Ile Phe
                195             200             205

AAT AGT TTA GTA AAA AGT GTT CAA CAA GAA CAA CAA CAC AAT GTT GAA      672
Asn Ser Leu Val Lys Ser Val Gln Gln Glu Gln Gln His Asn Val Glu
                210             215             220

GAA AAA GTT GAA GAA AGT GTA GAA GAA AAT GAC GAA GAA AGT GTA GAA      720
Glu Lys Val Glu Glu Ser Val Glu Glu Asn Asp Glu Glu Ser Val Glu
225             230             235             240

GAA AAT GTA GAA GAA AAT GTA GAA GAA AAT GAC GAC GGA AGT GTA GCC      768
Glu Asn Val Glu Glu Asn Val Glu Glu Asn Asp Asp Gly Ser Val Ala
                245             250             255

TCA AGT GTT GAA GAA AGT ATA GCT TCA AGT GTT GAT GAA AGT ATA GAT      816
Ser Ser Val Glu Glu Ser Ile Ala Ser Ser Val Asp Glu Ser Ile Asp
                260             265             270

TCA AGT ATT GAA GAA AAT GTA GCT CCA ACT GTT GAA GAA ATC GTA GCT      864
Ser Ser Ile Glu Glu Asn Val Ala Pro Thr Val Glu Glu Ile Val Ala
                275             280             285

CCA AGT GTT GTA GAA AGT GTG GCT CCA AGT GTT GAA GAA AGT GTA GAA      912
Pro Ser Val Val Glu Ser Val Ala Pro Ser Val Glu Glu Ser Val Glu
                290             295             300

GAA AAT GTT GAA GAA AGT GTA GCT GAA AAT GTT GAA GAA AGT GTA GCT      960
Glu Asn Val Glu Glu Ser Val Ala Glu Asn Val Glu Glu Ser Val Ala
305             310             315             320
```

*FIG. 2b*

```
GAA AAT GTT GAA GAA AGT GTA GCT GAA AAT GTT GAA GAA AGT GTA GCT   1008
Glu Asn Val Glu Glu Ser Val Ala Glu Asn Val Glu Glu Ser Val Ala
            325                 330                 335

GAA AAT GTT GAA GAA ATC CTA GCT CCA ACT GTT GAA GAA ATC GTA GCT   1056
Glu Asn Val Glu Glu Ile Val Ala Pro Thr Val Glu Glu Ile Val Ala
            340                 345                 350

CCA ACT GTT GAA GAA ATT GTA GCT CCA AGT GTT GTA GAA AGT GTG GCT   1104
Pro Thr Val Glu Glu Ile Val Ala Pro Ser Val Val Glu Ser Val Ala
            355                 360                 365

CCA AGT GTT GAA GAA AGT GTA GAA GAA AAT GTT GAA GAA AGT GTA GCT   1152
Pro Ser Val Glu Glu Ser Val Glu Glu Asn Val Glu Glu Ser Val Ala
            370                 375                 380

GAA AAT GTT GAA GAA AGT GTA GCT GAA AAT GTT GAA GAA AGT GTA GCT   1200
Glu Asn Val Glu Glu Ser Val Ala Glu Asn Val Glu Glu Ser Val Ala
385                 390                 395                 400

GAA AAT GTT GAA GAA AGT GTA GCT GAA AAT GTT GAA GAA AGT GTA GCT   1248
Glu Asn Val Glu Glu Ser Val Ala Glu Asn Val Glu Glu Ser Val Ala
            405                 410                 415

GAA AAT GTT GAA GAA ATC GTA GCT CCA ACT GTT GAA GAA ATC GTA GCT   1296
Glu Asn Val Glu Glu Ile Val Ala Pro Thr Val Glu Glu Ile Val Ala
            420                 425                 430

CCA ACT GTT GAA GAA ATT GTA GCT CCA AGT GTT GTA GAA AGT GTG GCT   1344
Pro Thr Val Glu Glu Ile Val Ala Pro Ser Val Val Glu Ser Val Ala
            435                 440                 445

CCA AGT GTT GAA GAA AGT GTA GAA GAA AAT GTT GAA GAA AGT GTA GCT   1392
Pro Ser Val Glu Glu Ser Val Glu Glu Asn Val Glu Glu Ser Val Ala
            450                 455                 460

GAA AAT GTT GAA GAA AGT GTA GCT GAA AAT GTT GAA GAA AGT GTA GCT   1440
Glu Asn Val Glu Glu Ser Val Ala Glu Asn Val Glu Glu Ser Val Ala
465                 470                 475                 480
```

*FIG. 2c*

```
GAA AAT GTT GAA GAA AGT GTA GCT GAA AAT GTT GAA GAA AGT GTA GCT   1488
Glu Asn Val Glu Glu Ser Val Ala Glu Asn Val Glu Glu Ser Val Ala
            485                 490                 495

GAA AAT GTT GAA GAA AGT GTA GCT GAA AAT GTT GAA GAA AGT GTA GCT   1536
Glu Asn Val Glu Glu Ser Val Ala Glu Asn Val Glu Glu Ser Val Ala
            500                 505                 510

GAA AAT GTT GAA GAA ATC GTA GCT CCA ACT GTT GAA GAA ATC GTA GCT   1584
Glu Asn Val Glu Glu Ile Val Ala Pro Thr Val Glu Glu Ile Val Ala
            515                 520                 525

CCA ACT GTT GAA GAA ATT GTA GCT CCA AGT GTT GTA GAA AGT GTG GCT   1632
Pro Thr Val Glu Glu Ile Val Ala Pro Ser Val Val Glu Ser Val Ala
            530                 535                 540

CCA AGT GTT GAA GAA AGT GTA GAA GAA AAT GTT GAA GAA AGT GTA GCT   1680
Pro Ser Val Glu Glu Ser Val Glu Glu Asn Val Glu Glu Ser Val Ala
545                 550                 555                 560

GAA AAT GTT GAA GAA AGT GTA GCT GAA AAT GTT GAA GAA AGT GTA GCT   1728
Glu Asn Val Glu Glu Ser Val Ala Glu Asn Val Glu Glu Ser Val Ala
            565                 570                 575

GAA AAT GTT GAA GAA AGT GTA GCT GAA AAT GTT GAA GAA ATC GTA GCT   1776
Glu Asn Val Glu Glu Ser Val Ala Glu Asn Val Glu Glu Ile Val Ala
            580                 585                 590

CCA ACT GTT GAA GAA ATC GTA GCT CCA ACT GTT GAA GAA ATT GTA GCT   1824
Pro Thr Val Glu Glu Ile Val Ala Pro Thr Val Glu Glu Ile Val Ala
            595                 600                 605

CCA AGT GTT GTA GAA AGT GTG GCT CCA AGT GTT GAA GAA AGT GTA GAA   1872
Pro Ser Val Val Glu Ser Val Ala Pro Ser Val Glu Glu Ser Val Glu
            610                 615                 620

GAA AAT GTT GAA GAA AGT GTA GCT GAA AAT GTT GAA GAA AGT GTA GCT   1920
Glu Asn Val Glu Glu Ser Val Ala Glu Asn Val Glu Glu Ser Val Ala
625                 630                 635                 640
```

*FIG. 2d*

```
GAA AAT GTT GAA GAA AGT GTA GCT GAA AAT GTT GAA GAA ATC GTA GCT   1968
Glu Asn Val Glu Glu Ser Val Ala Glu Asn Val Glu Glu Ile Val Ala
            645                 650                 655

CCA ACT GTT GAA GAA ATC GTA GCT CCA ACT GTT GAA GAA ATT GTA GCT   2016
Pro Thr Val Glu Glu Ile Val Ala Pro Thr Val Glu Glu Ile Val Ala
            660                 665                 670

CCA AGT GTT GTA GAA AGT GTG GCT CCA AGT GTT GAA GAA AGT GTA GAA   2064
Pro Ser Val Val Glu Ser Val Ala Pro Ser Val Glu Glu Ser Val Glu
            675                 680                 685

GAA AAT GTT GAA GAA AGT GTA GCT GAA AAT GTT GAA GAA AGT GTA GCT   2112
Glu Asn Val Glu Glu Ser Val Ala Glu Asn Val Glu Glu Ser Val Ala
        690                 695                 700

GAA AAT GTT GAA GAA AGT GTA GCT GAA AAT GTT GAA GAA AGT GTA GCT   2160
Glu Asn Val Glu Glu Ser Val Ala Glu Asn Val Glu Glu Ser Val Ala
705                 710                 715                 720

GAA AAT GTT GAA GAA ATC GTA GCT CCA ACT GTT GAA GAA ATC GTA GCT   2208
Glu Asn Val Glu Glu Ile Val Ala Pro Thr Val Glu Glu Ile Val Ala
            725                 730                 735

CCA ACT GTT GAA GAA ATT GTA GCT CCA AGT GTT GTA GAA AGT GTG GCT   2256
Pro Thr Val Glu Glu Ile Val Ala Pro Ser Val Val Glu Ser Val Ala
            740                 745                 750

CCA AGT GTT GAA GAA AGT CTA GAA GAA AAT GTT GAA GAA AGT GTA GCT   2304
Pro Ser Val Glu Glu Ser Val Glu Glu Asn Val Glu Glu Ser Val Ala
            755                 760                 765

GAA AAT GTT GAA GAA AGT GTA GCT GAA AAT GTT GAA GAA AGT GTA GCT   2352
Glu Asn Val Glu Glu Ser Val Ala Glu Asn Val Glu Glu Ser Val Ala
        770                 775                 780

GAA AAT GTT GAA GAA AGT GTA GCT CCA ACT GTT GAA GAA ATT GTA GCT   2400
Glu Asn Val Glu Glu Ser Val Ala Pro Thr Val Glu Glu Ile Val Ala
785                 790                 795                 800
```

*FIG. 2e*

```
CCA AGT GTT GAA GAA AGT GTA GCT CCA AGT GTT GAA GAA AGT GTT GCT   2448
Pro Ser Val Glu Glu Ser Val Ala Pro Ser Val Glu Glu Ser Val Ala
            805                 810                 815

GAA AAC GTT GCA ACA AAT TTA TCA GAC AAT CTT TTA AGT AAT TTA TTA   2496
Glu Asn Val Ala Thr Asn Leu Ser Asp Asn Leu Leu Ser Asn Leu Leu
            820                 825                 830

GGT GGT ATC GAA ACT GAG GAA ATA AAG GAC AGT ATA TTA AAT GAG ATA   2544
Gly Gly Ile Glu Thr Glu Glu Ile Lys Asp Ser Ile Leu Asn Glu Ile
            835                 840                 845

GAA GAA GTA AAA GAA AAT GTA GTC ACC ACA ATA CTA GAA AAC GTA GAA   2592
Glu Glu Val Lys Glu Asn Val Val Thr Thr Ile Leu Glu Asn Val Glu
            850                 855                 860

GAA ACT ACA GCT GAA AGT GTA ACT ACT TTT AGT AAC ATA TTA GAG GAG   2640
Glu Thr Thr Ala Glu Ser Val Thr Thr Phe Ser Asn Ile Leu Glu Glu
865                 870                 875                 880

ATA CAA GAA AAT ACT ATT ACT AAT GAT ACT ATA GAG GAA AAA TTA GAA   2688
Ile Gln Glu Asn Thr Ile Thr Asn Asp Thr Ile Glu Glu Lys Leu Glu
            885                 890                 895

GAA CTC CAC GAA AAT GTA TTA AGT GCC GCT TTA GAA AAT AGC CAA AGT   2736
Glu Leu His Glu Asn Val Leu Ser Ala Ala Leu Glu Asn Ser Gln Ser
            900                 905                 910

GAA GAG GAA AAG AAA GAA GTA ATA GAT GTA ATT GAA GAA CTA AAA GAA   2784
Glu Glu Glu Lys Lys Glu Val Ile Asp Val Ile Glu Glu Val Lys Glu
            915                 920                 925

GAG GTC GCT ACC ACT TTA ATA GAA ACT GTG GAA CAG GCA GAA GAA AAG   2832
Glu Val Ala Thr Thr Leu Ile Glu Thr Val Glu Gln Ala Glu Glu Lys
            930                 935                 940

AGC GCA AAT ACA ATT ACG GAA ATA TTT GAA AAT TTA GAA GAA AAT GCA   2880
Ser Ala Asn Thr Ile Thr Glu Ile Phe Glu Asn Leu Glu Glu Asn Ala
945                 950                 955                 960
```

*FIG. 2f*

```
GTA GAA AGT AAT GAA AAT GTT GCA GAG AAT TTA GAG AAA TTA AAC GAA  2928
Val Glu Ser Asn Glu Asn Val Ala Glu Asn Leu Glu Lys Leu Asn Glu
            965             970             975

ACT GTA TTT AAT ACT GTA TTA GAT AAA GTA GAG GAA ACA GTA GAA ATT  2976
Thr Val Phe Asn Thr Val Leu Asp Lys Val Glu Glu Thr Val Glu Ile
            980             985             990

AGC GGA GAA AGT TTA GAA AAC AAT GAA ATG GAT AAA GCA TTT TTT AGT  3024
Ser Gly Glu Ser Leu Glu Asn Asn Glu Met Asp Lys Ala Phe Phe Ser
            995            1000            1005

GAA ATA TTT GAT AAT GTA AAA GGA ATA CAA GAA AAT TTA TTA ACA GGT  3072
Glu Ile Phe Asp Asn Val Lys Gly Ile Gln Glu Asn Leu Leu Thr Gly
           1010            1015            1020

ATG TTT CGA AGT ATA GAA ACC AGT ATA GTA ATC CAA TCA GAA GAA AAG  3120
Met Phe Arg Ser Ile Glu Thr Ser Ile Val Ile Gln Ser Glu Glu Lys
           1025            1030            1035            1040

GTT GAT TTG AAT GAA AAT GTG GTT AGT TCG ATT TTA GAT AAT ATA GAA  3168
Val Asp Leu Asn Glu Asn Val Val Ser Ser Ile Leu Asp Asn Ile Glu
           1045            1050            1055

AAT ATG AAA GAA GGT TTA TTA AAT AAA TTA GAA AAT ATT TCA AGT ACT  3216
Asn Met Lys Glu Gly Leu Leu Asn Lys Leu Glu Asn Ile Ser Ser Thr
           1060            1065            1070

GAA GGT GTT CAA GAA ACT GTA ACT GAA CAT GTA GAA CAA AAT GTA TAT  3264
Glu Gly Val Gln Glu Thr Val Thr Glu His Val Glu Gln Asn Val Tyr
           1075            1080            1085

GTG GAT GTT GAT GTT CCT GCT ATG AAA GAT CAA TTT TTA GGA ATA TTA  3312
Val Asp Val Asp Val Pro Ala Met Lys Asp Gln Phe Leu Gly Ile Leu
           1090            1095            1100

AAT GAG GCA GGA GGG TTG AAA GAA ATG TTT TTT AAT TTG GAA GAT GTA  3360
Asn Glu Ala Gly Gly Leu Lys Glu Met Phe Phe Asn Leu Glu Asp Val
           1105            1110            1115            1120
```

*FIG. 2g*

```
TTT AAA AGT GAA AGT GAT GTA ATT ACT GTA GAA GAA ATT AAG GAT GAA   3408
Phe Lys Ser Glu Ser Asp Val Ile Thr Val Glu Glu Ile Lys Asp Glu
            1125              1130              1135

CCG GTT CAA AAA GAG GTA GAA AAA GAA ACT GTT AGT ATT ATT GAA GAA   3456
Pro Val Gln Lys Glu Val Glu Lys Glu Thr Val Ser Ile Ile Glu Glu
        1140              1145              1150

ATG GAA GAA AAT ATT GTA GAT GTA TTA GAG GAA GAA AAA GAA GAT TTA   3504
Met Glu Glu Asn Ile Val Asp Val Leu Glu Glu Glu Lys Glu Asp Leu
        1155              1160              1165

ACA GAC AAG ATG ATA GAT GCA GTA GAA GAA TCC ATA GAA ATA TCT TCA   3552
Thr Asp Lys Met Ile Asp Ala Val Glu Glu Ser Ile Glu Ile Ser Ser
        1170              1175              1180

GAT TCT AAA GAA GAA ACT GAA TCT ATT AAA GAT AAA GAA AAA GAT GTT   3600
Asp Ser Lys Glu Glu Thr Glu Ser Ile Lys Asp Lys Glu Lys Asp Val
1185              1190              1195              1200

TCA CTA GTT GTT GAA GAA GTT CAA GAC AAT GAT ATG GAT GAA AGT GTT   3648
Ser Leu Val Val Glu Glu Val Gln Asp Asn Asp Met Asp Glu Ser Val
        1205              1210              1215

GAG AAA GTT TTA GAA TTG AAA AAT ATG GAA GAG GAG TTA ATG AAG GAT   3696
Glu Lys Val Leu Glu Leu Lys Asn Met Glu Glu Glu Leu Met Lys Asp
        1220              1225              1230

GCT GTT GAA ATA AAT GAC ATT ACT AGC AAA CTT ATT GAA GAA ACT CAA   3744
Ala Val Glu Ile Asn Asp Ile Thr Ser Lys Leu Ile Glu Glu Thr Gln
        1235              1240              1245

GAG TTA AAT GAA GTA GAA GCA GAT TTA ATA AAA GAT ATG GAA AAA TTA   3792
Glu Leu Asn Glu Val Glu Ala Asp Leu Ile Lys Asp Met Glu Lys Leu
        1250              1255              1260

AAA GAA TTA GAA AAA GCA TTA TCA GAA GAT TCT AAA GAA ATA ATA GAT   3840
Lys Glu Leu Glu Lys Ala Leu Ser Glu Asp Ser Lys Glu Ile Ile Asp
1265              1270              1275              1280
```

*FIG. 2h*

```
GCA AAA GAT GAT ACA TTA GAA AAA GTT ATT GAA GAG GAA CAT GAT ATA    3888
Ala Lys Asp Asp Thr Leu Glu Lys Val Ile Glu Glu Glu His Asp Ile
            1285                1290                1295

ACG ACG ACG TTG GAT GAA GTT GTA GAA TTA AAA GAT GTC GAA GAA GAC    3936
Thr Thr Thr Leu Asp Glu Val Val Glu Leu Lys Asp Val Glu Glu Asp
        1300                1305                1310

AAG ATC GAA AAA GTA TCT GAT TTA AAA GAT CTT GAA GAA GAT ATA TTA    3984
Lys Ile Glu Lys Val Ser Asp Leu Lys Asp Leu Glu Glu Asp Ile Leu
        1315                1320                1325

AAA GAA GTA AAA GAA ATC AAA GAA CTT GAA AGT GAA ATT TTA GAA GAT    4032
Lys Glu Val Lys Glu Ile Lys Glu Leu Glu Ser Glu Ile Leu Glu Asp
        1330                1335                1340

TAT AAA GAA TTA AAA ACT ATT GAA ACA GAT ATT TTA GAA GAG AAA AAA    4080
Tyr Lys Glu Leu Lys Thr Ile Glu Thr Asp Ile Leu Glu Glu Lys Lys
1345            1350                1355                1360

GAA ATA GAA AAA GAT CAT TTT GAA AAA TTC GAA GAA GAA GCT GAA GAA    4128
Glu Ile Glu Lys Asp His Phe Glu Lys Phe Glu Glu Glu Ala Glu Glu
                1365                1370                1375

ATA AAA GAT CTT GAA GCA GAT ATA TTA AAA GAA GTA TCT TCA TTA GAA    4176
Ile Lys Asp Leu Glu Ala Asp Ile Leu Lys Glu Val Ser Ser Leu Glu
            1380                1385                1390

GTT GAA GAA GAA AAA AAA TTA GAA GAA GTA CAC GAA TTA AAA GAA GAG    4224
Val Glu Glu Glu Lys Lys Leu Glu Glu Val His Glu Leu Lys Glu Glu
            1395                1400                1405

GTA GAA CAT ATA ATA AGT GGT GAT GCG CAT ATA AAA GGT TTG GAA GAA    4272
Val Glu His Ile Ile Ser Gly Asp Ala His Ile Lys Gly Leu Glu Glu
        1410                1415                1420

GAT GAT TTA GAA GAA GTA GAT GAT TTA AAA GGA AGT ATA TTA GAC ATG    4320
Asp Asp Leu Glu Glu Val Asp Asp Leu Lys Gly Ser Ile Leu Asp Met
    1425                1430                1435                1440
```

*FIG. 2i*

```
TTA AAG GGA GAT ATG GAA TTA GGG GAT ATG GAT AAG GAA AGT TTA GAA    4368
Leu Lys Gly Asp Met Glu Leu Gly Asp Met Asp Lys Glu Ser Leu Glu
            1445            1450            1455

GAT GTA ACA ACA AAA CTT GGA GAA AGA GTT GAA TCC TTA AAA GAT GTT    4416
Asp Val Thr Thr Lys Leu Gly Glu Arg Val Glu Ser Leu Lys Asp Val
            1460            1465            1470

TTA TCT AGT GCA TTA GGC ATG GAT GAA GAA CAA ATG AAA ACA AGA AAA    4464
Leu Ser Ser Ala Leu Gly Met Asp Glu Glu Gln Met Lys Thr Arg Lys
            1475            1480            1485

AAA GCT CAA AGA CCT AAG TTG GAA GAA GTA TTA TTA AAA GAA GAG GTT    4512
Lys Ala Gln Arg Pro Lys Leu Glu Glu Val Leu Leu Lys Glu Glu Val
        1490            1495            1500

AAA GAA GAA CCA AAG AAA AAA ATA ACA AAG AAG AAA GTA AGG TTT GAT    4560
Lys Glu Glu Pro Lys Lys Lys Ile Thr Lys Lys Lys Val Arg Phe Asp
1505            1510            1515            1520

ATT AAG GAT AAG GAA CCA AAA GAT GAA ATA GTA GAA GTT GAA ATG AAA    4608
Ile Lys Asp Lys Glu Pro Lys Asp Glu Ile Val Glu Val Glu Met Lys
            1525            1530            1535

GAT GAA GAT ATA GAA GAA GAT GTA GAA GAA GAT ATA GAA GAA GAT ATA    4656
Asp Glu Asp Ile Glu Glu Asp Val Glu Glu Asp Ile Glu Glu Asp Ile
            1540            1545            1550

GAA GAA GAT AAA GTT GAA GAT ATA GAT GAA GAT ATA GAT GAA GAT ATA    4704
Glu Glu Asp Lys Val Glu Asp Ile Asp Glu Asp Ile Asp Glu Asp Ile
            1555            1560            1565

GGT GAA GAC AAA GAT GAA GTT ATA GAT TTA ATA GTC CAA AAA GAG AAA    4752
Gly Glu Asp Lys Asp Glu Val Ile Asp Leu Ile Val Gln Lys Glu Lys
        1570            1575            1580

CGC ATT GAA AAG GTT AAA GCG AAA AAG AAA AAA TTA GAA AAA AAA GTT    4800
Arg Ile Glu Lys Val Lys Ala Lys Lys Lys Lys Leu Glu Lys Lys Val
1585            1590            1595            1600
```

*FIG. 2j*

```
GAA GAA GGT GTT AGT GGT CTT AAA AAA CAC GTA GAC GAA GTA ATG AAA   4848
Glu Glu Gly Val Ser Gly Leu Lys Lys His Val Asp Glu Val Met Lys
             1605            1610            1615

TAT GTT CAA AAA ATT GAT AAA GAA GTA GAT AAA GAA GTA TCT AAA GCT   4896
Tyr Val Gln Lys Ile Asp Lys Glu Val Asp Lys Glu Val Ser Lys Ala
         1620            1625            1630

TTA GAA TCA AAA AAT GAT GTT ACT AAT GTT TTA AAA CAA AAT CAA GAT   4944
Leu Glu Ser Lys Asn Asp Val Thr Asn Val Leu Lys Gln Asn Gln Asp
     1635            1640            1645

TTT TTT AGT AAA GTT AAA AAC TTC GTA AAA AAA TAT AAA GTA TTT GCT   4992
Phe Phe Ser Lys Val Lys Asn Phe Val Lys Lys Tyr Lys Val Phe Ala
      1650            1655            1660

GCA CCA TTC ATA TCT GCC GTT GCA GCA TTT GCA TCA TAT GTA GTT GGG   5040
Ala Pro Phe Ile Ser Ala Val Ala Ala Phe Ala Ser Tyr Val Val Gly
1665            1670            1675            1680

TTC TTT ACA TTT TCT TTA TTT TCA TCA TGT GTA ACA ATA GCT TCT TCA   5088
Phe Phe Thr Phe Ser Leu Phe Ser Ser Cys Val Thr Ile Ala Ser Ser
             1685            1690            1695

ACT TAC TTA TTA TCA AAA GTT GAC AAA ACT ATA AAT AAA AAT AAG GAG   5136
Thr Tyr Leu Leu Ser Lys Val Asp Lys Thr Ile Asn Lys Asn Lys Glu
         1700            1705            1710

AGA CCG TTT TAT TCA TTT GTA TTT GAT ATC TTT AAG AAT TTA AAA CAT   5184
Arg Pro Phe Tyr Ser Phe Val Phe Asp Ile Phe Lys Asn Leu Lys His
     1715            1720            1725

TAT TTA CAA CAA ATG AAA GAA AAA TTT AGT AAA GAA AAA AAT AAT AAT   5232
Tyr Leu Gln Gln Met Lys Glu Lys Phe Ser Lys Glu Lys Asn Asn Asn
      1730            1735            1740

GTA ATA GAA GTA ACA AAC AAA GCT GAG AAA AAA GGT AAT GTA CAG GTA   5280
Val Ile Glu Val Thr Asn Lys Ala Glu Lys Lys Gly Asn Val Gln Val
1745            1750            1755            1760
```

*FIG. 2k*

```
ACA AAT AAA ACC GAG AAA ACA ACT AAA GTT GAT AAA AAT AAT AAA GTA    5328
Thr Asn Lys Thr Glu Lys Thr Thr Lys Val Asp Lys Asn Asn Lys Val
                1765            1770                1775

CCG AAA AAA AGA AGA ACG CAA AAA TCA AAA TAA                        5361
Pro Lys Lys Arg Arg Thr Gln Lys Ser Lys  *
            1780            1785
```

*FIG. 21*

```
T ACA TTA ACT GAA AGT GTA GAT GAT AAT AAA AAT TTA GAA GAA GCC      46
  Thr Leu Thr Glu Ser Val Asp Asp Asn Lys Asn Leu Glu Glu Ala
   1           5                  10                  15

GAA GAT ATA AAG GAA AAT ATC TTA TTA AGT AAT ATA GAA GAA CCA AAA    94
Glu Asp Ile Lys Glu Asn Ile Leu Leu Ser Asn Ile Glu Glu Pro Lys
                20                  25                  30

GAA AAT ATT ATT GAC AAT TTA TTA AAT AAT ATT GGA CAA AAT TCA GAA    142
Glu Asn Ile Ile Asp Asn Leu Leu Asn Asn Ile Gly Gln Asn Ser Glu
            35                  40                  45

AAA CAA GAA AGT GTA TCA GAA AAT GTA CAA GTC AGT GAT GAA CTT TTT    190
Lys Gln Glu Ser Val Ser Glu Asn Val Gln Val Ser Asp Glu Leu Phe
        50                  55                  60

AAT GAA TTA TTA AAT AGT GTA GAT GTT AAT GGA GAA GTA AAA GAA AAT    238
Asn Glu Leu Leu Asn Ser Val Asp Val Asn Gly Glu Val Lys Glu Asn
    65                  70                  75

ATT TTG GAG GAA AGT CAA GTT AAT GAC GAT ATT TTT AAT AGT TTA GTA    286
Ile Leu Glu Glu Ser Gln Val Asn Asp Asp Ile Phe Asn Ser Leu Val
 80                  85                  90                  95

AAA AGT GTT CAA CAA GAA CAA CAA CAC AAT GTT GAA GAA AAA GTT GAA    334
Lys Ser Val Gln Gln Glu Gln Gln His Asn Val Glu Glu Lys Val Glu
                100                 105                 110

GAA AGT GTA GAA GAA AAT GAC GAA GAA AGT GTA GAA GAA AAT GTA GAA    382
Glu Ser Val Glu Glu Asn Asp Glu Glu Ser Val Glu Glu Asn Val Glu
            115                 120                 125

GAA AAT GTA GAA GAA AAT GAC GAC GGA AGT GTA GCC TCA AGT GTT GAA    430
Glu Asn Val Glu Glu Asn Asp Asp Gly Ser Val Ala Ser Ser Val Glu
        130                 135                 140

GAA AGT ATA GCT TCA AGT GTT GAT GAA AGT ATA GAT TCA AGT ATT GAA    478
Glu Ser Ile Ala Ser Ser Val Asp Glu Ser Ile Asp Ser Ser Ile Glu
    145                 150                 155
```

*FIG. 3a*

```
GAA AAT GTA GCT CCA ACT GTT GAA GAA ATC GTA GCT CCA ACT GTT GAA    526
Glu Asn Val Ala Pro Thr Val Glu Glu Ile Val Ala Pro Thr Val Glu
160                 165                 170                 175

GAA ATT GTA GCT CCA AGT GTT GTA GAA AGT GTG GCT CCA AGT GTT GAA    574
Glu Ile Val Ala Pro Ser Val Val Glu Ser Val Ala Pro Ser Val Glu
            180                 185                 190

GAA AGT GTA GCT CCA AGT GTT GAA GAA AGT GTA GCT GAA AAT GTT GAA    622
Glu Ser Val Ala Pro Ser Val Glu Glu Ser Val Ala Glu Asn Val Glu
        195                 200                 205

GAA AGT GTA GCT GAA AAT GTT GAA GAA ATC GTA GCT CCA AGT GTT GAA    670
Glu Ser Val Ala Glu Asn Val Glu Glu Ile Val Ala Pro Ser Val Glu
        210                 215                 220

GAA AGT GTA GCT GAA AAT GTT GAA GAA AGT GTA GCT GAA AAT GTT GAA    718
Glu Ser Val Ala Glu Asn Val Glu Glu Ser Val Ala Glu Asn Val Glu
    225                 230                 235

GAA AGT GTA GCT GAA AAT GTT GAA GAA AGT GTA GCT GAA AAT GTT GAA    766
Glu Ser Val Ala Glu Asn Val Glu Glu Ser Val Ala Glu Asn Val Glu
240                 245                 250                 255

GAA AGT GTA GCT GAA AAT GTT GAA GAA ATC GTA GCT CCA ACT GTT GAA    814
Glu Ser Val Ala Glu Asn Val Glu Glu Ile Val Ala Pro Thr Val Glu
            260                 265                 270

GAA AGT GTA GCT CCA ACT GTT GAA GAA ATT GTA GCT CCA ACT GTT GAA    862
Glu Ser Val Ala Pro Thr Val Glu Glu Ile Val Ala Pro Thr Val Glu
            275                 280                 285

GAA AGT GTA GCT CCA ACT GTT GAA GAA ATT GTA GTT CCA AGT GTT GAA    910
Glu Ser Val Ala Pro Thr Val Glu Glu Ile Val Val Pro Ser Val Glu
            290                 295                 300

GAA AGT GTA GCT CCA AGT GTT GAA GAA AGT GTA GCT GAA AAT GTT GAA    958
Glu Ser Val Ala Pro Ser Val Glu Glu Ser Val Ala Glu Asn Val Glu
        305                 310                 315
```

FIG. 3b

```
GAA AGT GTA GCT GAA AAT GTT GAA GAA AGT GTA GCT GAA AAT GTT GAA    1006
Glu Ser Val Ala Glu Asn Val Glu Glu Ser Val Ala Glu Asn Val Glu
320                 325                 330                 335

GAA AGT GTA GCT GAA AAT GTT GAA GAA AGT GTA GCT GAA AAT GTT GAA    1054
Glu Ser Val Ala Glu Asn Val Glu Glu Ser Val Ala Glu Asn Val Glu
                    340                 345                 350

GAA ATC GTA GCT CCA AGT GTT GAA GAA ATC GTA GCT CCA ACT GTT GAA    1102
Glu Ile Val Ala Pro Ser Val Glu Glu Ile Val Ala Pro Thr Val Glu
                    355                 360                 365

GAA AGT GTT GCT GAA AAC GTT GCA ACA AAT TTA TCA GAC AAT CTT TTA    1150
Glu Ser Val Ala Glu Asn Val Ala Thr Asn Leu Ser Asp Asn Leu Leu
                    370                 375                 380

AGT AAT TTA TTA GGT GGT ATC GAA ACT GAG GAA ATA AAG GAC AGT ATA    1198
Ser Asn Leu Leu Gly Gly Ile Glu Thr Glu Glu Ile Lys Asp Ser Ile
385                 390                 395

TTA AAT GAG ATA GAA GAA GTA AAA GAA AAT GTA GTC ACC ACA ATA CTA    1246
Leu Asn Glu Ile Glu Glu Val Lys Glu Asn Val Val Thr Thr Ile Leu
400                 405                 410                 415

GAA AAA GTA GAA GAA ACT ACA GCT GAA AGT GTA ACT ACT TTT AGT AAT    1294
Glu Lys Val Glu Glu Thr Thr Ala Glu Ser Val Thr Thr Phe Ser Asn
                    420                 425                 430

ATA TTA GAG GAG ATA CAA GAA AAT ACT ATT ACT AAT GAT ACT ATA GAG    1342
Ile Leu Glu Glu Ile Gln Glu Asn Thr Ile Thr Asn Asp Thr Ile Glu
                    435                 440                 445

GAA AAA TTA GAA GAA CTC CAC GAA AAT GTA TTA AGT GCC GCT TTA GAA    1390
Glu Lys Leu Glu Glu Leu His Glu Asn Val Leu Ser Ala Ala Leu Glu
                    450                 455                 460

AAT ACC CAA AGT GAA GAG GAA AAG AAA GAA GTA ATA GAT GTA ATT GAA    1438
Asn Thr Gln Ser Glu Glu Glu Lys Lys Glu Val Ile Asp Val Ile Glu
465                 470                 475
```

*FIG. 3c*

```
GAA GTA AAA GAA GAG GTC GCT ACC ACT TTA ATA GAA ACT GTG GAA CAG   1486
Glu Val Lys Glu Glu Val Ala Thr Thr Leu Ile Glu Thr Val Glu Gln
480             485             490             495

GCA GAA GAA GAG AGC GAA AGT ACA ATT ACG GAA ATA TTT GAA AAT TTA   1534
Ala Glu Glu Glu Ser Glu Ser Thr Ile Thr Glu Ile Phe Glu Asn Leu
                500             505             510

GAA GAA AAT GCA GTA GAA AGT AAT GAA AAA GTT GCA GAG AAT TTA GAG   1582
Glu Glu Asn Ala Val Glu Ser Asn Glu Lys Val Ala Glu Asn Leu Glu
            515             520             525

AAA TTA AAC GAA ACT GTA TTT AAT ACT GTA TTA GAT AAA GTA GAG GAA   1630
Lys Leu Asn Glu Thr Val Phe Asn Thr Val Leu Asp Lys Val Glu Glu
        530             535             540

ACA GTA GAA ATT AGC GGA GAA AGT TTA GAA AAC AAT GAA ATG GAT AAA   1678
Thr Val Glu Ile Ser Gly Glu Ser Leu Glu Asn Asn Glu Met Asp Lys
    545             550             555

GCA TTT TTT AGT GAA ATA TTT GAT AAT GTA AAA GGA ATA CAA GAA AAT   1726
Ala Phe Phe Ser Glu Ile Phe Asp Asn Val Lys Gly Ile Gln Glu Asn
560             565             570             575

TTA TTA AGA GGT ATG TTT CGA AGT ATA GAA ACC AGT ATA GTA ATC CAA   1774
Leu Leu Thr Gly Met Phe Arg Ser Ile Glu Thr Ser Ile Val Ile Gln
                580             585             590

TCA GAA GAA AAG GTT GAT TTG AAT GAA AAT GTG GTT AGT TCG ATT TTA   1822
Ser Glu Glu Lys Val Asp Leu Asn Glu Asn Val Val Ser Ser Ile Leu
            595             600             605

GAT AAT ATA GAA AAT ATG AAA GAA GGT TTA TTA AAT AAA TTA GAA AAT   1870
Asp Asn Ile Glu Asn Met Lys Glu Gly Leu Leu Asn Lys Leu Glu Asn
        610             615             620

ATT TCA AGT ACT GAA GGC GAA                                       1891
Ile Ser Ser Thr Glu Gly Glu
    625             630
```

*FIG. 3d*

SEQUENCE LISTING

<160> NUMBER OF SEQ ID NOS: 29

<210> SEQ ID NO 1
<211> LENGTH: 6152
<212> TYPE: DNA
<213> ORGANISM: P. falciparum

<400> SEQUENCE: 1

| | | | | | |
|---|---|---|---|---|---|
| atttatttat | ttttattgtt | ttatttcttt | tttttcttta | aattgtatat | ttataaatat | 60 |
| tttaaaaagt | tagaaaatga | caaatagtaa | ttacaaatca | aataataaaa | catataatga | 120 |
| aaataataat | gaacaaataa | ctaccatatt | taatagaaca | aatatgaatc | cgataaaaaa | 180 |
| atgtcatatg | agagaaaaaa | taaataagta | ctttttttg | atcaaaattt | tgacatgcac | 240 |
| cattttaata | tgggctgtac | aatatgataa | taacgtaaga | taaaaaacta | aataataaat | 300 |
| ataaataaaa | aaaaaaaaaa | aaaaaaaaaa | atcaactata | tagtatgtat | aatatatata | 360 |
| tatatatata | tatatatata | tatatatata | tatttatttt | tatttattta | ttaattttt | 420 |
| ttttttata | ttatcttttt | agtctgatat | aaacaagagt | tggaaaaaaa | atacgtatgt | 480 |
| agataagaaa | ttgaataaac | tatttaacag | aagtttagga | gaatctcaag | taaatggtga | 540 |
| attagctagt | gaagaagtaa | aggaaaaaat | tcttgactta | ttagaagaag | gaaatacatt | 600 |
| aactgaaagt | gtagatgata | ataaaaattt | agaagaagcc | gaagatataa | aggaaaatat | 660 |
| cttattaagt | aatatagaag | aaccaaaaga | aaatattatt | gacaatttat | taaataatat | 720 |
| tggacaaaat | tcagaaaaac | aagaaagtgt | atcagaaaat | gtacaagtca | gtgatgaact | 780 |
| ttttaatgaa | ttattaaata | gtgtagatgt | taatggagaa | gtaaaagaaa | atatttttgga | 840 |
| ggaaagtcaa | gttaatgacg | atattttttaa | tagtttagta | aaaagtgttc | aacaagaaca | 900 |
| acaacacaat | gttgaagaaa | aagttgaaga | agtgtagaa | gaaaatgacg | aagaaagtgt | 960 |
| agaagaaaat | gtagaagaaa | atgtagaaga | aaatgacgac | ggaagtgtag | cctcaagtgt | 1020 |
| tgaagaaagt | atagcttcaa | gtgttgatga | agtatagat | tcaagtattg | aagaaaatgt | 1080 |
| agctccaact | gttgaagaaa | tcgtagctcc | aagtgttgta | gaagtgtgg | ctccaagtgt | 1140 |
| tgaagaaagt | gtagaagaaa | atgttgaaga | agtgtagct | gaaaatgttg | aagaaagtgt | 1200 |
| agctgaaaat | gttgaagaaa | gtgtagctga | aaatgttgaa | gaagtgtag | ctgaaaatgt | 1260 |
| tgaagaaatc | gtagctccaa | ctgttgaaga | aatcgtagct | ccaactgttg | aagaaattgt | 1320 |
| agctccaagt | gttgtagaaa | gtgtggctcc | aagtgttgaa | gaagtgtag | aagaaaatgt | 1380 |
| tgaagaaagt | gtagctgaaa | atgttgaaga | agtgtagct | gaaaatgttg | aagaaagtgt | 1440 |
| agctgaaaat | gttgaagaaa | gtgtagctga | aaatgttgaa | gaagtgtag | ctgaaaatgt | 1500 |
| tgaagaaatc | gtagctccaa | ctgttgaaga | aatcgtagct | ccaactgttg | aagaaattgt | 1560 |
| agctccaagt | gttgtagaaa | gtgtggctcc | aagtgttgaa | gaagtgtag | aagaaaatgt | 1620 |
| tgaagaaagt | gtagctgaaa | atgttgaaga | agtgtagct | gaaaatgttg | aagaaagtgt | 1680 |
| agctgaaaat | gttgaagaaa | gtgtagctga | aaatgttgaa | gaagtgtag | ctgaaaatgt | 1740 |
| tgaagaaagt | gtagctgaaa | atgttgaaga | agtgtagct | gaaaatgttg | aagaaatcgt | 1800 |
| agctccaact | gttgaagaaa | tcgtagctcc | aactgttgaa | gaattgtag | ctccaagtgt | 1860 |
| tgtagaaagt | gtggctccaa | gtgttgaaga | agtgtagaa | gaaaatgttg | aagaaagtgt | 1920 |
| agctgaaaat | gttgaagaaa | gtgtagctga | aaatgttgaa | gaagtgtag | ctgaaaatgt | 1980 |
| tgaagaaagt | gtagctgaaa | atgttgaaga | aatcgtagct | ccaactgttg | aagaaatcgt | 2040 |

```
agctccaact gttgaagaaa ttgtagctcc aagtgttgta gaaagtgtgg ctccaagtgt   2100
tgaagaaagt gtagaagaaa atgttgaaga agtgtagct gaaaatgttg aagaaagtgt    2160
agctgaaaat gttgaagaaa gtgtagctga aatgttgaa gaaatcgtag ctccaactgt    2220
tgaagaaatc gtagctccaa ctgttgaaga aattgtagct ccaagtgttg tagaaagtgt   2280
ggctccaagt gttgaagaaa gtgtagaaga aatgttgaa gaaagtgtag ctgaaaatgt    2340
tgaagaaagt gtagctgaaa atgttgaaga agtgtagct gaaaatgttg aagaaagtgt    2400
agctgaaaat gttgaagaaa tcgtagctcc aactgttgaa gaaatcgtag ctccaactgt   2460
tgaagaaatt gtagctccaa gtgttgtaga agtgtggct ccaagtgttg aagaaagtgt    2520
agaagaaaat gttgaagaaa gtgtagctga aatgttgaa gaaagtgtag ctgaaaatgt    2580
tgaagaaagt gtagctgaaa atgttgaaga agtgtagct ccaactgttg aagaaattgt    2640
agctccaagt gttgaagaaa gtgtagctcc aagtgttgaa gaaagtgttg ctgaaaacgt    2700
tgcaacaaat ttatcagaca atcttttaag taatttatta ggtggtatcg aaactgagga   2760
aataaaggac agtatattaa atgagataga agaagtaaaa gaaatgtag tcaccacaat    2820 actagaaaac gtagaagaaa ctacagctga agtgtaact acttttagta acatattaga    2880
ggagatacaa gaaaatacta ttactaatga tactatagag gaaaaattag aagaactcca   2940
cgaaaatgta ttaagtgccg ctttagaaaa tacccaaagt gaagaggaaa agaaagaagt   3000
aatagatgta attgaagaag taaaagaaga ggtcgctacc actttaatag aaactgtgga   3060
acaggcagaa gaaaagagcg caaatacaat tacggaaata tttgaaaatt tagaagaaaa   3120
tgcagtagaa agtaatgaaa atgttgcaga gaatttagag aaattaaacg aaactgtatt   3180
taatactgta ttagataaag tagaggaaac agtagaaatt agcggagaaa gtttagaaaa   3240
caatgaaatg gataaagcat ttttagtga aatatttgat aatgtaaaag gaatacaaga    3300
aaatttatta acaggtatgt ttcgaagtat agaaaccagt atagtaatcc aatcagaaga   3360
aaaggttgat ttgaatgaaa atgtggttag ttcgatttta gataatatag aaaatatgaa   3420
agaaggttta ttaaataaat tagaaaatat ttcaagtact gaaggtgttc aagaaactgt   3480
aactgaacat gtagaacaaa atgtatatgt ggatgttgat gttcctgcta tgaaagatca   3540
atttttagga atattaaatg aggcaggagg gttgaaagaa atgtttttta atttggaaga   3600
tgtatttaaa agtgaaagtg atgtaattac tgtagaagaa attaaggatg aaccggttca   3660
aaaagaggta gaaaagaaa ctgttagtat tattgaagaa atggaagaaa atattgtaga    3720
tgtattagag gaagaaaaag aagatttaac agacaagatg atagatgcag tagaagaatc   3780
catagaaata tcttcagatt ctaaagaaga aactgaatct attaaagata agaaaaaga    3840 tgtttcacta gttgttgaag aagttcaaga caatgatatg gatgaaagtg ttgagaaagt   3900
tttagaattg aaaaatatgg aagaggagtt aatgaaggat gctgttgaaa taatgacat    3960 tactagcaaa cttattgaag aaactcaaga gttaaatgaa gtagaagcag atttaataaa   4020
agatatggaa aaattaaaag aattagaaaa agcattatca gaagattcta agaaaataat   4080
agatgcaaaa gatgatacat tagaaaaagt tattgaagag gaacatgata taacgacgac   4140
gttggatgaa gttgtagaat taaaagatgt cgaagaagac aagatcgaaa agtatctga    4200 tttaaaagat cttgaagaag atatattaaa agaagtaaaa gaaatcaaag aacttgaaag   4260
tgaaatttta gaagattata agaattaaa aactattgaa acagatattt tagaagagaa    4320
aaagaaaata gaaaagatc attttgaaaa attcgaagaa gaagctgaag aaataaaaga   4380
```

-continued

```
tcttgaagca gatatattaa aagaagtatc ttcattagaa gttgaagaag aaaaaaaatt    4440
agaagaagta cacgaattaa aagaagaggt agaacatata ataagtggtg atgcgcatat    4500
aaaaggtttg gaagaagatg atttagaaga agtagatgat ttaaaaggaa gtatattaga    4560
catgttaaag ggagatatgg aattagggga tatggataag gaaagtttag aagatgtaac    4620
aacaaaactt ggagaaagag ttgaatcctt aaaagatgtt ttatctagtg cattaggcat    4680
ggatgaagaa caaatgaaaa caagaaaaaa agctcaaaga cctaagttgg aagaagtatt    4740
attaaaagaa gaggttaaag aagaaccaaa gaaaaaaata acaaaaaaga agtaaggtt     4800
tgatattaag gataaggaac caaaagatga aatagtagaa gttgaaatga agatgaaga     4860
tatagaagaa gatgtagaag aagatataga agaagatata gaagaagata agttgaaga     4920
tatagatgaa gatatagatg aagatatagg tgaagacaaa gatgaagtta tagatttaat    4980
agtccaaaaa gagaaacgca ttgaaaaggt taaagcgaaa aagaaaaaat tagaaaaaaa    5040
agttgaagaa ggtgttagtg gtcttaaaaa acacgtagac gaagtaatga aatatgttca    5100
aaaaattgat aaagaagttg ataagaagt atctaaagct ttagaatcaa aaaatgatgt    5160
tactaatgtt ttaaaacaaa atcaagattt ttttagtaaa gttaaaaact tcgtaaaaaa    5220
atataaagta tttgctgcac cattcatatc tgccgttgca gcatttgcat catatgtagt    5280
tgggttcttt acattttctt tattttcatc atgtgtaaca atagcttctt caacttactt    5340
attatcaaaa gttgacaaaa ctataaataa aaataaggag agaccgtttt attcatttgt    5400
atttgatatc tttaagaatt taaaacatta tttacaacaa atgaaagaaa aatttagtaa    5460
agaaaaaaat aataatgtaa tagaagtaac aaacaaagct gagaaaaaag gtaatgtaca    5520
ggtaacaaat aaaaccgaga aaacaactaa agttgataaa aataataaag taccgaaaaa    5580
aagaagaacg caaaaatcaa aataaaaaat tgcagaagag tgaaatgatt ggagcgaaca    5640
ataaaattaa tcgataaaaa atataaaaat gtatatatta tgtaaatata taaaataaa    5700
taaataaata catacatata tatatatata tatatgtatc ttttttacaaa attttaaaat    5760
tttaaaattt atatatatta atattttatt ttttccatat ataattttat tttcaatatt    5820
ttattttttaa ttataaatgt ttttttacaga gtttatgttt tttaattaat atatagattt   5880
ctgtaagaaa ctgtatatta ttcatacgat atatgtaata ttaattattt gtgtttttatt   5940
aaaatttata ttatataata tatatatata tatatgtta tatatattag aagataaaaa    6000
tttagcttat tttgcttgtt atgcaaataa gcttttttttt ttttttttttt ttttttttc    6060
atataaacga tgtttaattt ttaatttta atattttata taaaatatttt ttcctaaaaa    6120
aaaaaaaaat taaaaaaaac ttatatttcg aa                                  6152
```

<210> SEQ ID NO 2
<211> LENGTH: 5361
<212> TYPE: DNA
<213> ORGANISM: P. falciparum
<220> FEATURE:
<221> NAME/KEY: CDS
<222> LOCATION: (1)..(5361)
<223> OTHER INFORMATION:

<400> SEQUENCE: 2

```
atg aca aat agt aat tac aaa tca aat aat aaa aca tat aat gaa aat      48
Met Thr Asn Ser Asn Tyr Lys Ser Asn Asn Lys Thr Tyr Asn Glu Asn
1               5                   10                  15 aat aat gaa caa ata act acc ata ttt aat aga aca aat atg aat ccg      96
Asn Asn Glu Gln Ile Thr Thr Ile Phe Asn Arg Thr Asn Met Asn Pro
            20                  25                  30
```

| | | |
|---|---|---|
| ata aaa aaa tgt cat atg aga gaa aaa ata aat aag tac ttt ttt ttg<br>Ile Lys Lys Cys His Met Arg Glu Lys Ile Asn Lys Tyr Phe Phe Leu<br>           35                    40                    45 | 144 |
| atc aaa att ttg aca tgc acc att tta ata tgg gct gta caa tat gat<br>Ile Lys Ile Leu Thr Cys Thr Ile Leu Ile Trp Ala Val Gln Tyr Asp<br> 50                      55                    60 | 192 |
| aat aac tct gat ata aac aag agt tgg aaa aaa aat acg tat gta gat<br>Asn Asn Ser Asp Ile Asn Lys Ser Trp Lys Lys Asn Thr Tyr Val Asp<br>65                  70                    75                    80 | 240 |
| aag aaa ttg aat aaa cta ttt aac aga agt tta gga gaa tct caa gta<br>Lys Lys Leu Asn Lys Leu Phe Asn Arg Ser Leu Gly Glu Ser Gln Val<br>                    85                    90                    95 | 288 |
| aat ggt gaa tta gct agt gaa gaa gta aag gaa aaa att ctt gac tta<br>Asn Gly Glu Leu Ala Ser Glu Glu Val Lys Glu Lys Ile Leu Asp Leu<br>            100                    105                 110 | 336 |
| tta gaa gaa gga aat aca tta act gaa agt gta gat gat aat aaa aat<br>Leu Glu Glu Gly Asn Thr Leu Thr Glu Ser Val Asp Asp Asn Lys Asn<br>            115                    120                 125 | 384 |
| tta gaa gaa gcc gaa gat ata aag gaa aat atc tta tta agt aat ata<br>Leu Glu Glu Ala Glu Asp Ile Lys Glu Asn Ile Leu Leu Ser Asn Ile<br>130                    135                    140 | 432 |
| gaa gaa cca aaa gaa aat att att gac aat tta tta aat aat att gga<br>Glu Glu Pro Lys Glu Asn Ile Ile Asp Asn Leu Leu Asn Asn Ile Gly<br>145                    150                    155                 160 | 480 |
| caa aat tca gaa aaa caa gaa agt gta tca gaa aat gta caa gtc agt<br>Gln Asn Ser Glu Lys Gln Glu Ser Val Ser Glu Asn Val Gln Val Ser<br>                    165                    170                 175 | 528 |
| gat gaa ctt ttt aat gaa tta tta aat agt gta gat gtt aat gga gaa<br>Asp Glu Leu Phe Asn Glu Leu Leu Asn Ser Val Asp Val Asn Gly Glu<br>            180                    185                 190 | 576 |
| gta aaa gaa aat att ttg gag gaa agt caa gtt aat gac gat att ttt<br>Val Lys Glu Asn Ile Leu Glu Glu Ser Gln Val Asn Asp Asp Ile Phe<br>            195                    200                 205 | 624 |
| aat agt tta gta aaa agt gtt caa caa gaa caa caa cac aat gtt gaa<br>Asn Ser Leu Val Lys Ser Val Gln Gln Glu Gln Gln His Asn Val Glu<br>210                    215                    220 | 672 |
| gaa aaa gtt gaa gaa agt gta gaa gaa aat gac gaa gaa agt gta gaa<br>Glu Lys Val Glu Glu Ser Val Glu Glu Asn Asp Glu Glu Ser Val Glu<br>225                    230                    235                 240 | 720 |
| gaa aat gta gaa gaa aat gta gaa gaa aat gac gac gga agt gta gcc<br>Glu Asn Val Glu Glu Asn Val Glu Glu Asn Asp Asp Gly Ser Val Ala<br>            245                    250                 255 | 768 |
| tca agt gtt gaa gaa agt ata gct tca agt gtt gat gaa agt ata gat<br>Ser Ser Val Glu Glu Ser Ile Ala Ser Ser Val Asp Glu Ser Ile Asp<br>            260                    265                 270 | 816 |
| tca agt att gaa gaa aat gta gct cca act gtt gaa gaa atc gta gct<br>Ser Ser Ile Glu Glu Asn Val Ala Pro Thr Val Glu Glu Ile Val Ala<br>            275                    280                 285 | 864 |
| cca agt gtt gta gaa agt gtg gct cca agt gtt gaa gaa agt gta gaa<br>Pro Ser Val Val Glu Ser Val Ala Pro Ser Val Glu Glu Ser Val Glu<br>290                    295                    300 | 912 |
| gaa aat gtt gaa gaa agt gta gct gaa aat gtt gaa gaa agt gta gct<br>Glu Asn Val Glu Glu Ser Val Ala Glu Asn Val Glu Glu Ser Val Ala<br>305                    310                    315                 320 | 960 |
| gaa aat gtt gaa gaa agt gta gct gaa aat gtt gaa gaa agt gta gct<br>Glu Asn Val Glu Glu Ser Val Ala Glu Asn Val Glu Glu Ser Val Ala<br>            325                    330                 335 | 1008 |
| gaa aat gtt gaa gaa atc gta gct cca act gtt gaa gaa atc gta gct<br>Glu Asn Val Glu Glu Ile Val Ala Pro Thr Val Glu Glu Ile Val Ala | 1056 |

```
                340             345             350
cca act gtt gaa gaa att gta gct cca agt gtt gta gaa agt gtg gct       1104
Pro Thr Val Glu Glu Ile Val Ala Pro Ser Val Val Glu Ser Val Ala
        355             360             365 cca agt gtt gaa gaa agt gta gaa gaa aat gtt gaa gaa agt gta gct       1152
Pro Ser Val Glu Glu Ser Val Glu Glu Asn Val Glu Glu Ser Val Ala
    370             375             380 gaa aat gtt gaa gaa agt gta gct gaa aat gtt gaa gaa agt gta gct       1200
Glu Asn Val Glu Glu Ser Val Ala Glu Asn Val Glu Glu Ser Val Ala
385             390             395             400 gaa aat gtt gaa gaa agt gta gct gaa aat gtt gaa gaa agt gta gct       1248
Glu Asn Val Glu Glu Ser Val Ala Glu Asn Val Glu Glu Ser Val Ala
            405             410             415 gaa aat gtt gaa gaa atc gta gct cca act gtt gaa gaa atc gta gct       1296
Glu Asn Val Glu Glu Ile Val Ala Pro Thr Val Glu Glu Ile Val Ala
            420             425             430 cca act gtt gaa gaa att gta gct cca agt gtt gta gaa agt gtg gct       1344
Pro Thr Val Glu Glu Ile Val Ala Pro Ser Val Val Glu Ser Val Ala
            435             440             445 cca agt gtt gaa gaa agt gta gaa gaa aat gtt gaa gaa agt gta gct       1392
Pro Ser Val Glu Glu Ser Val Glu Glu Asn Val Glu Glu Ser Val Ala
        450             455             460 gaa aat gtt gaa gaa agt gta gct gaa aat gtt gaa gaa agt gta gct       1440
Glu Asn Val Glu Glu Ser Val Ala Glu Asn Val Glu Glu Ser Val Ala
465             470             475             480 gaa aat gtt gaa gaa agt gta gct gaa aat gtt gaa gaa agt gta gct       1488
Glu Asn Val Glu Glu Ser Val Ala Glu Asn Val Glu Glu Ser Val Ala
            485             490             495 gaa aat gtt gaa gaa agt gta gct gaa aat gtt gaa gaa agt gta gct       1536
Glu Asn Val Glu Glu Ser Val Ala Glu Asn Val Glu Glu Ser Val Ala
            500             505             510 gaa aat gtt gaa gaa atc gta gct cca act gtt gaa gaa atc gta gct       1584
Glu Asn Val Glu Glu Ile Val Ala Pro Thr Val Glu Glu Ile Val Ala
            515             520             525 cca act gtt gaa gaa att gta gct cca agt gtt gta gaa agt gtg gct       1632
Pro Thr Val Glu Glu Ile Val Ala Pro Ser Val Val Glu Ser Val Ala
            530             535             540 cca agt gtt gaa gaa agt gta gaa gaa aat gtt gaa gaa agt gta gct       1680
Pro Ser Val Glu Glu Ser Val Glu Glu Asn Val Glu Glu Ser Val Ala
545             550             555             560 gaa aat gtt gaa gaa agt gta gct gaa aat gtt gaa gaa agt gta gct       1728
Glu Asn Val Glu Glu Ser Val Ala Glu Asn Val Glu Glu Ser Val Ala
            565             570             575 gaa aat gtt gaa gaa agt gta gct gaa aat gtt gaa gaa atc gta gct       1776
Glu Asn Val Glu Glu Ser Val Ala Glu Asn Val Glu Glu Ile Val Ala
            580             585             590 cca act gtt gaa gaa atc gta gct cca act gtt gaa gaa att gta gct       1824
Pro Thr Val Glu Glu Ile Val Ala Pro Thr Val Glu Glu Ile Val Ala
            595             600             605 cca agt gtt gta gaa agt gtg gct cca agt gtt gaa gaa agt gta gaa       1872
Pro Ser Val Val Glu Ser Val Ala Pro Ser Val Glu Glu Ser Val Glu
            610             615             620 gaa aat gtt gaa gaa agt gta gct gaa aat gtt gaa gaa agt gta gct       1920
Glu Asn Val Glu Glu Ser Val Ala Glu Asn Val Glu Glu Ser Val Ala
625             630             635             640 gaa aat gtt gaa gaa agt gta gct gaa aat gtt gaa gaa atc gta gct       1968
Glu Asn Val Glu Glu Ser Val Ala Glu Asn Val Glu Glu Ile Val Ala
            645             650             655 cca act gtt gaa gaa atc gta gct cca act gtt gaa gaa att gta gct       2016
```

```
                                                    -continued

Pro Thr Val Glu Glu Ile Val Ala Pro Thr Val Glu Glu Ile Val Ala
            660                 665                 670 cca agt gtt gta gaa agt gtg gct cca agt gtt gaa gaa agt gta gaa    2064
Pro Ser Val Val Glu Ser Val Ala Pro Ser Val Glu Glu Ser Val Glu
            675                 680                 685 gaa aat gtt gaa gaa agt gta gct gaa aat gtt gaa gaa agt gta gct    2112
Glu Asn Val Glu Glu Ser Val Ala Glu Asn Val Glu Glu Ser Val Ala
            690                 695                 700 gaa aat gtt gaa gaa agt gta gct gaa aat gtt gaa gaa agt gta gct    2160
Glu Asn Val Glu Glu Ser Val Ala Glu Asn Val Glu Glu Ser Val Ala
705                 710                 715                 720 gaa aat gtt gaa gaa atc gta gct cca act gtt gaa gaa atc gta gct    2208
Glu Asn Val Glu Glu Ile Val Ala Pro Thr Val Glu Glu Ile Val Ala
            725                 730                 735 cca act gtt gaa gaa att gta gct cca agt gtt gta gaa agt gtg gct    2256
Pro Thr Val Glu Glu Ile Val Ala Pro Ser Val Val Glu Ser Val Ala
            740                 745                 750 cca agt gtt gaa gaa agt gta gaa gaa aat gtt gaa gaa agt gta gct    2304
Pro Ser Val Glu Glu Ser Val Glu Glu Asn Val Glu Glu Ser Val Ala
            755                 760                 765 gaa aat gtt gaa gaa agt gta gct gaa aat gtt gaa gaa agt gta gct    2352
Glu Asn Val Glu Glu Ser Val Ala Glu Asn Val Glu Glu Ser Val Ala
770                 775                 780 gaa aat gtt gaa gaa agt gta gct cca act gtt gaa gaa att gta gct    2400
Glu Asn Val Glu Glu Ser Val Ala Pro Thr Val Glu Glu Ile Val Ala
785                 790                 795                 800 cca agt gtt gaa gaa agt gta gct cca agt gtt gaa gaa agt gtt gct    2448
Pro Ser Val Glu Glu Ser Val Ala Pro Ser Val Glu Glu Ser Val Ala
            805                 810                 815 gaa aac gtt gca aca aat tta tca gac aat ctt tta agt aat tta tta    2496
Glu Asn Val Ala Thr Asn Leu Ser Asp Asn Leu Leu Ser Asn Leu Leu
            820                 825                 830 ggt ggt atc gaa act gag gaa ata aag gac agt ata tta aat gag ata    2544
Gly Gly Ile Glu Thr Glu Glu Ile Lys Asp Ser Ile Leu Asn Glu Ile
            835                 840                 845 gaa gaa gta aaa gaa aat gta gtc acc aca ata cta gaa aac gta gaa    2592
Glu Glu Val Lys Glu Asn Val Val Thr Thr Ile Leu Glu Asn Val Glu
            850                 855                 860 gaa act aca gct gaa agt gta act act ttt agt aac ata tta gag gag    2640
Glu Thr Thr Ala Glu Ser Val Thr Thr Phe Ser Asn Ile Leu Glu Glu
865                 870                 875                 880 ata caa gaa aat act att act aat gat act ata gag gaa aaa tta gaa    2688
Ile Gln Glu Asn Thr Ile Thr Asn Asp Thr Ile Glu Glu Lys Leu Glu
            885                 890                 895 gaa ctc cac gaa aat gta tta agt gcc gct tta gaa aat acc caa agt    2736
Glu Leu His Glu Asn Val Leu Ser Ala Ala Leu Glu Asn Thr Gln Ser
            900                 905                 910 gaa gag gaa aag aaa gaa gta ata gat gta att gaa gaa gta aaa gaa    2784
Glu Glu Glu Lys Lys Glu Val Ile Asp Val Ile Glu Glu Val Lys Glu
            915                 920                 925 gag gtc gct acc act tta ata gaa act gtg gaa cag gca gaa gaa aag    2832
Glu Val Ala Thr Thr Leu Ile Glu Thr Val Glu Gln Ala Glu Glu Lys
            930                 935                 940 agc gca aat aca att acg gaa ata ttt gaa aat tta gaa gaa aat gca    2880
Ser Ala Asn Thr Ile Thr Glu Ile Phe Glu Asn Leu Glu Glu Asn Ala
945                 950                 955                 960 gta gaa agt aat gaa aat gtt gca gag aat tta gag aaa tta aac gaa    2928
Val Glu Ser Asn Glu Asn Val Ala Glu Asn Leu Glu Lys Leu Asn Glu
            965                 970                 975
```

-continued

```
act gta ttt aat act gta tta gat aaa gta gag gaa aca gta gaa att    2976
Thr Val Phe Asn Thr Val Leu Asp Lys Val Glu Glu Thr Val Glu Ile
            980                 985                 990 agc gga gaa agt tta gaa aac aat  gaa atg gat aaa gca ttt ttt agt   3024
Ser Gly Glu Ser Leu Glu Asn Asn  Glu Met Asp Lys Ala Phe Phe Ser
            995                 1000                1005 gaa ata ttt gat aat gta aaa  gga ata caa gaa aat  tta tta aca      3069
Glu Ile Phe Asp Asn Val Lys  Gly Ile Gln Glu Asn  Leu Leu Thr
            1010                1015                1020 ggt atg ttt cga agt ata gaa  acc agt ata gta atc  caa tca gaa      3114
Gly Met Phe Arg Ser Ile Glu  Thr Ser Ile Val Ile  Gln Ser Glu
            1025                1030                1035 gaa aag gtt gat ttg aat gaa  aat gtg gtt agt tcg  att tta gat      3159
Glu Lys Val Asp Leu Asn Glu  Asn Val Val Ser Ser  Ile Leu Asp
            1040                1045                1050 aat ata gaa aat atg aaa gaa  ggt tta tta aat aaa  tta gaa aat      3204
Asn Ile Glu Asn Met Lys Glu  Gly Leu Leu Asn Lys  Leu Glu Asn
            1055                1060                1065 att tca agt act gaa ggt gtt  caa gaa act gta act  gaa cat gta      3249
Ile Ser Ser Thr Glu Gly Val  Gln Glu Thr Val Thr  Glu His Val
            1070                1075                1080 gaa caa aat gta tat gtg gat  gtt gat gtt cct gct  atg aaa gat      3294
Glu Gln Asn Val Tyr Val Asp  Val Asp Val Pro Ala  Met Lys Asp
            1085                1090                1095 caa ttt tta gga ata tta aat  gag gca gga ggg ttg  aaa gaa atg      3339
Gln Phe Leu Gly Ile Leu Asn  Glu Ala Gly Gly Leu  Lys Glu Met
            1100                1105                1110 ttt ttt aat ttg gaa gat gta  ttt aaa agt gaa agt  gat gta att      3384
Phe Phe Asn Leu Glu Asp Val  Phe Lys Ser Glu Ser  Asp Val Ile
            1115                1120                1125 act gta gaa gaa att aag gat  gaa ccg gtt caa aaa  gag gta gaa      3429
Thr Val Glu Glu Ile Lys Asp  Glu Pro Val Gln Lys  Glu Val Glu
            1130                1135                1140 aaa gaa act gtt agt att att  gaa gaa atg gaa gaa  aat att gta      3474
Lys Glu Thr Val Ser Ile Ile  Glu Glu Met Glu Glu  Asn Ile Val
            1145                1150                1155 gat gta tta gag gaa gaa aaa  gaa gat tta aca gac  aag atg ata      3519
Asp Val Leu Glu Glu Glu Lys  Glu Asp Leu Thr Asp  Lys Met Ile
            1160                1165                1170 gat gca gta gaa gaa tcc ata  gaa ata tct tca gat  tct aaa gaa      3564
Asp Ala Val Glu Glu Ser Ile  Glu Ile Ser Ser Asp  Ser Lys Glu
            1175                1180                1185 gaa act gaa tct att aaa gat  aaa gaa aaa gat gtt  tca cta gtt      3609
Glu Thr Glu Ser Ile Lys Asp  Lys Glu Lys Asp Val  Ser Leu Val
            1190                1195                1200 gtt gaa gaa gtt caa gac aat  gat atg gat gaa agt  gtt gag aaa      3654
Val Glu Glu Val Gln Asp Asn  Asp Met Asp Glu Ser  Val Glu Lys
            1205                1210                1215 gtt tta gaa ttg aaa aat atg  gaa gag gag tta atg  aag gat gct      3699
Val Leu Glu Leu Lys Asn Met  Glu Glu Glu Leu Met  Lys Asp Ala
            1220                1225                1230 gtt gaa ata aat gac att act  agc aaa ctt att gaa  gaa act caa      3744
Val Glu Ile Asn Asp Ile Thr  Ser Lys Leu Ile Glu  Glu Thr Gln
            1235                1240                1245 gag tta aat gaa gta gaa gca  gat tta ata aaa gat  atg gaa aaa      3789
Glu Leu Asn Glu Val Glu Ala  Asp Leu Ile Lys Asp  Met Glu Lys
            1250                1255                1260 tta aaa gaa tta gaa aaa gca  tta tca gaa gat tct  aaa gaa ata      3834
Leu Lys Glu Leu Glu Lys Ala  Leu Ser Glu Asp Ser  Lys Glu Ile
            1265                1270                1275
```

```
ata gat gca aaa gat gat aca tta gaa aaa gtt att gaa gag gaa        3879
Ile Asp Ala Lys Asp Asp Thr Leu Glu Lys Val Ile Glu Glu Glu
    1280                1285                1290 cat gat ata acg acg acg ttg gat gaa gtt gta gaa tta aaa gat        3924
His Asp Ile Thr Thr Thr Leu Asp Glu Val Val Glu Leu Lys Asp
    1295                1300                1305 gtc gaa gaa gac aag atc gaa aaa gta tct gat tta aaa gat ctt        3969
Val Glu Glu Asp Lys Ile Glu Lys Val Ser Asp Leu Lys Asp Leu
    1310                1315                1320 gaa gaa gat ata tta aaa gaa gta aaa gaa atc aaa gaa ctt gaa        4014
Glu Glu Asp Ile Leu Lys Glu Val Lys Glu Ile Lys Glu Leu Glu
    1325                1330                1335 agt gaa att tta gaa gat tat aaa gaa tta aaa act att gaa aca        4059
Ser Glu Ile Leu Glu Asp Tyr Lys Glu Leu Lys Thr Ile Glu Thr
    1340                1345                1350 gat att tta gaa gag aaa aaa gaa ata gaa aaa gat cat ttt gaa        4104
Asp Ile Leu Glu Glu Lys Lys Glu Ile Glu Lys Asp His Phe Glu
    1355                1360                1365 aaa ttc gaa gaa gaa gct gaa gaa ata aaa gat ctt gaa gca gat        4149
Lys Phe Glu Glu Glu Ala Glu Glu Ile Lys Asp Leu Glu Ala Asp
    1370                1375                1380 ata tta aaa gaa gta tct tca tta gaa gtt gaa gaa gaa aaa aaa        4194
Ile Leu Lys Glu Val Ser Ser Leu Glu Val Glu Glu Glu Lys Lys
    1385                1390                1395 tta gaa gaa gta cac gaa tta aaa gaa gag gta gaa cat ata ata        4239
Leu Glu Glu Val His Glu Leu Lys Glu Glu Val Glu His Ile Ile
    1400                1405                1410 agt ggt gat gcg cat ata aaa ggt ttg gaa gaa gat gat tta gaa        4284
Ser Gly Asp Ala His Ile Lys Gly Leu Glu Glu Asp Asp Leu Glu
    1415                1420                1425 gaa gta gat gat tta aaa gga agt ata tta gac atg tta aag gga        4329
Glu Val Asp Asp Leu Lys Gly Ser Ile Leu Asp Met Leu Lys Gly
    1430                1435                1440 gat atg gaa tta ggg gat atg gat aag gaa agt tta gaa gat gta        4374
Asp Met Glu Leu Gly Asp Met Asp Lys Glu Ser Leu Glu Asp Val
    1445                1450                1455 aca aca aaa ctt gga gaa aga gtt gaa tcc tta aaa gat gtt tta        4419
Thr Thr Lys Leu Gly Glu Arg Val Glu Ser Leu Lys Asp Val Leu
    1460                1465                1470 tct agt gca tta ggc atg gat gaa gaa caa atg aaa aca aga aaa        4464
Ser Ser Ala Leu Gly Met Asp Glu Glu Gln Met Lys Thr Arg Lys
    1475                1480                1485 aaa gct caa aga cct aag ttg gaa gaa gta tta tta aaa gaa gag        4509
Lys Ala Gln Arg Pro Lys Leu Glu Glu Val Leu Leu Lys Glu Glu
    1490                1495                1500 gtt aaa gaa gaa cca aag aaa aaa ata aca aaa aag aaa gta agg        4554
Val Lys Glu Glu Pro Lys Lys Lys Ile Thr Lys Lys Lys Val Arg
    1505                1510                1515 ttt gat att aag gat aag gaa cca aaa gat gaa ata gta gaa gtt        4599
Phe Asp Ile Lys Asp Lys Glu Pro Lys Asp Glu Ile Val Glu Val
    1520                1525                1530 gaa atg aaa gat gaa gat ata gaa gaa gat gta gaa gaa gat ata        4644
Glu Met Lys Asp Glu Asp Ile Glu Glu Asp Val Glu Glu Asp Ile
    1535                1540                1545 gaa gaa gat ata gaa gaa gat aaa gtt gaa gat ata gat gaa gat        4689
Glu Glu Asp Ile Glu Glu Asp Lys Val Glu Asp Ile Asp Glu Asp
    1550                1555                1560 ata gat gaa gat ata ggt gaa gac aaa gat gaa gtt ata gat tta        4734
Ile Asp Glu Asp Ile Gly Glu Asp Lys Asp Glu Val Ile Asp Leu
```

-continued

| | | | | | | | | | | |
|---|---|---|---|---|---|---|---|---|---|---|
| | | | 1565 | | | 1570 | | | 1575 | |
| ata | gtc | caa | aaa | gag | aaa | cgc | att | gaa | aag | gtt | aaa | gcg | aaa | aag | 4779 |
| Ile | Val | Gln | Lys | Glu | Lys | Arg | Ile | Glu | Lys | Val | Lys | Ala | Lys | Lys | |
| | 1580 | | | | 1585 | | | | 1590 | | | | | | |
| aaa | aaa | tta | gaa | aaa | aaa | gtt | gaa | gaa | ggt | gtt | agt | ggt | ctt | aaa | 4824 |
| Lys | Lys | Leu | Glu | Lys | Lys | Val | Glu | Glu | Gly | Val | Ser | Gly | Leu | Lys | |
| 1595 | | | | | 1600 | | | | | 1605 | | | | | |
| aaa | cac | gta | gac | gaa | gta | atg | aaa | tat | gtt | caa | aaa | att | gat | aaa | 4869 |
| Lys | His | Val | Asp | Glu | Val | Met | Lys | Tyr | Val | Gln | Lys | Ile | Asp | Lys | |
| 1610 | | | | | 1615 | | | | | 1620 | | | | | |
| gaa | gtt | gat | aaa | gaa | gta | tct | aaa | gct | tta | gaa | tca | aaa | aat | gat | 4914 |
| Glu | Val | Asp | Lys | Glu | Val | Ser | Lys | Ala | Leu | Glu | Ser | Lys | Asn | Asp | |
| 1625 | | | | | 1630 | | | | | 1635 | | | | | |
| gtt | act | aat | gtt | tta | aaa | caa | aat | caa | gat | ttt | ttt | agt | aaa | gtt | 4959 |
| Val | Thr | Asn | Val | Leu | Lys | Gln | Asn | Gln | Asp | Phe | Phe | Ser | Lys | Val | |
| 1640 | | | | | 1645 | | | | | 1650 | | | | | |
| aaa | aac | ttc | gta | aaa | aaa | tat | aaa | gta | ttt | gct | gca | cca | ttc | ata | 5004 |
| Lys | Asn | Phe | Val | Lys | Lys | Tyr | Lys | Val | Phe | Ala | Ala | Pro | Phe | Ile | |
| 1655 | | | | | 1660 | | | | | 1665 | | | | | |
| tct | gcc | gtt | gca | gca | ttt | gca | tca | tat | gta | gtt | ggg | ttc | ttt | aca | 5049 |
| Ser | Ala | Val | Ala | Ala | Phe | Ala | Ser | Tyr | Val | Val | Gly | Phe | Phe | Thr | |
| 1670 | | | | | 1675 | | | | | 1680 | | | | | |
| ttt | tct | tta | ttt | tca | tca | tgt | gta | aca | ata | gct | tct | tca | act | tac | 5094 |
| Phe | Ser | Leu | Phe | Ser | Ser | Cys | Val | Thr | Ile | Ala | Ser | Ser | Thr | Tyr | |
| 1685 | | | | | 1690 | | | | | 1695 | | | | | |
| tta | tta | tca | aaa | gtt | gac | aaa | act | ata | aat | aaa | aat | aag | gag | aga | 5139 |
| Leu | Leu | Ser | Lys | Val | Asp | Lys | Thr | Ile | Asn | Lys | Asn | Lys | Glu | Arg | |
| 1700 | | | | | 1705 | | | | | 1710 | | | | | |
| ccg | ttt | tat | tca | ttt | gta | ttt | gat | atc | ttt | aag | aat | tta | aaa | cat | 5184 |
| Pro | Phe | Tyr | Ser | Phe | Val | Phe | Asp | Ile | Phe | Lys | Asn | Leu | Lys | His | |
| 1715 | | | | | 1720 | | | | | 1725 | | | | | |
| tat | tta | caa | caa | atg | aaa | gaa | aaa | ttt | agt | aaa | gaa | aaa | aat | aat | 5229 |
| Tyr | Leu | Gln | Gln | Met | Lys | Glu | Lys | Phe | Ser | Lys | Glu | Lys | Asn | Asn | |
| 1730 | | | | | 1735 | | | | | 1740 | | | | | |
| aat | gta | ata | gaa | gta | aca | aac | aaa | gct | gag | aaa | aaa | ggt | aat | gta | 5274 |
| Asn | Val | Ile | Glu | Val | Thr | Asn | Lys | Ala | Glu | Lys | Lys | Gly | Asn | Val | |
| 1745 | | | | | 1750 | | | | | 1755 | | | | | |
| cag | gta | aca | aat | aaa | acc | gag | aaa | aca | act | aaa | gtt | gat | aaa | aat | 5319 |
| Gln | Val | Thr | Asn | Lys | Thr | Glu | Lys | Thr | Thr | Lys | Val | Asp | Lys | Asn | |
| 1760 | | | | | 1765 | | | | | 1770 | | | | | |
| aat | aaa | gta | ccg | aaa | aaa | aga | aga | acg | caa | aaa | tca | aaa | taa | | 5361 |
| Asn | Lys | Val | Pro | Lys | Lys | Arg | Arg | Thr | Gln | Lys | Ser | Lys | | | |
| 1775 | | | | | 1780 | | | | | 1785 | | | | | |

<210> SEQ ID NO 3
<211> LENGTH: 1786
<212> TYPE: PRT
<213> ORGANISM: P. falciparum

<400> SEQUENCE: 3

Met Thr Asn Ser Asn Tyr Lys Ser Asn Asn Lys Thr Tyr Asn Glu Asn
1               5                   10                  15

Asn Asn Glu Gln Ile Thr Thr Ile Phe Asn Arg Thr Asn Met Asn Pro
            20                  25                  30

Ile Lys Lys Cys His Met Arg Glu Lys Ile Asn Lys Tyr Phe Phe Leu
        35                  40                  45

Ile Lys Ile Leu Thr Cys Thr Ile Leu Ile Trp Ala Val Gln Tyr Asp
    50                  55                  60

Asn Asn Ser Asp Ile Asn Lys Ser Trp Lys Lys Asn Thr Tyr Val Asp

-continued

```
             65                  70                  75                  80
Lys Lys Leu Asn Lys Leu Phe Asn Arg Ser Leu Gly Glu Ser Gln Val
                85                  90                  95
Asn Gly Glu Leu Ala Ser Glu Glu Val Lys Glu Lys Ile Leu Asp Leu
               100                 105                 110
Leu Glu Glu Gly Asn Thr Leu Thr Glu Ser Val Asp Asp Asn Lys Asn
               115                 120                 125
Leu Glu Glu Ala Glu Asp Ile Lys Glu Asn Ile Leu Leu Ser Asn Ile
               130                 135                 140
Glu Glu Pro Lys Glu Asn Ile Ile Asp Asn Leu Leu Asn Asn Ile Gly
145                 150                 155                 160
Gln Asn Ser Glu Lys Gln Glu Ser Val Ser Glu Asn Val Gln Val Ser
               165                 170                 175
Asp Glu Leu Phe Asn Glu Leu Leu Asn Ser Val Asp Val Asn Gly Glu
               180                 185                 190
Val Lys Glu Asn Ile Leu Glu Glu Ser Gln Val Asn Asp Asp Ile Phe
               195                 200                 205
Asn Ser Leu Val Lys Ser Val Gln Gln Glu Gln Gln His Asn Val Glu
210                 215                 220
Glu Lys Val Glu Glu Ser Val Glu Glu Asn Asp Glu Glu Ser Val Glu
225                 230                 235                 240
Glu Asn Val Glu Glu Asn Val Glu Glu Asn Asp Asp Gly Ser Val Ala
               245                 250                 255
Ser Ser Val Glu Glu Ser Ile Ala Ser Ser Val Asp Glu Ser Ile Asp
               260                 265                 270
Ser Ser Ile Glu Glu Asn Val Ala Pro Thr Val Glu Glu Ile Val Ala
               275                 280                 285
Pro Ser Val Val Glu Ser Val Ala Pro Ser Val Glu Glu Ser Val Glu
               290                 295                 300
Glu Asn Val Glu Glu Ser Val Ala Glu Asn Val Glu Glu Ser Val Ala
305                 310                 315                 320
Glu Asn Val Glu Glu Ser Val Ala Glu Asn Val Glu Glu Ser Val Ala
               325                 330                 335
Glu Asn Val Glu Glu Ile Val Ala Pro Thr Val Glu Glu Ile Val Ala
               340                 345                 350
Pro Thr Val Glu Glu Ile Val Ala Pro Ser Val Val Glu Ser Val Ala
               355                 360                 365
Pro Ser Val Glu Glu Ser Val Glu Glu Asn Val Glu Glu Ser Val Ala
               370                 375                 380
Glu Asn Val Glu Glu Ser Val Ala Glu Asn Val Glu Glu Ser Val Ala
385                 390                 395                 400
Glu Asn Val Glu Glu Ser Val Ala Glu Asn Val Glu Glu Ser Val Ala
               405                 410                 415
Glu Asn Val Glu Glu Ile Val Ala Pro Thr Val Glu Glu Ile Val Ala
               420                 425                 430
Pro Thr Val Glu Glu Ile Val Ala Pro Ser Val Val Glu Ser Val Ala
               435                 440                 445
Pro Ser Val Glu Glu Ser Val Glu Glu Asn Val Glu Glu Ser Val Ala
               450                 455                 460
Glu Asn Val Glu Glu Ser Val Ala Glu Asn Val Glu Glu Ser Val Ala
465                 470                 475                 480
Glu Asn Val Glu Glu Ser Val Ala Glu Asn Val Glu Glu Ser Val Ala
               485                 490                 495
```

-continued

```
Glu Asn Val Glu Glu Ser Val Ala Glu Asn Val Glu Ser Val Ala
            500                 505                 510
Glu Asn Val Glu Glu Ile Val Ala Pro Thr Val Glu Glu Ile Val Ala
            515                 520                 525
Pro Thr Val Glu Glu Ile Val Ala Pro Ser Val Val Glu Ser Val Ala
            530                 535                 540
Pro Ser Val Glu Glu Ser Val Glu Glu Asn Val Glu Glu Ser Val Ala
545                 550                 555                 560
Glu Asn Val Glu Glu Ser Val Ala Glu Asn Val Glu Glu Ser Val Ala
            565                 570                 575
Glu Asn Val Glu Glu Ser Val Ala Glu Asn Val Glu Glu Ile Val Ala
            580                 585                 590
Pro Thr Val Glu Glu Ile Val Ala Pro Thr Val Glu Glu Ile Val Ala
            595                 600                 605
Pro Ser Val Val Glu Ser Val Ala Pro Ser Val Glu Glu Ser Val Glu
            610                 615                 620
Glu Asn Val Glu Glu Ser Val Ala Glu Asn Val Glu Glu Ser Val Ala
625                 630                 635                 640
Glu Asn Val Glu Glu Ser Val Ala Glu Asn Val Glu Glu Ile Val Ala
            645                 650                 655
Pro Thr Val Glu Glu Ile Val Ala Pro Thr Val Glu Glu Ile Val Ala
            660                 665                 670
Pro Ser Val Val Glu Ser Val Ala Pro Ser Val Glu Glu Ser Val Glu
            675                 680                 685
Glu Asn Val Glu Glu Ser Val Ala Glu Asn Val Glu Glu Ser Val Ala
            690                 695                 700
Glu Asn Val Glu Glu Ser Val Ala Glu Asn Val Glu Glu Ser Val Ala
705                 710                 715                 720
Glu Asn Val Glu Glu Ile Val Ala Pro Thr Val Glu Glu Ile Val Ala
            725                 730                 735
Pro Thr Val Glu Glu Ile Val Ala Pro Ser Val Val Glu Ser Val Ala
            740                 745                 750
Pro Ser Val Glu Glu Ser Val Glu Glu Asn Val Glu Glu Ser Val Ala
            755                 760                 765
Glu Asn Val Glu Glu Ser Val Ala Glu Asn Val Glu Glu Ser Val Ala
            770                 775                 780
Glu Asn Val Glu Glu Ser Val Ala Pro Thr Val Glu Glu Ile Val Ala
785                 790                 795                 800
Pro Ser Val Glu Glu Ser Val Ala Pro Ser Val Glu Glu Ser Val Ala
            805                 810                 815
Glu Asn Val Ala Thr Asn Leu Ser Asp Asn Leu Leu Ser Asn Leu Leu
            820                 825                 830
Gly Gly Ile Glu Thr Glu Ile Lys Asp Ser Ile Leu Asn Glu Ile
            835                 840                 845
Glu Glu Val Lys Glu Asn Val Val Thr Thr Ile Leu Glu Asn Val Glu
850                 855                 860
Glu Thr Thr Ala Glu Ser Val Thr Thr Phe Ser Asn Ile Leu Glu Glu
865                 870                 875                 880
Ile Gln Glu Asn Thr Ile Thr Asn Asp Thr Ile Glu Glu Lys Leu Glu
            885                 890                 895
Glu Leu His Glu Asn Val Leu Ser Ala Ala Leu Glu Asn Thr Gln Ser
            900                 905                 910
```

-continued

```
Glu Glu Glu Lys Lys Glu Val Ile Asp Val Ile Glu Val Lys Glu
        915                 920                 925
Glu Val Ala Thr Thr Leu Ile Glu Thr Val Glu Gln Ala Glu Glu Lys
        930                 935                 940
Ser Ala Asn Thr Ile Thr Glu Ile Phe Glu Asn Leu Glu Glu Asn Ala
945                 950                 955                 960
Val Glu Ser Asn Glu Asn Val Ala Glu Asn Leu Glu Lys Leu Asn Glu
                965                 970                 975
Thr Val Phe Asn Thr Val Leu Asp Lys Val Glu Glu Thr Val Glu Ile
            980                 985                 990
Ser Gly Glu Ser Leu Glu Asn Asn Glu Met Asp Lys Ala Phe Phe Ser
        995                 1000                1005
Glu Ile Phe Asp Asn Val Lys Gly Ile Gln Glu Asn Leu Leu Thr
    1010                1015                1020
Gly Met Phe Arg Ser Ile Glu Thr Ser Ile Val Ile Gln Ser Glu
    1025                1030                1035
Glu Lys Val Asp Leu Asn Glu Asn Val Val Ser Ser Ile Leu Asp
    1040                1045                1050
Asn Ile Glu Asn Met Lys Glu Gly Leu Leu Asn Lys Leu Glu Asn
    1055                1060                1065
Ile Ser Ser Thr Glu Gly Val Gln Glu Thr Val Thr Glu His Val
    1070                1075                1080
Glu Gln Asn Val Tyr Val Asp Val Asp Val Pro Ala Met Lys Asp
    1085                1090                1095
Gln Phe Leu Gly Ile Leu Asn Glu Ala Gly Gly Leu Lys Glu Met
    1100                1105                1110
Phe Phe Asn Leu Glu Asp Val Phe Lys Ser Glu Ser Asp Val Ile
    1115                1120                1125
Thr Val Glu Glu Ile Lys Asp Glu Pro Val Gln Lys Glu Val Glu
    1130                1135                1140
Lys Glu Thr Val Ser Ile Ile Glu Glu Met Glu Glu Asn Ile Val
    1145                1150                1155
Asp Val Leu Glu Glu Glu Lys Glu Asp Leu Thr Asp Lys Met Ile
    1160                1165                1170
Asp Ala Val Glu Glu Ser Ile Glu Ile Ser Ser Asp Ser Lys Glu
    1175                1180                1185
Glu Thr Glu Ser Ile Lys Asp Lys Glu Lys Asp Val Ser Leu Val
    1190                1195                1200
Val Glu Glu Val Gln Asp Asn Asp Met Asp Glu Ser Val Glu Lys
    1205                1210                1215
Val Leu Glu Leu Lys Asn Met Glu Glu Glu Leu Met Lys Asp Ala
    1220                1225                1230
Val Glu Ile Asn Asp Ile Thr Ser Lys Leu Ile Glu Glu Thr Gln
    1235                1240                1245
Glu Leu Asn Glu Val Glu Ala Asp Leu Ile Lys Asp Met Glu Lys
    1250                1255                1260
Leu Lys Glu Leu Glu Lys Ala Leu Ser Glu Asp Ser Lys Glu Ile
    1265                1270                1275
Ile Asp Ala Lys Asp Asp Thr Leu Glu Lys Val Ile Glu Glu Glu
    1280                1285                1290
His Asp Ile Thr Thr Thr Leu Asp Glu Val Val Glu Leu Lys Asp
    1295                1300                1305
Val Glu Glu Asp Lys Ile Glu Lys Val Ser Asp Leu Lys Asp Leu
```

-continued

```
                 1310                1315                1320
Glu Glu Asp Ile Leu Lys Glu Val Lys Glu Ile Lys Glu Leu Glu
    1325                1330                1335

Ser Glu Ile Leu Glu Asp Tyr Lys Glu Leu Lys Thr Ile Glu Thr
    1340                1345                1350

Asp Ile Leu Glu Glu Lys Lys Glu Ile Glu Lys Asp His Phe Glu
    1355                1360                1365

Lys Phe Glu Glu Glu Ala Glu Glu Ile Lys Asp Leu Glu Ala Asp
    1370                1375                1380

Ile Leu Lys Glu Val Ser Ser Leu Glu Val Glu Glu Lys Lys
    1385                1390                1395

Leu Glu Glu Val His Glu Leu Lys Glu Glu Val Glu His Ile Ile
    1400                1405                1410

Ser Gly Asp Ala His Ile Lys Gly Leu Glu Glu Asp Asp Leu Glu
    1415                1420                1425

Glu Val Asp Asp Leu Lys Gly Ser Ile Leu Asp Met Leu Lys Gly
    1430                1435                1440

Asp Met Glu Leu Gly Asp Met Asp Lys Glu Ser Leu Glu Asp Val
    1445                1450                1455

Thr Thr Lys Leu Gly Glu Arg Val Glu Ser Leu Lys Asp Val Leu
    1460                1465                1470

Ser Ser Ala Leu Gly Met Asp Glu Glu Gln Met Lys Thr Arg Lys
    1475                1480                1485

Lys Ala Gln Arg Pro Lys Leu Glu Glu Val Leu Leu Lys Glu Glu
    1490                1495                1500

Val Lys Glu Glu Pro Lys Lys Lys Ile Thr Lys Lys Val Arg
    1505                1510                1515

Phe Asp Ile Lys Asp Lys Glu Pro Lys Asp Glu Ile Val Glu Val
    1520                1525                1530

Glu Met Lys Asp Glu Asp Ile Glu Glu Asp Val Glu Glu Asp Ile
    1535                1540                1545

Glu Glu Asp Ile Glu Glu Asp Lys Val Glu Asp Ile Asp Glu Asp
    1550                1555                1560

Ile Asp Glu Asp Ile Gly Glu Asp Lys Asp Glu Val Ile Asp Leu
    1565                1570                1575

Ile Val Gln Lys Glu Lys Arg Ile Glu Lys Val Lys Ala Lys Lys
    1580                1585                1590

Lys Lys Leu Glu Lys Lys Val Glu Glu Gly Val Ser Gly Leu Lys
    1595                1600                1605

Lys His Val Asp Glu Val Met Lys Tyr Val Gln Lys Ile Asp Lys
    1610                1615                1620

Glu Val Asp Lys Glu Val Ser Lys Ala Leu Glu Ser Lys Asn Asp
    1625                1630                1635

Val Thr Asn Val Leu Lys Gln Asn Gln Asp Phe Phe Ser Lys Val
    1640                1645                1650

Lys Asn Phe Val Lys Lys Tyr Lys Val Phe Ala Ala Pro Phe Ile
    1655                1660                1665

Ser Ala Val Ala Ala Phe Ser Tyr Val Val Gly Phe Phe Thr
    1670                1675                1680

Phe Ser Leu Phe Ser Ser Cys Val Thr Ile Ala Ser Ser Thr Tyr
    1685                1690                1695

Leu Leu Ser Lys Val Asp Lys Thr Ile Asn Lys Asn Lys Glu Arg
    1700                1705                1710
```

```
Pro Phe Tyr Ser Phe Val Phe Asp Ile Phe Lys Asn  Leu Lys His
    1715            1720            1725

Tyr Leu Gln Gln Met Lys Glu Lys Phe Ser Lys Glu  Lys Asn Asn
    1730            1735            1740

Asn Val Ile Glu Val Thr Asn Lys Ala Glu Lys Lys  Gly Asn Val
    1745            1750            1755

Gln Val Thr Asn Lys Thr Glu Lys Thr Thr Lys Val  Asp Lys Asn
    1760            1765            1770

Asn Lys Val Pro Lys Lys Arg Arg Thr Gln Lys Ser  Lys
    1775            1780            1785

<210> SEQ ID NO 4
<211> LENGTH: 1891
<212> TYPE: DNA
<213> ORGANISM: P. falciparum
<220> FEATURE:
<221> NAME/KEY: CDS
<222> LOCATION: (2)..(1891)
<223> OTHER INFORMATION:

<400> SEQUENCE: 4 t aca tta act gaa agt gta gat gat aat aaa aat tta gaa gaa gcc gaa          49
  Thr Leu Thr Glu Ser Val Asp Asp Asn Lys Asn Leu Glu Glu Ala Glu
  1               5                   10                  15 gat ata aag gaa aat atc tta tta agt aat ata gaa gaa cca aaa gaa            97
Asp Ile Lys Glu Asn Ile Leu Leu Ser Asn Ile Glu Glu Pro Lys Glu
            20                  25                  30 aat att att gac aat tta tta aat aat att gga caa aat tca gaa aaa          145
Asn Ile Ile Asp Asn Leu Leu Asn Asn Ile Gly Gln Asn Ser Glu Lys
        35                  40                  45 caa gaa agt gta tca gaa aat gta caa gtc agt gat gaa ctt ttt aat          193
Gln Glu Ser Val Ser Glu Asn Val Gln Val Ser Asp Glu Leu Phe Asn
    50                  55                  60 gaa tta tta aat agt gta gat gtt aat gga gaa gta aaa gaa aat att          241
Glu Leu Leu Asn Ser Val Asp Val Asn Gly Glu Val Lys Glu Asn Ile
65                  70                  75                  80 ttg gag gaa agt caa gtt aat gac gat att ttt aat agt tta gta aaa          289
Leu Glu Glu Ser Gln Val Asn Asp Asp Ile Phe Asn Ser Leu Val Lys
                85                  90                  95 agt gtt caa caa gaa caa caa cac aat gtt gaa gaa aaa gtt gaa gaa          337
Ser Val Gln Gln Glu Gln Gln His Asn Val Glu Glu Lys Val Glu Glu
            100                 105                 110 agt gta gaa gaa aat gac gaa gaa agt gta gaa gaa aat gta gaa gaa          385
Ser Val Glu Glu Asn Asp Glu Glu Ser Val Glu Glu Asn Val Glu Glu
        115                 120                 125 aat gta gaa gaa aat gac gac gga agt gta gcc tca agt gtt gaa gaa          433
Asn Val Glu Glu Asn Asp Asp Gly Ser Val Ala Ser Ser Val Glu Glu
    130                 135                 140 agt ata gct tca agt gtt gat gaa agt ata gat tca agt att gaa gaa          481
Ser Ile Ala Ser Ser Val Asp Glu Ser Ile Asp Ser Ser Ile Glu Glu
145                 150                 155                 160 aat gta gct cca act gtt gaa gaa atc gta gct cca act gtt gaa gaa          529
Asn Val Ala Pro Thr Val Glu Glu Ile Val Ala Pro Thr Val Glu Glu
                165                 170                 175 att gta gct cca agt gtt gta gaa agt gtg gct cca agt gtt gaa gaa          577
Ile Val Ala Pro Ser Val Val Glu Ser Val Ala Pro Ser Val Glu Glu
            180                 185                 190 agt gta gct cca agt gtt gaa gaa agt gta gct gaa aat gtt gaa gaa          625
Ser Val Ala Pro Ser Val Glu Glu Ser Val Ala Glu Asn Val Glu Glu
        195                 200                 205
```

-continued

| | |
|---|---|
| agt gta gct gaa aat gtt gaa gaa atc gta gct cca agt gtt gaa gaa<br>Ser Val Ala Glu Asn Val Glu Glu Ile Val Ala Pro Ser Val Glu Glu<br>210               215               220 | 673 |
| agt gta gct gaa aat gtt gaa gaa agt gta gct gaa aat gtt gaa gaa<br>Ser Val Ala Glu Asn Val Glu Glu Ser Val Ala Glu Asn Val Glu Glu<br>225         230              235               240 | 721 |
| agt gta gct gaa aat gtt gaa gaa agt gta gct gaa aat gtt gaa gaa<br>Ser Val Ala Glu Asn Val Glu Glu Ser Val Ala Glu Asn Val Glu Glu<br>              245               250               255 | 769 |
| agt gta gct gaa aat gtt gaa gaa atc gta gct cca act gtt gaa gaa<br>Ser Val Ala Glu Asn Val Glu Glu Ile Val Ala Pro Thr Val Glu Glu<br>260               265               270 | 817 |
| agt gta gct cca act gtt gaa gaa att gta gct cca act gtt gaa gaa<br>Ser Val Ala Pro Thr Val Glu Glu Ile Val Ala Pro Thr Val Glu Glu<br>275               280               285 | 865 |
| agt gta gct cca act gtt gaa gaa att gta gtt cca agt gtt gaa gaa<br>Ser Val Ala Pro Thr Val Glu Glu Ile Val Val Pro Ser Val Glu Glu<br>290               295               300 | 913 |
| agt gta gct cca agt gtt gaa gaa agt gta gct gaa aat gtt gaa gaa<br>Ser Val Ala Pro Ser Val Glu Glu Ser Val Ala Glu Asn Val Glu Glu<br>305               310              315               320 | 961 |
| agt gta gct gaa aat gtt gaa gaa agt gta gct gaa aat gtt gaa gaa<br>Ser Val Ala Glu Asn Val Glu Glu Ser Val Ala Glu Asn Val Glu Glu<br>              325               330               335 | 1009 |
| agt gta gct gaa aat gtt gaa gaa agt gta gct gaa aat gtt gaa gaa<br>Ser Val Ala Glu Asn Val Glu Glu Ser Val Ala Glu Asn Val Glu Glu<br>340               345               350 | 1057 |
| atc gta gct cca agt gtt gaa gaa atc gta gct cca act gtt gaa gaa<br>Ile Val Ala Pro Ser Val Glu Glu Ile Val Ala Pro Thr Val Glu Glu<br>355               360               365 | 1105 |
| agt gtt gct gaa aac gtt gca aca aat tta tca gac aat ctt tta agt<br>Ser Val Ala Glu Asn Val Ala Thr Asn Leu Ser Asp Asn Leu Leu Ser<br>370               375               380 | 1153 |
| aat tta tta ggt ggt atc gaa act gag gaa ata aag gac agt ata tta<br>Asn Leu Leu Gly Gly Ile Glu Thr Glu Glu Ile Lys Asp Ser Ile Leu<br>385               390              395               400 | 1201 |
| aat gag ata gaa gaa gta aaa gaa aat gta gtc acc aca ata cta gaa<br>Asn Glu Ile Glu Glu Val Lys Glu Asn Val Val Thr Thr Ile Leu Glu<br>              405               410               415 | 1249 |
| aaa gta gaa gaa act aca gct gaa agt gta act act ttt agt aat ata<br>Lys Val Glu Glu Thr Thr Ala Glu Ser Val Thr Thr Phe Ser Asn Ile<br>420               425               430 | 1297 |
| tta gag gag ata caa gaa aat act att act aat gat act ata gag gaa<br>Leu Glu Glu Ile Gln Glu Asn Thr Ile Thr Asn Asp Thr Ile Glu Glu<br>              435               440               445 | 1345 |
| aaa tta gaa gaa ctc cac gaa aat gta tta agt gcc gct tta gaa aat<br>Lys Leu Glu Glu Leu His Glu Asn Val Leu Ser Ala Ala Leu Glu Asn<br>450               455               460 | 1393 |
| acc caa agt gaa gag gaa aag aaa gaa gta ata gat gta att gaa gaa<br>Thr Gln Ser Glu Glu Glu Lys Lys Glu Val Ile Asp Val Ile Glu Glu<br>465               470              475               480 | 1441 |
| gta aaa gaa gag gtc gct acc act tta ata gaa act gtg gaa cag gca<br>Val Lys Glu Glu Val Ala Thr Thr Leu Ile Glu Thr Val Glu Gln Ala<br>              485               490               495 | 1489 |
| gaa gaa gag agc gaa agt aca att acg gaa ata ttt gaa aat tta gaa<br>Glu Glu Glu Ser Glu Ser Thr Ile Thr Glu Ile Phe Glu Asn Leu Glu<br>              500               505               510 | 1537 |
| gaa aat gca gta gaa agt aat gaa aaa gtt gca gag aat tta gag aaa<br>Glu Asn Ala Val Glu Ser Asn Glu Lys Val Ala Glu Asn Leu Glu Lys | 1585 |

-continued

```
                 515                 520                 525
tta aac gaa act gta ttt aat act gta tta gat aaa gta gag gaa aca    1633
Leu Asn Glu Thr Val Phe Asn Thr Val Leu Asp Lys Val Glu Glu Thr
        530                 535                 540 gta gaa att agc gga gaa agt tta gaa aac aat gaa atg gat aaa gca    1681
Val Glu Ile Ser Gly Glu Ser Leu Glu Asn Asn Glu Met Asp Lys Ala
545                 550                 555                 560 ttt ttt agt gaa ata ttt gat aat gta aaa gga ata caa gaa aat tta    1729
Phe Phe Ser Glu Ile Phe Asp Asn Val Lys Gly Ile Gln Glu Asn Leu
                565                 570                 575 tta aca ggt atg ttt cga agt ata gaa acc agt ata gta atc caa tca    1777
Leu Thr Gly Met Phe Arg Ser Ile Glu Thr Ser Ile Val Ile Gln Ser
            580                 585                 590 gaa gaa aag gtt gat ttg aat gaa aat gtg gtt agt tcg att tta gat    1825
Glu Glu Lys Val Asp Leu Asn Glu Asn Val Val Ser Ser Ile Leu Asp
        595                 600                 605 aat ata gaa aat atg aaa gaa ggt tta tta aat aaa tta gaa aat att    1873
Asn Ile Glu Asn Met Lys Glu Gly Leu Leu Asn Lys Leu Glu Asn Ile
610                 615                 620 tca agt act gaa ggc gaa                                            1891
Ser Ser Thr Glu Gly Glu
625             630

<210> SEQ ID NO 5
<211> LENGTH: 630
<212> TYPE: PRT
<213> ORGANISM: P. falciparum

<400> SEQUENCE: 5

Thr Leu Thr Glu Ser Val Asp Asp Asn Lys Asn Leu Glu Glu Ala Glu
1               5                   10                  15

Asp Ile Lys Glu Asn Ile Leu Leu Ser Asn Ile Glu Glu Pro Lys Glu
            20                  25                  30

Asn Ile Ile Asp Asn Leu Leu Asn Asn Ile Gly Gln Asn Ser Glu Lys
        35                  40                  45

Gln Glu Ser Val Ser Glu Asn Val Gln Val Ser Asp Glu Leu Phe Asn
    50                  55                  60

Glu Leu Leu Asn Ser Val Asp Val Asn Gly Glu Val Lys Glu Asn Ile
65                  70                  75                  80

Leu Glu Glu Ser Gln Val Asn Asp Asp Ile Phe Asn Ser Leu Val Lys
                85                  90                  95

Ser Val Gln Gln Glu Gln Gln His Asn Val Glu Lys Val Glu Glu
            100                 105                 110

Ser Val Glu Glu Asn Asp Glu Glu Ser Val Glu Glu Asn Val Glu Glu
        115                 120                 125

Asn Val Glu Glu Asn Asp Asp Gly Ser Val Ala Ser Ser Val Glu Glu
    130                 135                 140

Ser Ile Ala Ser Ser Val Asp Glu Ser Ile Asp Ser Ser Ile Glu Glu
145                 150                 155                 160

Asn Val Ala Pro Thr Val Glu Glu Ile Val Ala Pro Thr Val Glu Glu
                165                 170                 175

Ile Val Ala Pro Ser Val Glu Ser Val Ala Pro Ser Val Glu Glu
            180                 185                 190

Ser Val Ala Pro Ser Val Glu Glu Ser Val Ala Glu Asn Val Glu Glu
        195                 200                 205

Ser Val Ala Glu Asn Val Glu Glu Ile Val Ala Pro Ser Val Glu Glu
    210                 215                 220
```

```
Ser Val Ala Glu Asn Val Glu Ser Val Ala Glu Asn Val Glu Glu
225                 230                 235                 240

Ser Val Ala Glu Asn Val Glu Ser Val Ala Glu Asn Val Glu Glu
                245                 250                 255

Ser Val Ala Glu Asn Val Glu Ile Val Ala Pro Thr Val Glu Glu
                260                 265                 270

Ser Val Ala Pro Thr Val Glu Glu Ile Val Ala Pro Thr Val Glu Glu
            275                 280                 285

Ser Val Ala Pro Thr Val Glu Glu Ile Val Val Pro Ser Val Glu Glu
            290                 295                 300

Ser Val Ala Pro Ser Val Glu Glu Ser Val Ala Glu Asn Val Glu Glu
305                 310                 315                 320

Ser Val Ala Glu Asn Val Glu Glu Ser Val Ala Glu Asn Val Glu Glu
                325                 330                 335

Ser Val Ala Glu Asn Val Glu Glu Ser Val Ala Glu Asn Val Glu Glu
                340                 345                 350

Ile Val Ala Pro Ser Val Glu Glu Ile Val Ala Pro Thr Val Glu Glu
                355                 360                 365

Ser Val Ala Glu Asn Val Ala Thr Asn Leu Ser Asp Asn Leu Leu Ser
370                 375                 380

Asn Leu Leu Gly Gly Ile Glu Thr Glu Glu Ile Lys Asp Ser Ile Leu
385                 390                 395                 400

Asn Glu Ile Glu Glu Val Lys Glu Asn Val Val Thr Thr Ile Leu Glu
                405                 410                 415

Lys Val Glu Glu Thr Thr Ala Glu Ser Val Thr Thr Phe Ser Asn Ile
                420                 425                 430

Leu Glu Glu Ile Gln Glu Asn Thr Ile Thr Asn Asp Thr Ile Glu Glu
            435                 440                 445

Lys Leu Glu Glu Leu His Glu Asn Val Leu Ser Ala Ala Leu Glu Asn
450                 455                 460

Thr Gln Ser Glu Glu Lys Lys Glu Val Ile Asp Val Ile Glu Glu
465                 470                 475             480

Val Lys Glu Glu Val Ala Thr Thr Leu Ile Glu Thr Val Glu Gln Ala
                485                 490                 495

Glu Glu Glu Ser Glu Ser Thr Ile Thr Glu Ile Phe Glu Asn Leu Glu
                500                 505                 510

Glu Asn Ala Val Glu Ser Asn Glu Lys Val Ala Glu Asn Leu Glu Lys
            515                 520                 525

Leu Asn Glu Thr Val Phe Asn Thr Val Leu Asp Lys Val Glu Glu Thr
530                 535                 540

Val Glu Ile Ser Gly Glu Ser Leu Glu Asn Asn Glu Met Asp Lys Ala
545                 550                 555                 560

Phe Phe Ser Glu Ile Phe Asp Asn Val Lys Gly Ile Gln Glu Asn Leu
                565                 570                 575

Leu Thr Gly Met Phe Arg Ser Ile Glu Thr Ser Ile Val Ile Gln Ser
                580                 585                 590

Glu Glu Lys Val Asp Leu Asn Glu Asn Val Val Ser Ser Ile Leu Asp
                595                 600                 605

Asn Ile Glu Asn Met Lys Glu Gly Leu Leu Asn Lys Leu Glu Asn Ile
                610                 615                 620

Ser Ser Thr Glu Gly Glu
625                 630
```

<210> SEQ ID NO 6
<211> LENGTH: 28
<212> TYPE: DNA
<213> ORGANISM: Artificial Sequence
<220> FEATURE:
<223> OTHER INFORMATION: Synthetic DNA

<400> SEQUENCE: 6
gtgatgaact ttttaatgaa ttattaaa                                28

<210> SEQ ID NO 7
<211> LENGTH: 29
<212> TYPE: DNA
<213> ORGANISM: Artificial Sequence
<220> FEATURE:
<223> OTHER INFORMATION: Synthetic DNA

<400> SEQUENCE: 7
tgttgttctt gttgaacact ttttactaa                               29

<210> SEQ ID NO 8
<211> LENGTH: 25
<212> TYPE: DNA
<213> ORGANISM: Artificial Sequence
<220> FEATURE:
<223> OTHER INFORMATION: Synthetic DNA

<400> SEQUENCE: 8
ggtatcgaaa ctgaggaaat aaagg                                   25

<210> SEQ ID NO 9
<211> LENGTH: 24
<212> TYPE: DNA
<213> ORGANISM: Artificial Sequence
<220> FEATURE:
<223> OTHER INFORMATION: Synthetic DNA

<400> SEQUENCE: 9
catagcagga acatcaacat ccac                                    24

<210> SEQ ID NO 10
<211> LENGTH: 50
<212> TYPE: PRT
<213> ORGANISM: Artificial Sequence
<220> FEATURE:
<223> OTHER INFORMATION: Synthetic Peptide

<400> SEQUENCE: 10

Arg Asp Glu Leu Phe Asn Glu Leu Leu Asn Ser Val Asp Val Asn Gly
1               5                   10                  15

Glu Val Lys Glu Asn Ile Leu Glu Glu Ser Gln Val Asn Asp Asp Ile
            20                  25                  30

Phe Asn Ser Leu Val Lys Ser Val Gln Gln Glu Gln Gln His Asn Val
        35                  40                  45

Glu Glu
    50

<210> SEQ ID NO 11
<211> LENGTH: 100
<212> TYPE: PRT
<213> ORGANISM: Artificial Sequence
<220> FEATURE:
<223> OTHER INFORMATION: Synthetic Peptide

<400> SEQUENCE: 11

```
Val Glu Glu Ser Val Glu Glu Asn Asp Glu Glu Ser Val Glu Glu Asn
1               5                   10                  15

Val Glu Glu Asn Val Glu Asn Asn Asp Asp Gly Ser Val Ala Ser Ser
                20                  25                  30

Val Glu Glu Ser Ile Ala Ser Ser Val Asp Glu Ser Ile Asp Ser Ser
            35                  40                  45

Ile Glu Glu Asn Val Ala Pro Thr Val Glu Glu Ile Val Ala Pro Thr
        50                  55                  60

Val Glu Glu Ile Val Ala Pro Ser Val Val Lys Cys Ala Pro Ser
65                  70                  75                  80

Val Glu Glu Ser Val Ala Pro Ser Val Glu Glu Ser Val Ala Glu Met
                85                  90                  95

Leu Lys Glu Arg
            100

<210> SEQ ID NO 12
<211> LENGTH: 47
<212> TYPE: PRT
<213> ORGANISM: Artificial Sequence
<220> FEATURE:
<223> OTHER INFORMATION: Synthetic Peptide

<400> SEQUENCE: 12

Arg Asp Glu Leu Phe Asn Glu Leu Leu Asn Ser Val Asp Val Asn Gly
1               5                   10                  15

Glu Val Lys Glu Asn Ile Leu Glu Glu Ser Gln Val Asn Asp Asp Ile
                20                  25                  30

Phe Asn Ser Leu Val Lys Ser Val Gln Gln Glu Gln Gln His Asn
            35                  40                  45

<210> SEQ ID NO 13
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 13

Asp Glu Leu Phe Asn Glu Leu Leu Asn Ser Val Asp Val Asn Gly Glu
1               5                   10                  15

Val Lys Glu Asn Ile Leu Glu Glu Ser Gln
                20                  25

<210> SEQ ID NO 14
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 14

Leu Glu Glu Ser Gln Val Asn Asp Asp Ile Phe Ser Asn Ser Leu Val
1               5                   10                  15

Lys Ser Val Gln Gln Glu Gln Gln His Asn Val
                20                  25

<210> SEQ ID NO 15
<211> LENGTH: 28
<212> TYPE: PRT
<213> ORGANISM: Artificial Sequence
<220> FEATURE:
```

<223> OTHER INFORMATION: Synthetic Peptide

<400> SEQUENCE: 15

Val Glu Ser Val Ala Pro Ser Val Glu Glu Ser Val Ala Pro Ser Val
1               5                   10                  15
Glu Glu Ser Val Ala Glu Asn Val Glu Glu Ser Val
            20                  25

<210> SEQ ID NO 16
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 16

Leu Leu Ser Asn Ile Glu Glu Pro Lys Glu Asn Ile Ile Asp Asn Leu
1               5                   10                  15
Leu Asn Asn Ile
            20

<210> SEQ ID NO 17
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 17

Val Glu Glu Ser
1

<210> SEQ ID NO 18
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 18

Val Glu Glu Asn
1

<210> SEQ ID NO 19
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 19

Val Glu Glu Ile
1

<210> SEQ ID NO 20
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 20

Val Ala Pro Ser
1

<210> SEQ ID NO 21
<211> LENGTH: 56
<212> TYPE: PRT
<213> ORGANISM: Artificial Sequence
<220> FEATURE:
<223> OTHER INFORMATION: Synthetic Peptide

<400> SEQUENCE: 21

```
Val Glu Glu Lys Val Glu Glu Ser Val Glu Glu Asn Asp Glu Glu Ser
1               5                   10                  15

Val Glu Glu Asn Val Glu Glu Asn Val Glu Glu Asn Asp Asp Gly Ser
                20                  25                  30

Val Ala Ser Ser Val Glu Glu Ser Ile Ala Ser Ser Val Asp Glu Ser
            35                  40                  45

Ile Asp Ser Ser Ile Glu Glu Asn
        50                  55
```

<210> SEQ ID NO 22
<211> LENGTH: 540
<212> TYPE: PRT
<213> ORGANISM: Artificial Sequence
<220> FEATURE:
<223> OTHER INFORMATION: Synthetic Peptide

<400> SEQUENCE: 22

```
Val Ala Pro Thr Val Glu Glu Ile Val Ala Pro Ser Val Val Glu Ser
1               5                   10                  15

Val Ala Pro Ser Val Glu Glu Ser Val Glu Glu Asn Val Glu Glu Ser
                20                  25                  30

Val Ala Glu Asn Val Glu Glu Ser Val Ala Glu Asn Val Glu Glu Ser
            35                  40                  45

Val Ala Glu Asn Val Glu Glu Ser Val Ala Glu Asn Val Glu Glu Ile
        50                  55                  60

Val Ala Pro Thr Val Glu Glu Ile Val Ala Pro Thr Val Glu Glu Ile
65                  70                  75                  80

Val Ala Pro Ser Val Val Glu Ser Val Ala Pro Ser Val Glu Glu Ser
                85                  90                  95

Val Glu Glu Asn Val Glu Glu Ser Val Ala Glu Asn Val Glu Glu Ser
            100                 105                 110

Val Ala Glu Asn Val Glu Glu Ser Val Ala Glu Asn Val Glu Glu Ser
        115                 120                 125

Val Ala Glu Asn Val Glu Glu Ser Val Ala Glu Asn Val Glu Glu Ile
    130                 135                 140

Val Ala Pro Thr Val Glu Glu Ile Val Ala Pro Thr Val Glu Glu Ile
145                 150                 155                 160

Val Ala Pro Ser Val Val Glu Ser Val Ala Pro Ser Val Glu Glu Ser
                165                 170                 175

Val Glu Glu Asn Val Glu Glu Ser Val Ala Glu Asn Val Glu Glu Ser
            180                 185                 190

Val Ala Glu Asn Val Glu Glu Ser Val Ala Glu Asn Val Glu Glu Ser
        195                 200                 205

Val Ala Glu Asn Val Glu Glu Ser Val Ala Glu Asn Val Glu Glu Ser
    210                 215                 220

Val Ala Glu Asn Val Glu Glu Ser Val Ala Glu Asn Val Glu Glu Ile
225                 230                 235                 240

Val Ala Pro Thr Val Glu Glu Ile Val Ala Pro Thr Val Glu Glu Ile
                245                 250                 255
```

-continued

Val Ala Pro Ser Val Glu Ser Val Ala Pro Ser Val Glu Glu Ser
                260                 265                 270

Val Glu Glu Asn Val Glu Ser Val Ala Glu Asn Val Glu Glu Ser
            275                 280                 285

Val Ala Glu Asn Val Glu Ser Val Ala Glu Asn Val Glu Glu Ser
            290                 295                 300

Val Ala Glu Asn Val Glu Ile Val Ala Pro Thr Val Glu Glu Ile
305                 310                 315                 320

Val Ala Pro Thr Val Glu Ile Val Ala Pro Ser Val Val Glu Ser
                325                 330                 335

Val Ala Pro Ser Val Glu Ser Val Glu Glu Asn Val Glu Glu Ser
                340                 345                 350

Val Ala Glu Asn Val Glu Ser Val Ala Glu Asn Val Glu Glu Ser
            355                 360                 365

Val Ala Glu Asn Val Glu Ile Val Ala Pro Thr Val Glu Glu Ile
            370                 375                 380

Val Ala Pro Thr Val Glu Ile Val Ala Pro Ser Val Val Glu Ser
385                 390                 395                 400

Val Ala Pro Ser Val Glu Glu Ser Val Glu Glu Asn Val Glu Glu Ser
                405                 410                 415

Val Ala Glu Asn Val Glu Ser Val Ala Glu Asn Val Glu Glu Ser
            420                 425                 430

Val Ala Glu Asn Val Glu Ser Val Ala Glu Asn Val Glu Glu Ile
            435                 440                 445

Val Ala Pro Thr Val Glu Ile Val Ala Pro Thr Val Glu Glu Ile
            450                 455                 460

Val Ala Pro Ser Val Val Glu Ser Val Ala Pro Ser Val Glu Glu Ser
465                 470                 475                 480

Val Glu Glu Asn Val Glu Ser Val Ala Glu Asn Val Glu Glu Ser
                485                 490                 495

Val Ala Glu Asn Val Glu Ser Val Ala Glu Asn Val Glu Glu Ser
            500                 505                 510

Val Ala Pro Thr Val Glu Glu Ile Val Ala Pro Ser Val Glu Glu Ser
            515                 520                 525

Val Ala Pro Ser Val Glu Glu Ser Val Ala Glu Asn
                530                 535                 540

<210> SEQ ID NO 23
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 23

Asp Glu Asp Ile Glu Glu Asp Val Glu Glu Asp Ile Glu Glu Asp Ile
1               5                   10                  15

Glu Glu Asp Lys Val Glu Asp Ile Asp Glu Ile Asp Glu Asp Ile
            20                  25                  30

Gly Glu Asp Lys Asp Glu Val
        35

<210> SEQ ID NO 24
<211> LENGTH: 56
<212> TYPE: PRT
<213> ORGANISM: Artificial Sequence
<220> FEATURE:

<223> OTHER INFORMATION: Synthetic Peptide

<400> SEQUENCE: 24

Val Glu Glu Lys Val Glu Glu Ser Val Glu Glu Asn Asp Glu Glu Ser
1               5                   10                  15

Val Glu Glu Asn Val Glu Glu Asn Val Glu Glu Asn Asp Asp Gly Ser
            20                  25                  30

Val Ala Ser Ser Val Glu Glu Ser Ile Ala Ser Ser Val Asp Glu Ser
        35                  40                  45

Ile Asp Ser Ser Ile Glu Glu Asn
    50                  55

<210> SEQ ID NO 25
<211> LENGTH: 212
<212> TYPE: PRT
<213> ORGANISM: Artificial Sequence
<220> FEATURE:
<223> OTHER INFORMATION: Synthetic Peptide

<400> SEQUENCE: 25

Val Ala Pro Thr Val Glu Glu Ile Val Ala Pro Thr Val Glu Glu Ile
1               5                   10                  15

Val Ala Pro Ser Val Glu Ser Val Ala Pro Ser Val Glu Glu Ser
            20                  25                  30

Val Ala Pro Ser Val Glu Ser Val Ala Glu Asn Val Glu Glu Ser
        35                  40                  45

Val Ala Glu Asn Val Glu Ile Val Ala Pro Ser Val Glu Glu Ser
    50                  55                  60

Val Ala Glu Asn Val Glu Glu Ser Val Ala Glu Asn Val Glu Glu Ser
65                  70                  75                  80

Val Ala Glu Asn Val Glu Glu Ser Val Ala Glu Asn Val Glu Glu Ser
                85                  90                  95

Val Ala Glu Asn Val Glu Glu Ile Val Ala Pro Thr Val Glu Glu Ser
                100                 105                 110

Val Ala Pro Thr Val Glu Glu Ile Val Ala Pro Thr Val Glu Glu Ser
        115                 120                 125

Val Ala Pro Thr Val Glu Glu Ile Val Val Pro Ser Val Glu Glu Ser
    130                 135                 140

Val Ala Pro Ser Val Glu Glu Ser Val Ala Glu Asn Val Glu Glu Ser
145                 150                 155                 160

Val Ala Glu Asn Val Glu Glu Ser Val Ala Glu Asn Val Glu Glu Ser
                165                 170                 175

Val Ala Glu Asn Val Glu Glu Ser Val Ala Glu Asn Val Glu Glu Ile
                180                 185                 190

Val Ala Pro Ser Val Glu Glu Ile Val Ala Pro Thr Val Glu Glu Ser
        195                 200                 205

Val Ala Glu Asn
    210

<210> SEQ ID NO 26
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 26

Val Val Glu Ser

```
<210> SEQ ID NO 27
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 27

Val Ala Glu Asn
1

<210> SEQ ID NO 28
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 28

Val Ala Pro Thr
1

<210> SEQ ID NO 29
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 29

Val Val Pro Ser
1
```

MALARIAL PRE-ERYTHROCYTIC STAGE POLYPEPTIDE MOLECULES

This application is a Divisional of U.S. application Ser. No. 08/973,462, filed on Feb. 6, 1998, now allowed as U.S. Pat. No. 6,191,270, which is a 371 of PCT/FR96/00894, filed Jun. 12, 1996.

The parasites responsible for malaria in man display different morphologies in the human host and express different antigens depending on their location in the body. The morphological and antigenic differences of these parasites during their life cycles in man enable different stages of development in the liver and in the blood to be defined: the sporozoite, the infectious form injected by the vector mosquito, transforms rapidly into a schizont in the host's hepatocytes and thereafter infects the erythrocytes. The intrahepatic localization of $P.$ $falciparum$ manifests itself in the expression of a group of antigens specific to this stage of development and which are highly immunogenic under the natural conditions of exposure to the disease. This clinically silent phase is at present the only one against which a very strong, sterilizing immunity can be induced experimentally in man, by injecting irradiated sporozoites capable of entering the hepatocyte and of developing therein but without being able to lead on to the blood stage of the disease. Accordingly, the inventors have concentrated the bulk of their efforts on these two pre-erythrocytic stages. However, these stages are also the most intricate ones to study, and hence the least understood, since it is difficult or even impossible to obtain biological material, the only in vitro study model affords a very low yield and the best animal model remains the chimpanzee, the use of which is limited and expensive.

In order to gain access to the antigens of the pre-erythrocytic stages, the inventors used sera of individuals who had resided for 25 years in a region where the disease is endemic but who were on permanent prophylaxis with chloroquine. These individuals were regularly subjected to infected mosquito bites but did not develop any complete blood infection. Their serum hence contained antibodies directed essentially against the pre-erythrocytic stages, which was verified by immunofluorescence (IF) and western blotting on the 3 stages of the parasite.

The use of these sera for screening a library of genomic DNA of the parasitic clone of $P.$ $falciparum$, the library being constructed in expression vectors in a phage lambda gt11 (V. Rosario, Science 212, 1981, pp. 1037–1038; and Thaithong et al., Transactions of Royal Society of Tropical Medicine and Hygiene, 1984, 78:242–245), led to the demonstration of polypeptides of the pre-erythrocytic stage, in particular the SALSA (sporozoite liver stage antigen) polypeptides described in EP A-0,407,230 and LSA-1 (liver stage antigen) described in WO 92/13884. The present invention relates to new polypeptide molecules specific to the pre-erythrocytic stage, and to their use as active principle of antimalarial vaccine or in methods of diagnosis of the disease.

The invention is the outcome of the demonstration by the inventors of the special properties of a particular antigen referred to as LSA-3 and of its fragments, which are seen to be candidates with a strong potential for producing an antimalarial vaccine, for the following reasons:

a) when a fraction of LSA-3 was used in combination with another antigen of the same stage of development of the parasite, such as LSA-1, to immunize chimpanzees, the animal responding to both molecules or only to LSA-3 displays the feature of not having parasites in the blood, of having a substantial decrease of the parasites in the liver and of manifesting a substantial recruitment of mononuclear cells indicating a response in terms of cellular immunity;

b) in regions where the disease is endemic, a very clear correlation is observed between the protection of individuals against natural infection by sporozoites and their responses in terms of antibodies against LSA-3;

c) in eight human volunteers immunized by injection of irradiated sporozoites, antibodies directed against LSA-3 are found in each of the four individuals resisting sporozoite infection and in none of the other four volunteers who developed a blood infection;

d) antibodies obtained against the peptide DG729 in WO 92/13884, already described, give a cross-reaction with the sporozoite and liver stages of the murine parasite $P.yoelii$, which permits a significant exploitation of the mouse model. In vitro, the human antibodies immunopurified on DG729 are capable, even at very low concentrations, of blocking the entry of $P.yoelii$ sporozoites into mouse hepatocytes. In vivo, mice immunized with DG729 are fully or partially protected against infection by $P.yoelii$ sporozoites;

e) lastly, some epitopes, in particular in the non-repeat portions of the molecule, stimulate the secretion of interferon-$\gamma$ by monocytes, this mediator enabling the intrahepatic development of the parasite to be inhibited (S. Mellouk et al., The Jour. Of Immun. 139, 4192–4195, 1987);

f) the sequence of the region of LSA-3 corresponding to a (lipo)peptide NR2 was analysed in 27 samples: 4 laboratory strains (NF54, K1, Palo Alto, T9/96), 3 Madagascan isolates, 3 Burmese isolates, 5 Brazilian isolates, 7 isolates from the Ivory Coast and 5 Thai isolates. No mutation was observed on the 300 base pairs analysed, that is to say 100% conservation in this immunologically important region containing one or more B, Th and CTL epitopes;

g) information about the structure of the antigen, and in particular of a peptide RE, and more especially about the central repeat region from which the peptide RE was designed and which contains one or more major B epitopes, was obtained from the hydrophobic cluster plot of the sequence available in the clone T9/96 (630 amino acids) (Gaboriot et al., (1987): Hydrophobic cluster analysis: an efficient new way to compare and analyse amino acid sequences, FEBS Letters, 224: 149–155); this method predicts a very strong propensity for $\alpha$-helical organization. The repeat region displays remarkable regularity in the spacing of the valine and isoleucine residues, alternating with acid or proline residues. The arrangement of the hydrophobic groups at the surface of this helix is reminiscent of a hydrophobic border gradually shifting from one face of the helix to the other according to a constant general orientation along the molecule, and probably related to a coiled-coil structure or packaging as seen in FIG. 4$b$ which depicts the HCP (hydrophobic cluster plot) of the peptide sequence of the clone DG729;

h) after demonstrating that there was a very wide range of immune responses to the LSA-3 antigen, we analysed the capacity of the responder cells to localize around the parasites in the liver. In mice immunized with the recom binant antigens, intraportal injection of each of the peptides absorbed on 10 μm polystyrene beads enables an afflux of lymphocytes around the antigen (mimicking the parasite) to be visualized after 48 hours, followed on the 5th day by a substantial recruitment of cells belonging to the macrophage line.

All these properties, some of which will be demonstrated in detail in the experiments described later, show that the LSA-3 antigen displays both good antigenicity and good immunogenicity.

The inventors were able to confirm and define the specificity of the stages of expression of the molecule; in the sporozoites, this expression was confirmed by the surface immunofluorescence of several strains and isolates. In western blot (or immunoblot) analysis, the LSA-3 molecule appears as a protein of molecular weight 200,000 daltons. While the messenger RNAs of sporozoites could not be obtained in sufficient amounts for a northern blot analysis, reverse PCR experiments confirmed the expression of LSA-3 at this stage. In infected hepatocytes, LSA-3 is observed in the parasitophorous vacuole of the parasite by immunofluorescence using antibodies against the repeat and non-repeat regions of the protein, as well as by electron microscopy.

A fragment of LSA-3 designated 729S, as well as three peptides designated NRI and NRII included in the non-repeat portion and 729R included in the repeat portion, have been described in Application WO 92/13884. Nevertheless, this document does not mention the special properties mentioned above, or other fragments of LSA-3 which could be either longer or shorter, included or combined with these fragments, which might display especially advantageous properties for use in vaccines.

The subject of the invention is polypeptide molecules containing at least ten consecutive amino acids of the amino acid sequence shown in FIG. 2 and designated SEQ ID No. 2, and representing LSA-3, the following polypeptides being excluded:

[SEQ ID NO:10]
RDELFNELLNSVDVNGEVKENILEESQVNDDIFNSLVKSVQQEQQHNVEE

[SEQ ID NO:11]
VEESVEENDEESVEENVEENVENNDDGSVASSVEESIASSVDESIDSSIE-

ENVAPTVEEIVAPTVEEIVAPSVVEKCAPSVEESVAPSVEESVAEMLKER

[SEQ ID NO:12]
RDELFNELLNSVDVNGEVKENILEESQVNDDIFNSLVKSVQQEQQHN
(729S)

[SEQ ID NO:13]
DELFNELLNSVDVNGEVKENILEESQ, (NRI)

[SEQ ID NO:14]
LEESQVNDDIFSNSLVKSVQQEQQHNV, (NRII)

[SEQ ID NO:15]
VESVAPSVEESVAPSVEESVAENVEESV. (729RE)

Other molecules according to the invention contain at least 20 consecutive amino acids or at least 50.

This set of polypeptides and the LSA-3 molecule are, throughout hereinafter, "polypeptides of the invention".

The experimental results and the comparisons of non-repeat sequences between different *P.falciparum* isolates indicate the existence of at least 70% homology between equivalent antigens of the liver stage of the parasite. Thus any peptide molecule displaying at least 70% homology with any one of the molecules defined above forms part of the invention, as do those displaying at least 70% homology with the following sequence:

Leu Leu Ser Asn Ile Glu Glu Pro Lys Glu Asn Ile Ile Asp Asn Leu Leu Asn Asn Ile (CT1) [SEQ ID NO:16]

lying between amino acids 140 and 159 of K1 or 23 and 42 of T9/96.

Likewise forming part of the invention are the poly-peptide molecules displaying at least 70% homology with the sequence depicted in FIG. 3, which depicts a portion of LSA-3 in T9/96: the DNA of this *P.falciparum* isolate was digested with restriction enzymes, then cloned into lambda gt11 and thus enabled the gene library of this isolate, already described above, to be constituted.

Conjugates consisting of a polypeptide originating from LSA-3 linked covalently via a lysine bridge to saturated or unsaturated lipid residues also form part of the invention, more especially when the lipid residue is a palmitoyl or a palmityl or an oleyl. $C_{16}$ or $C_{18}$ residues were thus coupled via a lysine bridge to the peptides NRI, NRII, 729RE and CT1 already depicted above. The method of synthesis used for these conjugates is described in Bourgault, Journal of Immunology, 149, 3416 (1992) and Rouaix, Vaccine, 12, 1209 (1994).

The invention also covers immunogenic compositions containing at least one polypeptide molecule or one conjugate described above, as well as the vaccines containing these immunogenic compositions. Other immunogenic epitopes, in particular LSA-1, SALSA and STARP, have already been described in EP A-0407230 and in WO 92/13884. The vaccine compositions according to the invention can advantageously contain a mixture of immunogenic peptides originating from LSA-3 and of the peptides or antigens originating from LSA-1, SALSA or STARP; a more especially advantageous mixture could be the one consisting, on the one hand of NRI, NRII or whole LSA-3, these being coupled or otherwise to a lipid residue, and on the other hand the peptides SALSA-1, SALSA-2 or the SALSA antigen coupled or otherwise to a lipid residue.

All polypeptide molecules corresponding to the above definition and displaying at least 70% homology with the polypeptides LSA-3, CT1, NRI, NRII or 729RE may be combined in homologous or heterologous fashion with other peptide sequences or sequences originating from another antigen of the different stages of *P.falciparum.*

70% Homology of sequences should be clearly understood to refer to a sequence homology with respect to any one of the isolates whose sequence is known or capable of being known, and not an overall homology between the collective isolates. In effect, the central repeat region of LSA-3 (block 2 of FIG. 4) displays a variable number of repeat sequences responsible for a variability from one isolate to another, as seen, more-over, in the diagram of FIG. 4, in which the difference in length between the repeat portions of block 2 of the isolates T9/96 and K1 is blatant although the tetrapeptides which constitute this repeat region (VEES, VEEN, VEEI, VAPS, VAPT and the like) are very well conserved. In contrast, the repeat sequences of block 1 are fully conserved between the two isolates. Thus, bearing in mind the intrinsic variability of this block 2 from one isolate to another, the definition 70% homology applies to the LSA-3 antigen of the different isolates excluding the repeat sequences of block 2.

The invention also covers the polyclonal or monoclonal antibodies which specifically recognize the polypeptide molecules of the invention.

These molecules of the invention may be used for carrying out diagnostic methods and producing kits enabling the existence of *P.falciparum* infection to be detected; this method can be either an assay of circulating specific antibodies, by carrying out standard serological methods by bringing one of the above antigens into contact with a biological fluid of the individual in question, or methods of assay of antigens using polyclonal or monoclonal antibodies obtained by standard methods for obtaining such antibodies with the corresponding antigens. In the diagnostic outfits or kits of the invention, the reagents enabling the antigen/antibody complexes produced to be detected, which can also carry a label or be capable of being recognized in their turn by a labelled reagent, are present. Depending on whether it is desired to carry out an antigen test or a serological test, the kit comprises either the antibodies or the antigens of the invention.

The invention also covers all the nucleotide sequences coding for a polypeptide of the invention, as well as any recombinant nucleic acid containing at least one nucleotide sequence of the invention, inserted into a nucleic acid which is heterologous with respect to the said nucleotide sequence.

The nucleic acid sequences coding for LSA-3 or its immunogenic fragments and corresponding to one of the following definitions form part of the invention:
(a) the linked succession of nucleotides as depicted in SEQ ID No. 1 of FIG. 1, or
(b) the linked succession of nucleotides depicted in SEQ ID No. 2 of FIG. 2,
(c) a linked succession displaying at least 70% homology with that of FIG. 1 or of FIG. 2, or
(d) a linked succession of nucleotides which are complementary to those presented in (a), (b) or (c).

The expression "coding for LSA-3" is understood to refer both to the gene depicted in SEQ ID No. 1 of FIG. 1 and the cDNA depicted in SEQ ID No. 2 of FIG. 2.

The invention relates more especially to a recombinant nucleic acid in which the nucleotide sequence of the invention is preceded by a promoter (in particular an inducible promoter), under the control of which the transcription of the said sequence is capable of being performed, and, where appropriate, followed by a sequence coding for transcription termination signals.

The invention also covers the coding sequence originating from the clone T9/96 depicted in FIG. 3 by SEQ ID No. 4.

In this sequence, the fragment CT1 lies between nucleotides 67 and 126, the fragment 679 now at nucleotide 206 and the fragment 729RE lies between nucleotides 547 and 630.

Lastly, the invention covers any recombinant vector used especially for the cloning of a nucleotide sequence of the invention, and/or for the expression of the polypeptide encoded by this sequence, and characterized in that it contains a recombinant nucleic acid as defined above in one of its sites which is not essential for its replication.

As an example of an abovementioned vector, plasmids, cosmids, phages or viruses may be mentioned.

As such, the invention relates more especially to the plasmid pK 1.2. deposited at the CNCM under the No. I-1573.

The subject of the invention is also a method for preparing a polypeptide of the invention, by transformation of a cell host using a recombinant vector of the abovementioned type, followed by the culturing of the cell host thus transformed and the recovery of the polypeptide in the culture medium.

Thus, the invention relates to any cell host transformed by a recombinant vector as defined above, and comprising the regulatory elements permitting the expression of the nucleotide sequence coding for a polypeptide according to the invention.

The invention likewise covers DNA (or RNA) primers which can be used in the context of the synthesis of nucleotide and/or polypeptide sequences of the invention, by the PCR (polymerase chain reaction) technique or any other method known at the present time for amplifying nucleic acids, such as LCR, CPR, ERA, SPA, NASBA, and the like.

The invention relates to any DNA or RNA primer, characterized in that it consists of approximately 10 to 25 nucleotides which are identical or complementary to the first 10 to 25 nucleotides of the nucleotide sequence coding for a peptide sequence according to the invention, or identical to the last 10 to 25 nucleotides of the said sequence.

Thus, the present invention also covers a method for preparing a polypeptide of the invention comprising the following steps:
where appropriate, the prior amplification by standard techniques of the amount of nucleotide sequences coding for the said polypeptide using two suitably chosen DNA primers,
the culturing, in a suitable culture medium, of a cell host previously transformed by a vector containing a nucleic acid according to the invention comprising the nucleotide sequence coding for the said polypeptide, and
the recovery from the abovementioned culture medium of the polypeptide produced by the said transformed cell host.

By way of example of DNA or RNA primers according to the invention, the following pairs of sequences may be mentioned:

S1: GTGATGAACTTTTTAATGAATTATTAAA
(SEQ ID No. 6)

S2: TGTTGTTCTTGTTGAACACTTTTTACTAA
(SEQ ID No. 7)

whose respective positions on the LSA-3/K1 gene depicts [sic] in FIG. 1 are from 695 to 722 and from 829 to 799 (reading in the reverse direction), or the pair:

6.1: GGTATCGAAACTGAGGAAATAAAGG (SEQ ID No. 8)

6.2: CATAGCAGGAACATCAACATCCAC (SEQ ID No. 9)

whose respective positions are 2668 to 2692 for 6.1 and 3456 to 3433 for 6.2 (reading in the reverse direction).

The information regarding the sequences ID No. 6, ID No. 7, ID No. 8 and ID No. 9 are detailed at the end of the description.

The peptides of the invention may also be prepared by the standard techniques of peptide synthesis. This synthesis may be carried out in homogeneous solution or in the solid phase. For example, use may be made of the technique of synthesis in homogeneous solution described by Houben-Weyl in the work entitled "Methoden der Organischen Chemie" (Methods in Organic Chemistry) edited by E. Wunsch, vol. 15-I and II. Thieme, Stuttgart 1974, or that described by R. D. Merrifield in the paper entitled "Solid phase peptide synthesis" (J. Am. Chem. Soc., 45, 2149–2154).

The invention also covers the water-soluble oligomers of the abovementioned monomeric peptides.

Oligomerization can cause an enhancement of the immunogenicity of the monomeric peptides according to the invention. While such numerical information cannot be regarded as limiting, it may nevertheless be mentioned that these oligomers can, for example, contain from 2 to 10 monomer units.

To carry out the oligomerization, use may be made of any polymerization technique commonly used in the peptide field, this polymerization being conducted until an oligomer or polymer containing the requisite number of monomer motifs for acquiring the desired immunogenicity is obtained.

One method of oligomerization or polymerization of the monomer consists in reacting the latter with a crosslinking agent such as glutaraldehyde.

Use may also be made of other oligomerization or coupling methods, for example the one employing successive couplings of monomer units via their carboxy- and amino-terminal functions in the presence of homo- or heterobifunctional coupling agents.

The invention also relates to the conjugates obtained by covalent coupling of the peptides according to the invention (or of the abovementioned oligomers) to physiologically acceptable and non-toxic (natural or synthetic) carrier molecules that enable, in particular, the immunogenicity to be augumented via complementary reactive groups carried, respectively, by the carrier molecule and the peptide. By way of example of macromolecular carrier molecules or supports which participate in the constitution of the conjugates according to the invention, there may be mentioned natural proteins such as tetanus toxoid, ovalbumin, serum albumins, haemocyanins, tuberculin PPD (PPD: purified protein derivative), and the like.

By way of synthetic macromolecular supports, may be mentioned, for example, polylysines or poly(DL-alanine)-poly(L-lysine)s.

By way of hydrocarbon or lipid supports, there may be mentioned saturated or unsaturated fatty acids, and preferably $C_{16}$ or $C_{18}$ acids of the oleyl or palmitoleyl type.

Lastly and without implied limitation, the antigens or peptides according to the invention may be coupled to traditional supports or adsorbed on such supports, in particular latex or polystyrene microspheres or beads, or incorporated in Ty1 particles.

To synthesize the conjugates according to the invention, use may be made of methods which are known per se, such as the one described by Frantz and Robertson in Infect. and Immunity, 33, 193–198 (1981), or the one described in Applied and Environmental Microbiology (October 1981), vol. 42, No. 4, 611–614 by P. E. Kauffman, using the peptide and the appropriate carrier molecule.

The nucleic acids of the invention may be prepared either by a chemical method or by other methods.

A suitable method of preparing the nucleic acids of the invention containing not more than 200 nucleotides (or 200 bp in the case of double-stranded nucleic acids) comprises the following steps:

DNA synthesis using the automated β-cyanoethyl-phosphoramidite method described in Bioorganic Chemistry 4; 274–325 (1986), cloning of the nucleic acids thereby obtained into a suitable vector and recovery of the nucleic acid by hybridization with a suitable probe.

A chemical method of preparation of nucleic acids of length greater than 200 nucleotides has already been described in WO 92/13884.

The invention also relates to diagnostic kits which contain one or more amplification primers specific for the LSA-3 gene and which enable the presence of the gene or of the mRNA to be detected in an individual likely to be infected by *P.falciparum*.

The invention also covers pharmaceutical or vaccine compositions in which at least one of the products according to the invention is present in combination with solid or liquid, pharmaceutically acceptable excipients suitable for the construction of oral, ocular or nasal dosage forms, or excipients suitable for the construction of dosage forms for rectal administration, or alternatively with gelatinous excipients for vaginal administration. It also relates to isotonic liquid compositions containing at least one of the conjugates according to the invention, suitable for administration to the mucosae, in particular the ocular or nasal or pulmonary mucosae.

Advantageously, the vaccine compositions according to the invention contain, in addition, a vehicle such as polyvinylpyrrolidone which facilitates the administration of the vaccine. In place of polyvinylpyrrolidone, it is possible to use any other type of adjuvant, in the traditional sense which was formerly given to this expression, that is to say a substance which enables a medicinal product to be absorbed more readily or which facilitates its action in the body. By way of examples of other adjuvants of this latter type, there may also be mentioned carboxymethylcellulose, aluminium hydroxides and phosphates, saponin or all other adjuvants of this type which are well known to a person skilled in the art. Lastly, they contain, if necessary, an immunological adjuvant, in particular of the muramyl peptide type.

The invention also relates to pharmaceutical compositions containing as active substance at least one of the polyclonal or monoclonal antibodies defined above, in combination with a pharmaceutically acceptable vehicle.

Lastly, the invention covers a method of immunization of an individual likely to be infected by *P.falciparum* , by injection of a peptide molecule or an oligomer as described above, alone or in combination with other types of molecules capable of protecting the said individual against subsequent infection; the polypeptide or antigenic molecule or the natural or recombinant lipopeptides are either used alone or adsorbed or coupled to latex or polystyrene microspheres or beads.

Additional features of the invention will also become apparent in the examples illustrated with the figures which follow, and show the special features of the molecules of the invention relative to other antigens of the pre-erythrocytic stage of the parasite.

FIG. 1 depicts the genomic DNA sequence ID No. 1 of 6152 base pairs of the LSA-3 gene; it originates from the clone K1.2, which itself originates from a Thai isolate.

FIG. 2 depicts the cDNA sequence ID No. 2 and the polypeptide sequence of the LSA-3 antigen. The DNA sequence represents 5361 base pairs.

FIG. 3 depicts the sequence ID No. 4 of the portion sequenced in the parasite clone T9/96 (1890 base pairs), the upper line being the nucleotide sequence and the lower line the peptide sequence. In this clone, the CT1 sequence lies between nucleotides 67 and 126, the actual fragment DG679 beginning at nucleotide 207. The fragment 729RE lies between nucleotides 547 and 629.

Figure 4A:
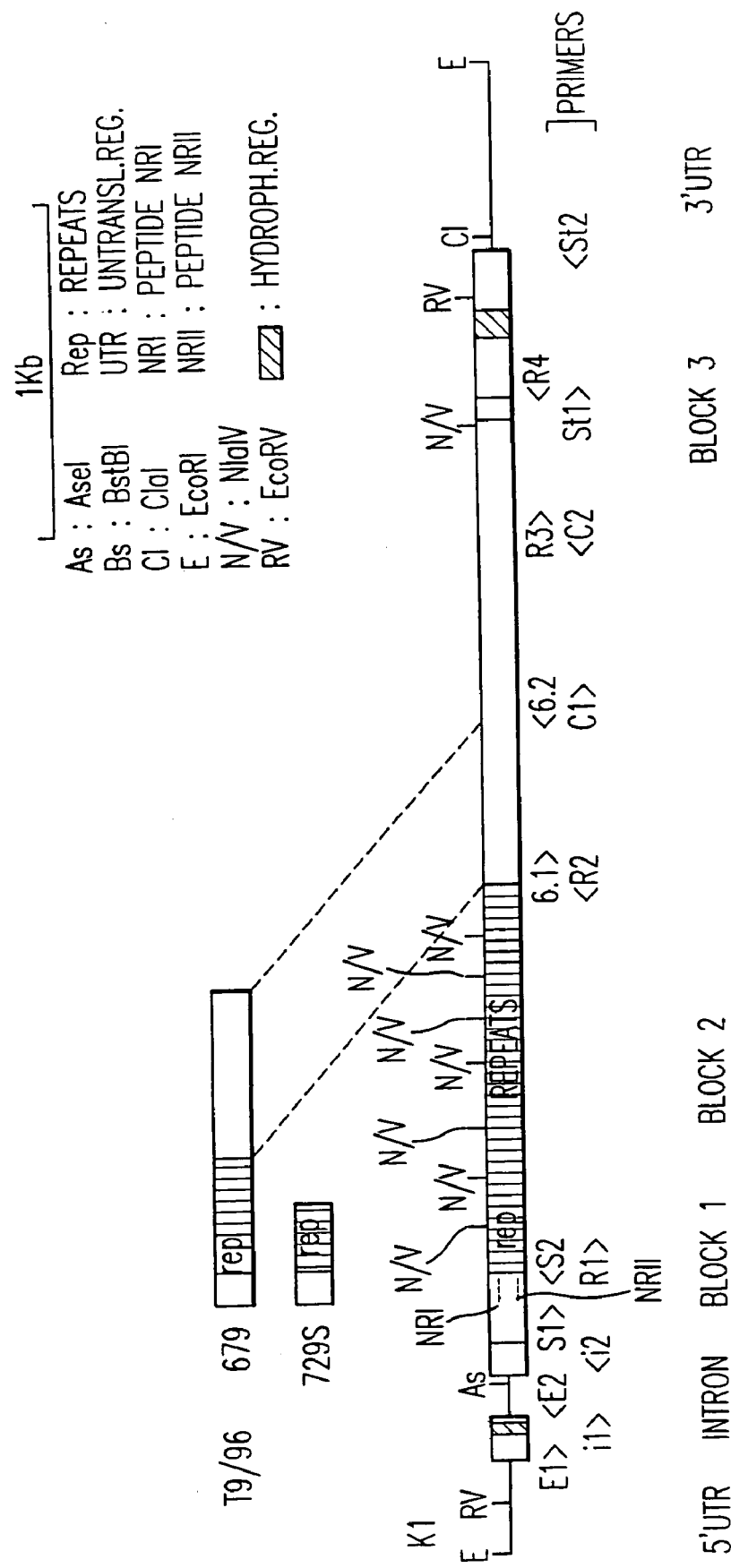

FIG. 4*a* depicts diagrammatically the relative positions of the repeat and non-repeat sequences, the introns and the exons in strains K1 and T9/96, the clones 679 and 729 originating from the latter.

Figure 4B:
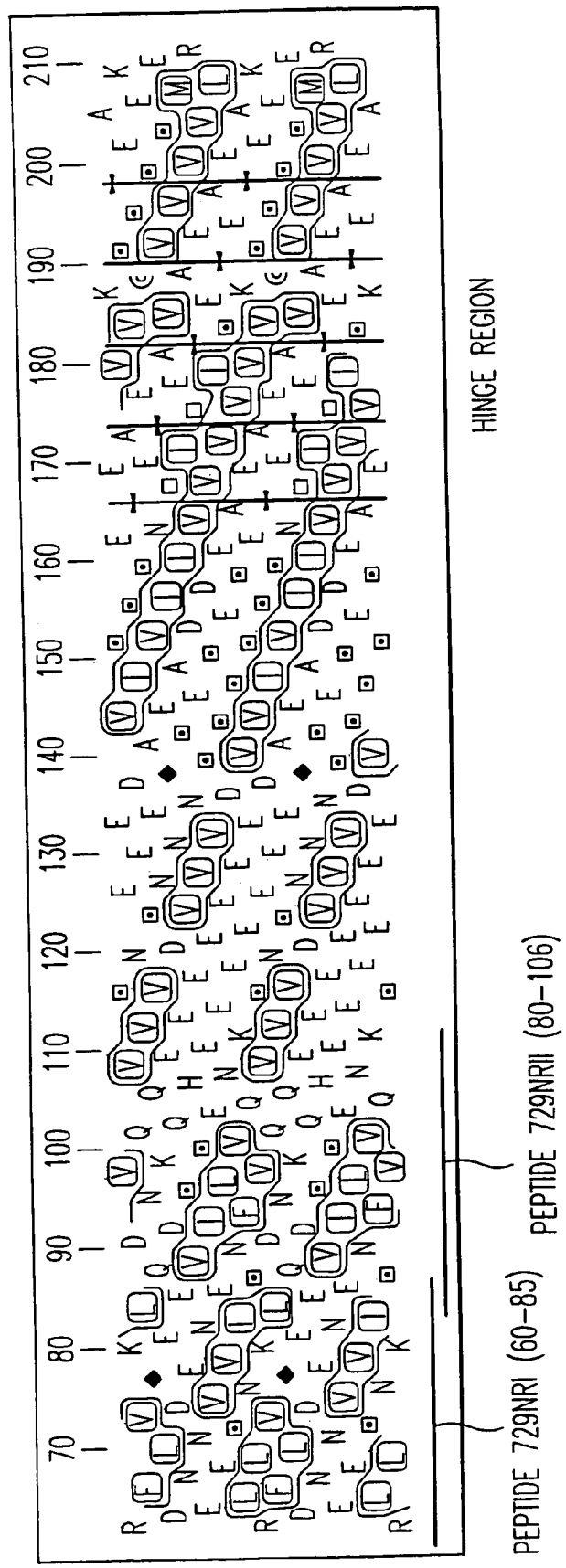

FIG. 4b depicts the HCP (hydrophobic cluster plot) of the peptide sequence of the clone DG729.

Figure 5:
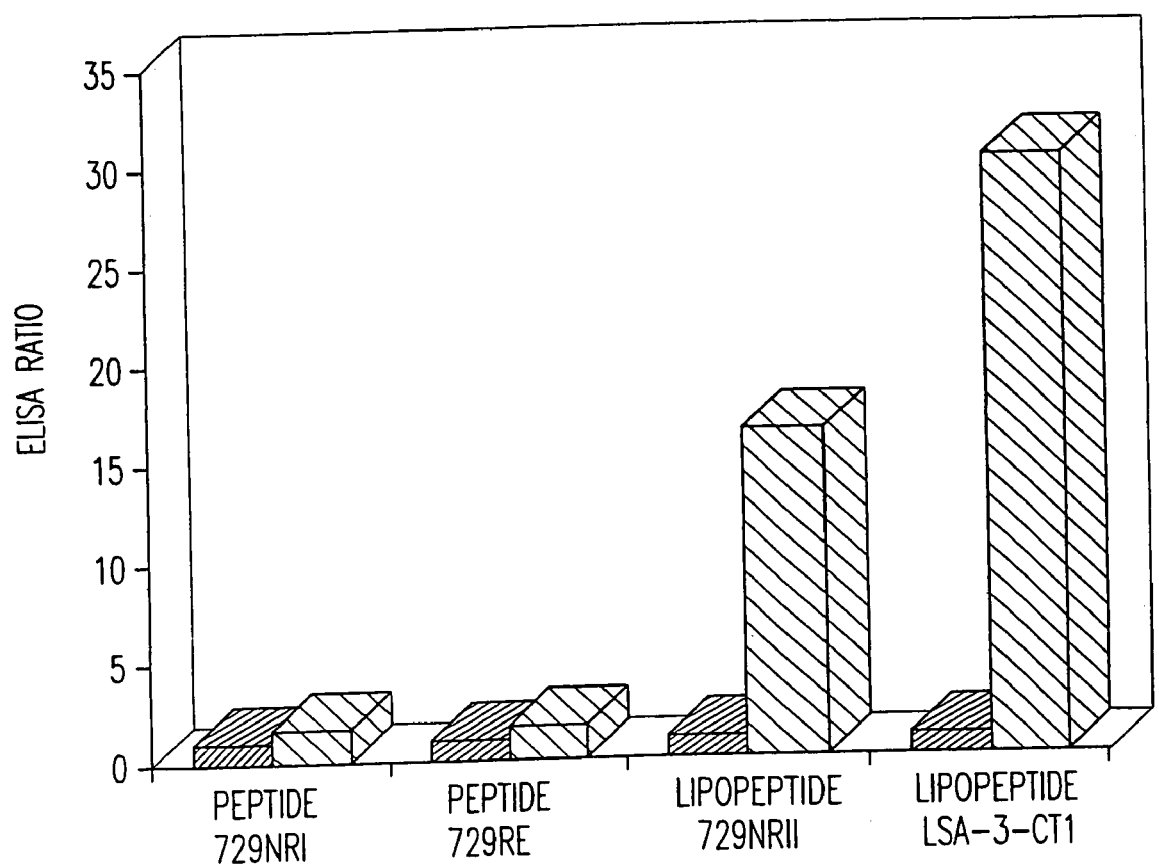

FIG. 5 depicts the amounts of immunoglobulins produced in the serum of chimpanzee Nuria before and after immunization with different LSA-3 peptides.

Figure 6:
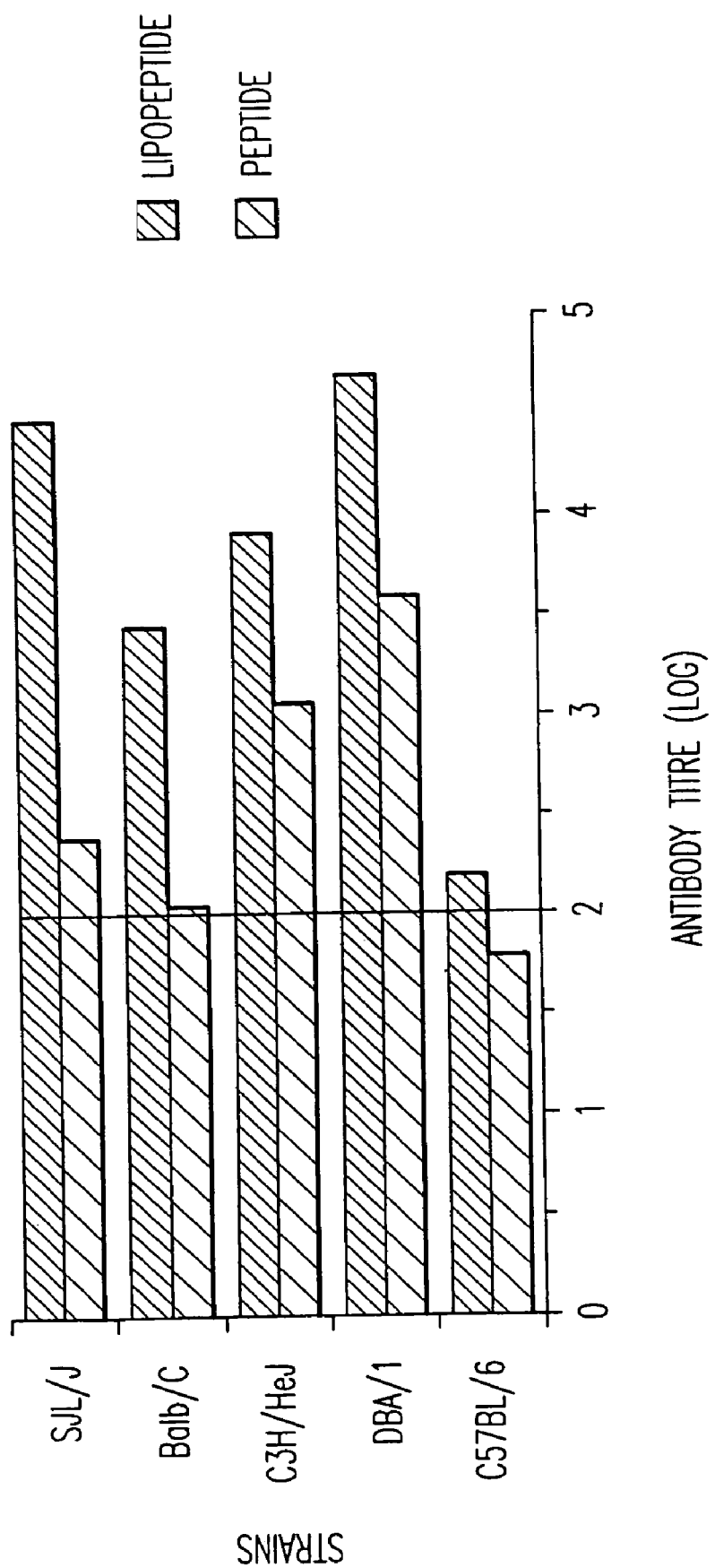

FIG. 6 shows the specific antibody titre of different species of mice immunized either with a peptide or with a corresponding lipopeptide.

Figure 7:
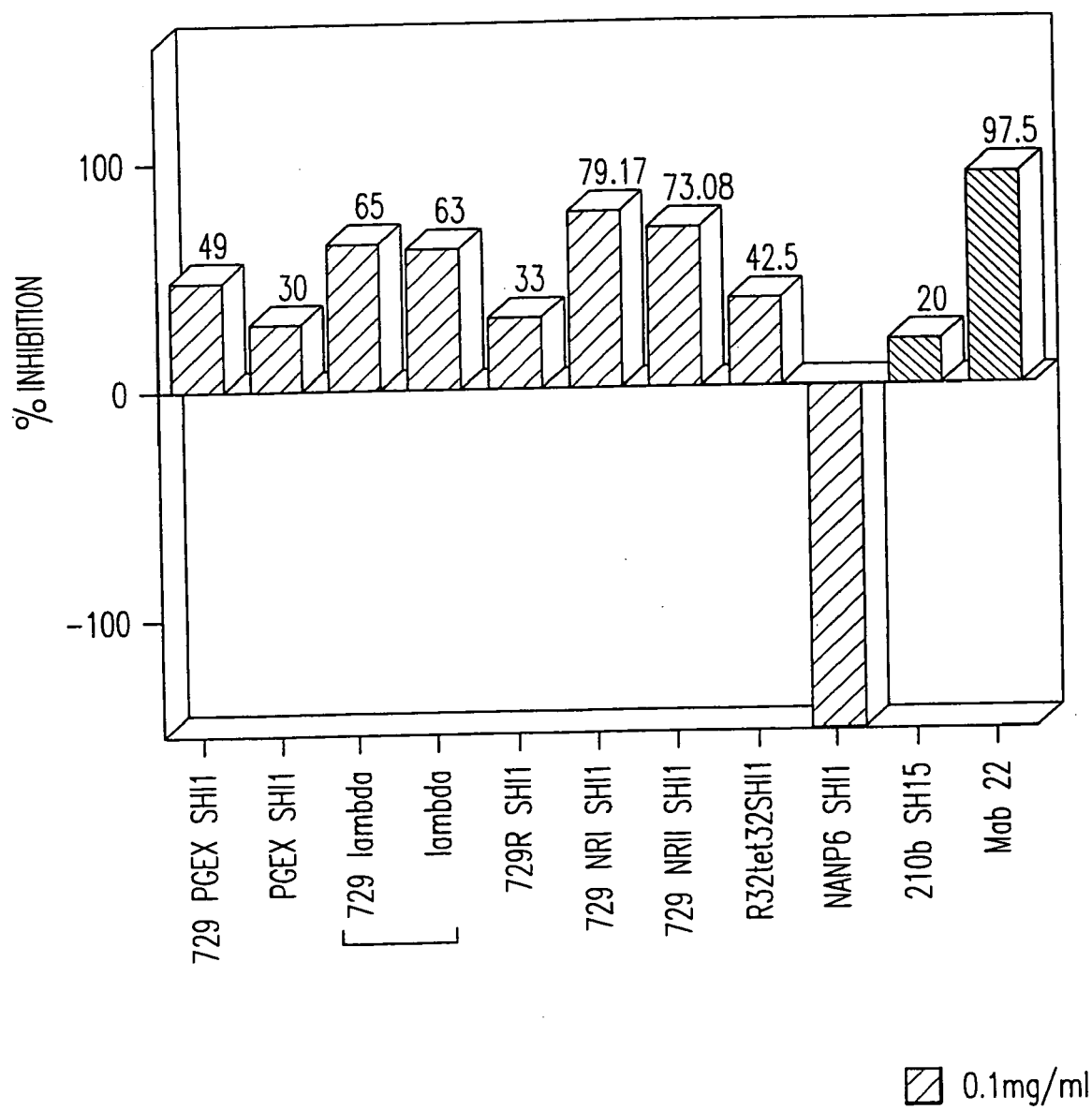

FIG. 7 shows the inhibition of the sporozoite invasion of liver cells by hyperimmune sera obtained after immunization with different peptides [lacuna] immunopurified against whole LSA-3.

Figure 8:
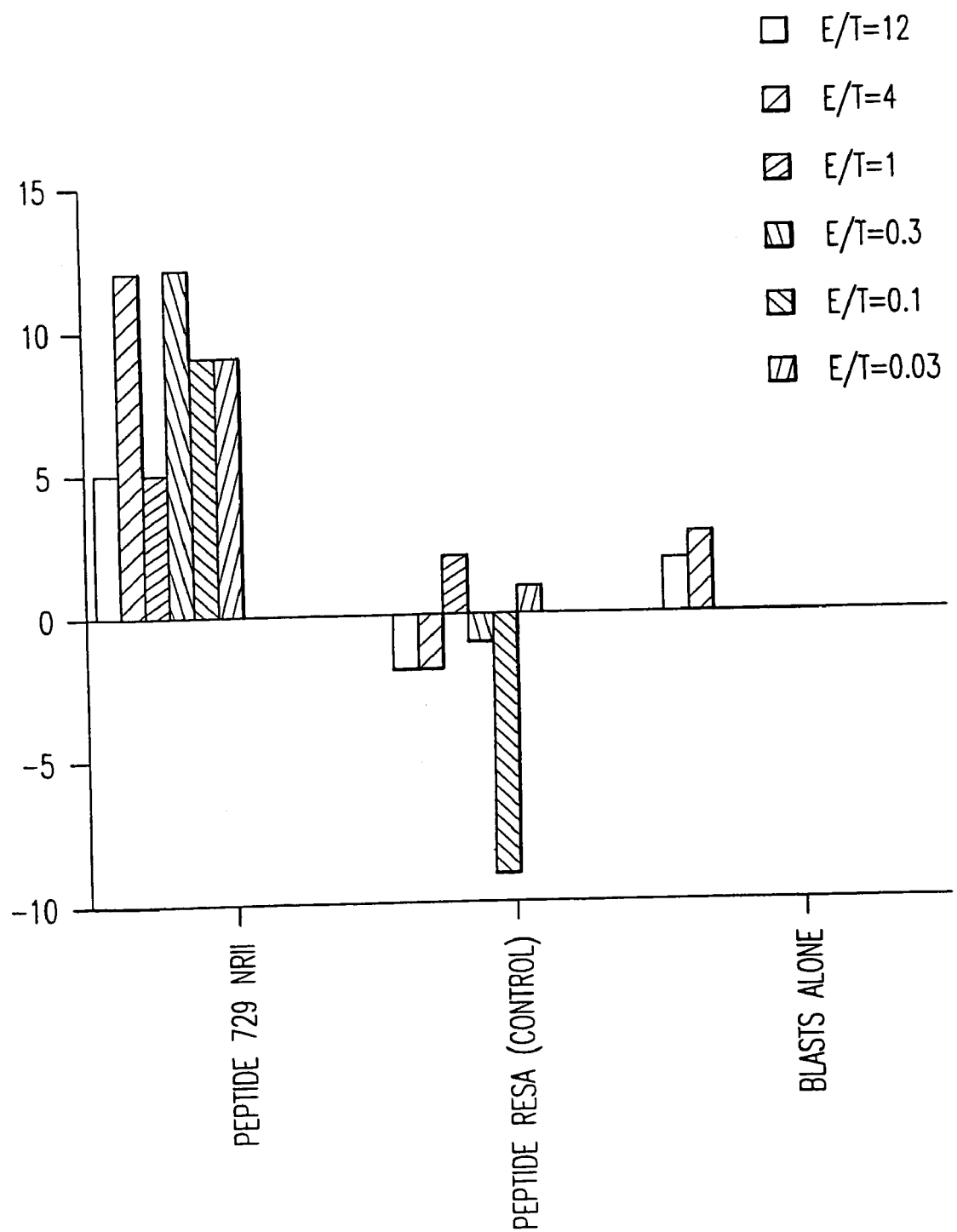

FIG. 8 depicts the comparison of an antigen originating from LSA-3 with two other antigens with respect to type T immunity.

Figure 9A:
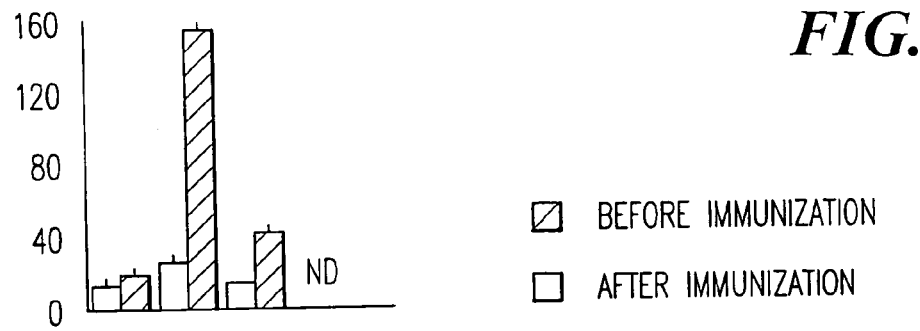
Figure 9B:
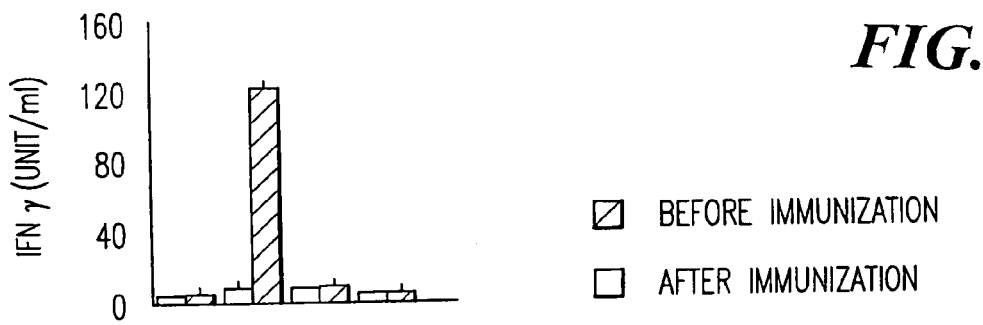
Figure 9C:
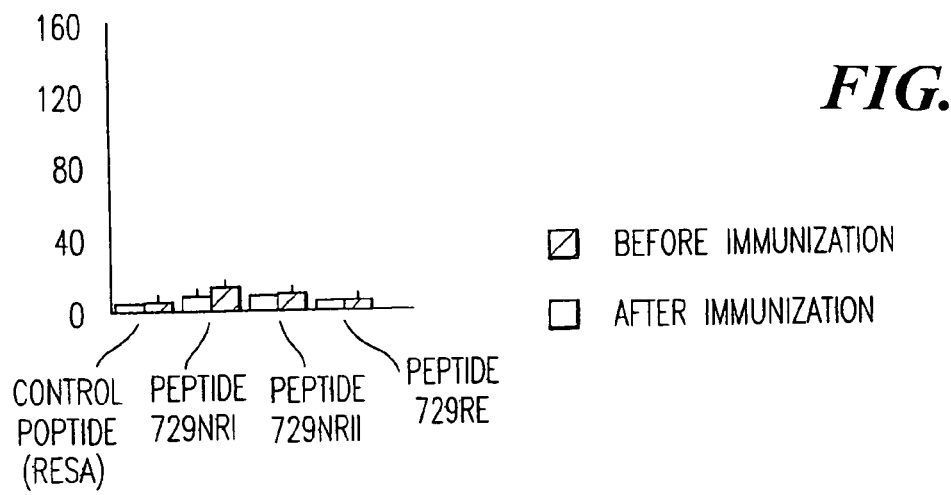

FIGS. 9A–9C depicts the induction of interferon-γ in the chimpanzees Gerda and Dirk with the peptides originating from the LSA-3 molecule.

Figure 10B:
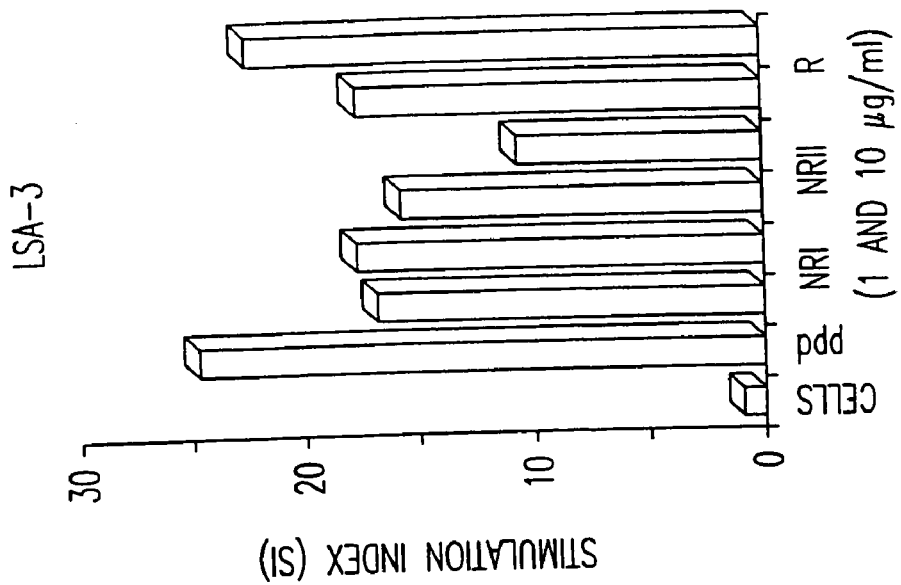
Figure 10A:
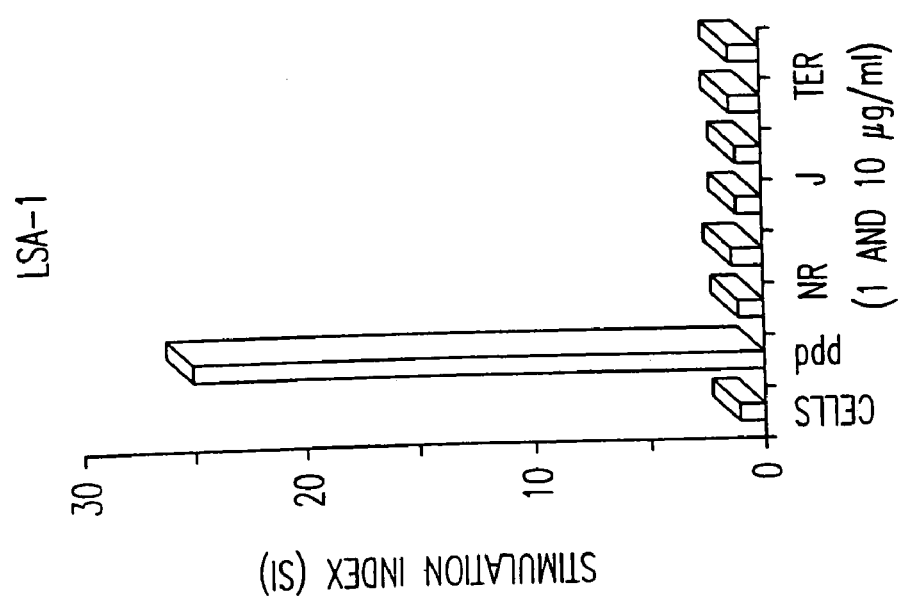

FIGS. 10A–10B depicts the results of lymphoproliferation of the PBMC of an individual protected by an injection of irradiated sporozoites against peptides originating from the LSA-1 and LSA-3 antigens.

EXAMPLE 1

Cloning and Sequencing of the LSA-3 Gene

1) Sequencing

Initial screening of the gene library originating from the parasite clone T9/96 with the serum of a missionary treated continuously by prophylaxis enabled us to isolate 120 clones corresponding to molecules expressed at the sporozoite and/or liver stage of the *P.falciparum* cycle. The clone 729S was used as probe to screen a genomic library of the Thai strain K1 already mentioned above, which contains large EcoR I fragments cloned into phage lambda gt10. A 6.85-kilobase insert containing the whole gene was purified from this gene library and recloned into a pUC18 plasmid for sequencing and characterization. In *P.falciparum*, the genome of which is very rich in bases A:T(80%), this approach is often rendered difficult by the rarity of restriction sites which can be used, and by the instability or even the impossibility of cloning certain fragments when they are inserted into plasmid vectors.

The structure of the gene is depicted in FIG. 4 and displays the following features:

a) a mini-exon 1 coding at its 3' end for a hydrophobic signal peptide;
b) a short intron (168 basepairs) included between consensus splicing do not and acceptor sites;
c) a second exon of five kilobases which codes for an organized region of 1.8 kilobases, and composed of an arrangement of 7 blocks of 4 amino acids and a 3' hydrophobic region which might correspond to a linking of the glycosylphosphatidylinositol (GPI) type.

A detailed investigation of the polymorphism of LSA-3 was carried out by sequencing the clone 679, which contains the bulk of the repcat sequences of the LSA-3 gene and a 1-kilobase portion of the 3' non-repeat fraction, the sequence of this fragment being depicted in FIG. 3 between nucleotides 207 and 1890.

The strain K1 repeats are the following:

```
Block 1:                                                      [SEQ ID NO:21]
(aa223)  VEEK VEES VEEN DEES VEEN VEEN VEEN                   (aa278)

DDGS VASS VEES IASS VDES IDSS IEEN

Block 2:                                                      [SEQ ID NO:22]
(aa279)  VAPT VEEIVAPS VVESVAPS VEESVEEN                      (aa818)

VEESVAEN VEESVAEN VEESVAEN VEESVAEN

VEEIVAPT VEEIVAPT VEEIVAPS VVESVAPS VEESVEEN

VEESVAEN VEESVAEN VEESVAEN VEESVAEN VEESVAEN

VEEIVAPT VEEIVAPT VEEIVAPS VVESVAPS VEESVEEN

VEESVAEN VEESVAEN VEESVAEN VEESVAEN VEESVAEN

VEESVAEN VEESVAEN

VEEIVAPT VEEIVAPT VEEIVAPS VVESVAPS VEESVEEN

VEESVAEN VEESVAEN VEESVAEN VEESVAEN

VEEIVAPT VEEIVAPT VEEIVAPS VVESVAPS VEESVEEN

VEESVAEN VEESVAEN VEESVAEN

VEEIVAPT VEEIVAPT VEEIVAPS VVESVAPS VEESVEEN

VEESVAEN VEESVAEN VEESVAEN VEESVAEN

VEEIVAPT VEEIVAPT VEEIVAPS VVESVAPS VEESVEEN

VEESVAEN VEESVAEN VEESVAEN

VEESVAPT VEEIVAPS VEESVAPS VEESVAEN
```

-continued

```
Block 3:                                              [SEQ ID NO:23]
(aa1537)DEDI EEDV EEDI EEDI EEDK VEDI DEDI DEDI GEDK DEVI (aa1576)
```

The repeats in the clone T9/96 as determined in Patent Application No. FR 91/01286 of Feb. 5, 1991 are the following:

```
Block 1:                          [SEQ ID NO:24]
VEEK VEES VEEN DEES VEEN VEEN
VEEN DDGS VASS

VEES IASS VDES IDSS IEEN

Block 2:                          [SEQ ID NO:25]
VAPT VEEIVAPT VEEIVAPS VVES-
VAPS VEESVAPS

VEESVAEN VEESVAEN

VEEIVAPS

VEESVAEN VEESVAEN VEESVAEN
VEESVAEN VEESVAEN

VEEIVAPT VEESVAPT VEEIVAPT
VEESVAPT VEEIVVPS

VEESVAPS VEESVAEN VEESVAEN
VEESVAEN VEESVAEN

VEESVAEN VEBIVAPS VEEIVAPT

VEESVAEN
```

Exon 2 of the LSA-3 gene contains 2 repeat regions which can be split into 3 blocks as shown in FIG. 4:

Block 1, coding for a linked succession of 14 tetrapeptides. This block is 100% conserved with respect to amino acids and nucleic acids between T9/96 and K1. Only the tetrapeptides VEES and VEEN are to be found in block 2.

Block 2 codes, in K1, for 127 tetrapeptides corresponding to the linked succession of different octapeptides which are themselves formed by combination of 2 of the 7 basic tetrapeptides or motifs (VEES, VVES, VEEN, VEEI, VAEN, VAPS, VAPT). The number of repeats and the arrangement of these octapeptides vary according to the motifs and appear to be specific to the clone K1.2. In effect, in the clone T9/96, block 2 (53 tetrapeptides) also corresponds to the linked succession of octapeptides formed from the same 7 basic tetrapeptides (and an 8th motif VVPS which does not exist in K1), but with a different number and arrangement of these repeats.

Block 3 consists of the linked succession of 10 degenerate tetrapeptides different from those of blocks 1 and 2. This block was sequenced only in the strain K1. However, preliminary results obtained by PCR with the clone T9/96 and several other laboratory strains indicate that there is no size polymorphism in this region.

The non-repeat regions of exon 2 are especially well conserved. In effect, sequence comparison between T9/96 and K1 could be done on 315 bp at the 5' end of block 1 and on 763 bp at the 3' end of block 2. The homology is 99.4% with respect to nucleic acids and 98.6% with respect to amino acids.

Comparison of the sequences of the clone 679 originating from *P.falciparum* clone T9/96, and of the corresponding sequence of LSA-3 originating from the isolate K1, shows that the gene is well conserved, the most significant differences being observed in the repeat region where the blocks of 4 amino acids are well conserved but vary in their number and organization.

In contrast, the non-repeat 5' and 3' portions apear to be especially well conserved, showing up to 100% homology in the 5' region where B and T epitopes have already been identified.

DNA amplifications, in particular by PCR of different *P.falciparum* strains with 8 primer pairs distributed over the whole of the LSA-3 gene, showed that, except with the ones surrounding the repeat regions, the whole of the genome gives PCR products of similar size, suggesting that the LSA-3 antigen is well conserved.

Various LSA-3 probes, chosen in the repeat and non-repeat regions, were hybridized at low stringency with the DNAs of different species of Plasmodium, and did not enable any gene homologous to LSA-3 to be identified except in the chimpanzee parasite *P.reichenowi,* confirming the close kinship of this species with *P.falciparum.*

Surprisingly, the antigen analogous to LSA-3 found in *P.yoelii* , which gives clear immunological cross-reactions at the surface of the sporozoite with antibodies against the fragment 729S, does not appear to be conserved at the level of the nucleotide sequence. Lastly, comparison of the LSA-3 sequences with the data bases did not reveal any homology with known molecules, except for the repeat region, some of the motifs of which display a strong analogy with the repeats of a Staphylococcus xylosis gene, but also with two *P.falciparum* antigens, RESA and Pf11.1, which are both expressed during the blood stage of the parasite. This homology is essentially due to the large amount of "Glu-Glu" sequences in these antigens and in the repeats of LSA-3.

2) Cloning

The insert DG729 and other regions of exon 2 of the strain K1 were cloned into a prokaryotic expression vector pGEX, a vector marketed by the company InVitrogen Corp (San Diego USA). This vector produces a fusion protein with the *Schistosoma mansoni* glutathione S-transferase (GST), and enables the recombinant proteins to be purified readily by affinity for glutathione-agarose beads. The expression peptides from these vectors are designated:

for the whole LSA-3 protein: REC protein, or for the fragment 729S:729PGEX.

Attempts at cloning other fragments, in particular the fragment 1–3NSREP, 3NFREP, 5NR and 5SNREP, caused difficulties related either to the cloning or to the production and purification of the proteins in sufficient amounts for immunization experiments.

Only the fragments 729, NN and 3PC enabled corresponding recombinant polypeptides to be produced and purified in sufficient amounts for analysis of the antigenicity of the molecule.

EXAMPLE 2

Protection of Immunized Chimpanzees Against Challenge Injections at Low or High Dose 2.1. A chimpanzee Dirk previously immunized with a fraction of LSA-3 in combination with another antigen of the same stage of development of the parasite, and displaying the effects described above in point a), was reimmunized a few years later with peptides and recombinant proteins corresponding to the same combination of antigens. Once again, this chimpanzee proves to be protected against a challenge infection at low dose ($2\times10^4$ sporozoites) and then a challenge infection at high dose ($5\times10^6$ sporozoites). As during the first challenge, a substantial reduction is observed in the number of schizonts detected in the liver after the challenge at high dose, as well as a lymphocytic-monocytic infiltrate around the few schizonts that are detectable (testifying to a local defence).

2.2 Partial protection of the chimpanzee Gerda: another chimpanzee was immunized only with the LSA-3 antigen (animal described in Examples 7 and 8 below), namely the lipopeptide NR2 and then recombinant proteins (GST-729, GST-NN, GST-3PC) which, the three of them collectively, cover 95% of the LSA-3 molecule and which are adsorbed on latex microspheres. This animal proves to be partially protected against a challenge infection at high dose ($8\times10^6$ sporozoites), since it displays a very low blood parasitaemia and a 90% reduction in the number of liver schizonts relative to the control following the challenge infection.

2.3. Partial protection of the chimpanzee Nuria: a chimpanzee immunized with a fraction of the LSA-3 antigen alone, namely a combination of peptides, of lipopeptides and then of recombinant proteins corresponding to 95% of the LSA-3 molecule and emulsified in Montanide ISA-51 (SEPPIC, 75 Quai d'Orsay, France), proves to be partially protected against a challenge infection at moderate dose ($1\times10^5$ sporozoites). In effect, this animal displays a significant delay in the appearance of the parasites in the blood relative to 4 controls (chimpanzees immunized with the pre-erythrocytic antigens LSA-1, SALSA or STARP, and 1 unimmunized control animal), a lower maximum blood parasitaemia and a faster fall in parasitaemia (24 hours instead of 3 days), which results reflect a large reduction in the number of liver forms induced in this animal by the challenge infection and in agreement with the results obtained in Gerda. In this case, examination of the liver forms was not carried out.

2.4. B and T immunogenicity in the chimpanzees Demi, Karlien and Iris: three chimpanzees immunized with the peptides LSA-3-NR1 and -RE and the lipopeptides -NR2 and -CT1, as well as with peptides corresponding, for each animal, to another pre-erythrocytic antigen (LSA-1, SALSA or STARP), display, all 3 of them:

high humoral responses against the B epitopes present on the peptides NR1, NR2 and RE. The antibodies recognize not only the peptides and the recombinants but are also strongly positive on the native molecules of the parasite, which is assessed by immuno-fluorescence on the sporozoites and the liver stages of *Plasmodium falciparum* (but negative with respect to the erythrocytic stages);

high and specific lymphoproliferative responses against the 4 LSA-3 peptides, as well as the native T epitopes present at the surface of the sporozoites of *Plasmodium falciparum* and of *Plasmodium yoelii*, in which LSA-3 possesses a homologue (not yet characterized).

The B and T responses with respect to the native antigens are an important point since:

a) they prove that the synthetic molecules are indeed representative;
b) they signify that, at the time of infection, there are good prospects for obtaining an anamnestic secondary response; this is, in fact, what was observed in the chimpanzee Nuria at the time of the challenge. The importance of this observation is enhanced by the fact that the same secondary response was not obtained in respect of the other antigens such as LSA-1 and STARP.

2.5. Immunogenicity in Aotus: an owl monkey (*Aotus trivirgatus*) immunized with the 2 peptides LSA-3-NR1 and -RE and the 2 lipopeptides -NR2 and -CT1, and then restimulated with the recombinant proteins corresponding to 95% of the LSA-3 molecule and adsorbed on microspheres as described above, displays high and specific lymphoproliferative responses against the T epitopes present on these same peptides.

As regards the in vivo response of the different chimpanzees preimmunized in this way, the results underline the excellent immunogenicity (B and T) of LSA-3 in peptide, lipopeptide and recombinant form, and in all the animal models tested to date, namely 6/6 (outbred) chimpanzees and 1/1 Aotus, and in all the immunized mice (>20). It may be noted that the results of the lipopeptide formulations (which can be used in man) were obtained by subcutaneous injection in the absence of any adjuvant.

EXAMPLE 3

Identification of CTL Epitope

The method used to identify CTLs is the one described by Fidock et al., (1994), J. Immunol. 153: 190, or by Bottius et al., (1996), J. Immunol. 156: 2874–2884.

CTL (cytotoxic T lymphocyte) epitopes were identified in the peptides NR2, RE and CT1 by means of cytotoxicity tests performed on the PBMCs of the chimpanzees Dirk, Gerda, Nuria, Demi, Karlien and Iris described above.

In man, 8 additional CTL epitopes, 7 of them located in the 3' non-repeat region, could be demonstrated on the PBMCs of individuals belonging to 3 different haplotypes (MHC class I-A2, -B8 and -B53) and living in a region where the disease is endemic (Gambia) (unpublished results). Furthermore, sequencing of the 2 B53-restricted CTL epitopes demonstrated a complete conservation of their nucleotide and peptide sequences in several strains from Kenya and from Gambia.

In total, we identified 11 CTL epitopes in the LSA-3 molecule, which is considerable. Moreover, 5/6 chimpanzees developed CTL responses against the peptide NR2 after immunization with the lipopeptide NR2 without adjuvant, which is a remarkable result for non-consanguineous animals. In addition, since the antibodies developed by Nuria did not display any inhibitory activity with respect to the invasion of *Plasmodium falciparum* sporozoites, it may be surmised that the observed protection depended on cellular responses, especially on the CTLs.

EXAMPLE 4

Comparison of the Antibody Titres Before and After Immunization With Different Peptides 4.1. Comparison of the antibody responses induced by different peptides in different immunized animals.

The method used is the one described in Behr et al., (1992), J. Immunol. 149: 3321.

The reactivity is expressed as an ELISA ratio, that is to say the optical density measured at 496 nanometers of the serum after immunization referred to the optical density of the same serum before immunization. The first column shows the animal immunized, the second column the immunogen received by the animal, the 3rd column shows the number of injections carried out as well as the support accompanying the peptide injected: RP denotes recombinant protein, RP/B denotes recombinant protein adsorbed on latex beads, P denotes peptide and LP lipo-peptide. It should be pointed out, in addition, that the lipopeptides are injected in physiological saline, the peptides and the recombinant proteins are adsorbed on latex beads or in an emulsion with an adjuvant Montanide ISA-51.

TABLE I

ANTIBODY REACTIVITY OF THE DIFFERENT PEPTIDES EXPRESSED AS AN ELISA RATIO

| Chimpanzee | Immunogen | Injection No. and type | LSA-1 | | | | SALSA | | STARP | | LSA-3 | | | | R32T and 32 |
|---|---|---|---|---|---|---|---|---|---|---|---|---|---|---|---|
| | | | LSA-REP | LSA-J | LSA-NR | LSA-TER | SALSA-1 | SALSA-2 | STARP-M | STARP-R | LSA-3-CT1 | LSA-3-NR1 | LSA-3-NRII | LSA-3-REP | |
| Immunized animals | | | | | | | | | | | | | | | |
| DIRK | LSA-3 and LSA-1 | 3RP(d) | 7.4 | 9.0 | 0.9 | 0.8 | nd | nd | 0.5 | 0.7 | 1.7 | 1.0 | 1.1 | 8.8 | 0.7 |
| | | 3RP + 3(P + LP) | 20.0 | 10.0 | 0.1 | 0.4 | 0.2 | 1.1 | 1.0 | 0.6 | 1.0 | 1.1 | 3.1 | 17.0 | 0.8 |
| GERDA | LSA-3 | 3LP | nd | nd | nd | nd | nd | nd | nd | nd | nd | nd | 3.9 | nd | 0.6 |
| | | 3LP + 3RP/B | nd | nd | nd | nd | nd | nd | nd | nd | 0.7 | 1.1 | 3.0 | 12.3 | 0.9 |
| DEMI | LSA-3 and LSA-1 | 2(P + LP) | 8.0 | 14.1 | 0.7 | 16.4 | 0.6 | 1.1 | nd | nd | 0.7 | 1.5 | 11.7 | 19.1 | 0.7 |
| | | 3(P + LP) | 8.4 | 14.5 | 1.6 | 21.5 | 0.8 | 0.2 | nd | nd | 0.8 | 5.1 | 14.2 | 20.7 | 1.2 |
| | | 3(P + LP) + 3RP/B | | | | | | | | | | | | | |
| KARLIEN | LSA-3 and SALSA | 2(P + LP) | 0.5 | 1.2 | 1.0 | 1.0 | 1.1 | 2.1 | nd | nd | 1.0 | 3.6 | 3.1 | 10.3 | 0.9 |
| | | 3(P + LP) | 1.1 | 0.2 | 0.5 | 0.2 | 1.8 | 2.5 | nd | nd | 1.4 | 4.7 | 6.8 | 14.1 | 0.6 |
| | | 3(P + LP) + 3RP/B | | | | | | | | | | | | | |
| IRIS | LSA-3 and STARP | 2(P + LP) | nd | nd | nd | nd | nd | nd | 10.1 | 15.9 | 0.7 | 2.4 | 6.7 | 12.5 | 0.6 |
| | | 3(P + LP) | nd | nd | nd | nd | nd | nd | 10.5 | 16.4 | 1.3 | 3.1 | 6.8 | 15.3 | 0.5 |
| | | 3(P + LP) + 3RP/B | | | | | | | | | | | | | |
| Unimmunized controls | | | | | | | | | | | | | | | |
| COR | β-GAL | 3RP | 0.6 | 0.7 | 0.8 | 0.9 | 0.5 | 1.0 | 1.2 | 0.8 | 1.1 | 1.0 | 0.6 | 1.1 | 1.2 |
| PEER | β-GAL | 6RP | 1.1 | 0.8 | 0.7 | 0.9 | 0.8 | 1.2 | 1.0 | 0.9 | 1.1 | 0.6 | 0.9 | 0.9 | 0.3 |
| BRAM | GST | 2RP | 1.1 | 0.6 | 0.5 | 1.1 | 0.3 | 0.8 | 0.9 | 1.2 | 1.1 | 0.3 | 0.4 | 0.7 | 1.0 |
| | | 3RP | 0.8 | 0.3 | 0.8 | 1.3 | 0.7 | 1.2 | 1.1 | 1.2 | 1.6 | 0.2 | 1.3 | 0.6 | 0.4 |
| FOUAD | PBS | | 0.9 | 0.5 | 1.0 | 0.6 | 0.8 | 1.3 | 1.0 | 0.3 | 1.9 | 1.3 | 0.3 | 0.2 | 0.9 |

4.2. Titre of the antibodies obtained:

Table II shows the antibody titres of the sera obtained in the chimpanzees by immunofluorescence on the native antigens present at the surface of the different stages (sporozoite, liver and blood) of *P.falciparum*, *P.yoelii* and *P.berghei*.

TABLE II

TITRE OF IMMUNOFLOURESCENT ANTIBODIES

| | | *P. falciparum* | | | *P. yoelii* (17XL and 17XNL) | | |
|---|---|---|---|---|---|---|---|
| CHIMPANZEE | Antigen | SS (NF54) | LS (NF54 and 730 XI) | BS (150) | SS | LS | BS |
| Immunized animals | | | | | | | |
| DIRK | LSA-3 and LSA-1 | 800 | 200 | −(<100) | 200 | 200 | −(<100) |
| GERDA | LSA-3 | 400 | 200 | −(<100) | 400 | 200 | −(<100) |
| DEMI | LSA-3 and LSA-1 | 100 | 400 | −(<100) | | | |
| KARLIEN | LSA-3 and SALSA | 100 | 200 | −(<100) | | | |
| IRIS | LSA-3 and STARP | 400 | 100 | −(<100) | | | |
| Control animals | | | | | | | |
| COR | β-GAL | −(<100) | −(<100) | −(<100) | −(<100) | −(<100) | −(<100) |
| BRAM | GST | −(<100) | −(<100) | −(<100) | −(<100) | −(<100) | −(<100) |
| FOUAD | PBS | −(<100) | −(<100) | −(<100) | −(<100) | −(<100) | −(<100) |

4.3. Lymphoproliferative response of the PBMCs of the different chimpanzees after stimulation in vitro either with the different peptides or with the native antigens present at the surface of the sporozoites. This response was measured by incorporation of tritiated thymidine into PBMCs (peripheral blood cells) either after stimulation with the LSA-3 peptides (Table III) or after stimulation in vitro with sporozoites (Table IV).

The lymphoproliferative responses are shown as a counting difference in counts per minute (Δ CPM) between the number of counts obtained in the presence of antigen minus the number of counts in the absence of antigen. The figures in brackets show the stimulation indices, that is to say the ratio of the number of counts obtained in the presence of antigens to the number of counts obtained in the absence of antigens.

The results are considered to be positive when Δ CPM is greater than 1000 and when the stimulation index is greater than 3.

TABLE III

INCORPORATION OF TRITIATED THYMIDINE INTO PBMCs AFTER STIMULATION WITH THE LSA-3 PEPTIDES

| Chimpanzee | Immunogen | LSA-3-CT1 | LSA-3-NRI | LSA-3-NRII | LSA-3-REP | MSP3-C (a) | PPD (b) |
|---|---|---|---|---|---|---|---|
| Immunized animals | | | | | | | |
| DIRK | LSA-3 and LSA-1 | 94,256 (4.0) | 27,125 (8.5) | 32,455 (10.7) | 69,321 (32.3) | 796 (1.0) | 89,338 (50.3) |
| GERDA | LSA-3 | 13,359 (25.1) | 1,429 (2.8) | 13,236 (25.6) | 14,883 (28.6) | 485 (0.9) | 29,355 (132.3) |
| DEMI | LSA-3 and LSA-1 | 30,036 (46.8) | 17,221 (27.4) | 4,178 (7.3) | 52,301 (81.2) | 689 (1.1) | 167,277 (113.3) |
| KARLIEN | LSA-3 and SALSA | 30,025 (36.4) | 10,039 (12.8) | 18,365 (23.1) | 31,312 (38.0) | 575 (0.7) | 96.212 (82.3) |
| IRIS | LSA-3 and STARP | 53,312 (62.6) | 25,223 (34.8) | 6,458 (9.7) | 35,078 (47.5) | 799 (0.9) | 196,223 (62.3) |
| Unimmunized animals | | | | | | | |
| COR | β-GAL | 1,399 (0.6) | 2,599 (1.0) | 3,625 (1.3) | 786 (0.3) | 2,600 (1.1) | 19,395 (22.3) |
| PEER | β-GAL | 1,225 (0.2) | 1,369 (0.3) | 3,251 (1.2) | 2,960 (0.9) | 3,962 (1.5) | 59,399 (22.3) |
| BRAM | GST | 1,201 (0.4) | 509 (0.2) | 2,501 (0.7) | 2,659 (0.6) | 2,745 (0.7) | 39,399 (22.3) |
| FOUAD | PBS | 1,211 (1.2) | 1,310 (1.3) | 956 (0.9) | 688 (0.6) | 655 (0.5) | 136,258 (82.3) | a) Control peptide from the MSP3 antigen in the blood
b) PPD = Purified protein derivative from Mycobacterium tuberculosis

TABLE IV

INCORPORATION OF TRITIATED THYMIDINE INTO PBMCs AFTER STIMULATION VITRO WITH SPOROZOITES

| Chimpanzee | Antigen | P. falciparum sporozoites | P. yoelii sporozoites | P. berghei sporozoites |
|---|---|---|---|---|
| Immunized animals | | | | |
| DIRK | LSA-3 and LSA-1 | 10,402 (12.1) | 5,552 (5.6) | 2,110 (2.0) |
| GERDA | LSA-3 | 24,021 (20.5) | 18,228 (18.6) | 2,430 (0.7) |
| DEMI | LSA-3 and LSA-1 | 2,111 (3.2) | 935 (1.4) | 214 (0.1) |
| KARLEIN | LSA-3 and SALSA | 4,402 (6.5) | 2,228 (3.6) | 914 (2.1) |
| IRIS | LSA-3 and STARP | 9,816 (14.2) | 5,304 (8.1) | 614 (2.0) |
| Control animals | | | | |
| BRAM | GST | 245 (0.4) | 1,295 (1.6) | 514 (1.2) |
| FOUAD | PBS | 997 (1.5) | 828 (1.6) | 714 (1.1) |

4.4. Comparison of the antibody responses of chimpanzee Nuria before and after immunization with different peptides FIG. 5 depicts the amounts of immunoglobulins present in the serum of chimpanzee Nuria before and after immunization with the peptides 729NR1 and 729RE, and the lipopeptides 729NR2 and CT1.

This experiment shows the superiority as regards B immunity of the R antigen, most particularly when it is conjugated to a lipid residue.

FIG. 6 shows that the level of specific anti-bodies measured by ELISA against the peptide 729NR2 in mice immunized with either the peptide 729NRII or the lipopeptide 729NRII is markedly higher when the lipopeptide is used, irrespective of the species of mouse.

EXAMPLE 5

Lymphoproliferation of the PBMCs of an Individual Protected by Injection of Irradiated Sporozoites Against Peptides Originating From the LSA-1 and LSA-3 Antigens In eight human volunteers immunized by injection of irradiated sporozoites, anti-LSA-3 antibodies are found in each of the four individuals resistant to an infection by sporozoites; and none in the other four volunteers who developed a blood infection.

Furthermore, for the only one of these four protected individuals whose cells were accessible, the PBMCs were removed six months after the challenge infection and incubated in the presence of the peptides originating from the LSA-1 and LSA-3 antigens.

FIG. 10 depicts the results of lymphoproliferation of the PBMCs of an individual protected by injection of irradiated sporozoites against peptides originating from the LSA-1 and LSA-3 antigens.

Considerable lymphoproliferation was observed with each of the three peptides LSA-3 (NR1, NR2 and RE) but with none of the LSA-1 peptides. There was an especially high level of secretion of IFN-γ (100 IU/ml) after stimulation with the peptide NR1 and, to a lesser extent, with the peptide NR2 (IFN-γ: the cytokine having the strongest blocking effect on liver schizogony).

EXAMPLE 6

Effects of the Antibodies Against the LSA-3 Peptides on the Inhibition of the Entry of Sporozoites in Mice The techniques used to prepare the primary hepatocyte cultures, the sporozoites, the antibodies and the indirect fluorescence test are described in detail by S. Mellouk et al., Bulletin of the World Health Organization, 68: 52–59, 1990. Table V below compares the results obtained in immunofluorescence, either with antibodies against the fragment 679 or with antibodies obtained against fragments originating from other peptides. The left-hand column shows the number of schizonts detected after 48 h of culture in hepatocytes of Balb/c mice infected by P.yoelii and the right-hand column the same parameters after infection by P.berghei.

TABLE V

| Antibody clones | P.yoelii | | P.berghei | |
|---|---|---|---|---|
| | IFA | No. of LS at 48 h | IFA | No. of LS at 48 h |
| | | a) | | b) |
| Control | | 88 | 110 | 119 | 108 |
| 679 | ++ | | 0 | — | 47 |
| | ++ | | 0 | — | ND |
| 679 | ++ | 1 | | — | 105 |
| 679b | ++ | 1 | | — | 133 |
| 679c | ++ | 1 | | — | 30 |
| 32 | ++ | 8 | | ± | 103 |
| 222 | + | | 5 | ± | 26 |
| 667 | ++ | 276 | 143 | ND | 502 |
| 362 | + | 3 | | | |
| 493 | ++ | 55 | | ND | 508 |
| α P.b. CSP Mab | | | 82 | +++ | 30 |
| α P.y. CSP Mab | +++ | | 171 | | 138 |

It is clearly apparent that the antibody against the peptide 679 has an almost complete inhibitory effect on the number of what was observed at 48 h in the liver cells. Likewise, FIG. 7 shows the inhibition of the sporozoite invasion of liver cells by hyperhuman sera obtained after immunization with different peptides and immunopurified against whole LSA-3.

As regards the protection of mice, the best results were obtained by immunization with the recombinants, or antigens prepared according to the invention, adsorbed on latex or polystyrene microspheres 0.5 μm in diameter:

3/3 mice are protected against an administration with 10 times the minimum infectious dose 3/3 mice are protected against the second challenge 2/3 mice are protected against the third challenge.

The microspheres used are Polybead® polystyrene microspheres (Polysciences, Inc.) 0.50 μm in diameter (ref. 07307) on which the recombinants or the peptides are adsorbed passively. In practice, in mice, per injection, 50 μg of antigens are brought into contact with 50 μl of microbeads; the exact amount of antigens adsorbed is not determined. In chimpanzees, the same procedure is performed with 200 μg of antigens and 200 μl of beads.

Furthermore, recently, the immunization of mice with the recombinant GST-3PC (corresponding to the non-repeat 3' region from amino acid No. 869 to the stop codon at the 3' end) has enabled sera to be obtained which react very strongly in immunofluorescence with *Plasmodium falciparum* sporozoites. This result is the first demonstration of the presence of one or several B epitopes in this region of the molecule.

EXAMPLE 7

Cytotoxicity Test Against the Peptide 729NRII in the Chimpanzee Gerda

The chimpanzee Gerda was immunized via the i.v. route with the lipopeptide 729NRII originating from the LSA-3 antigen. Blood is drawn 9 days after the 4th injection. The PBMCs were incubated in vitro with 5 μg/ml of the peptide 729NRII (addition of recombinant IL-2, 10 U/ml, on day 3). On day 15, the cytotoxic activity was studied against autologous blasts generated with PHA at a concentration of 0.5 μg/ml. The blasts were preincubated overnight with 5 μg/ml of the peptide 729NRII, and with a control peptide, namely RESA, or without a peptide. The peptides are not added during the test (8 hours). The number of targets per well is 5000.

PBMCs from Gerda incubated for the same period with 5 μg/ml of a control peptide or the peptide 729NRI (originating from the same antigen) do not bring about the lysis of autologous blasts preincubated or otherwise with the above peptides.

FIG. 8 shows the results obtained for an E/T (effector to target) ratio varying from 12 to 0.03. It is seen that the target cells presensitized with the peptide 729NRII are lysed in the presence of effector cells, indicating a cytotoxic T type immune response specific to this antigen.

The lipopeptide NRII injected via the i.v. route is capable, without adjuvant, of inducing a specific cytotoxic response.

EXAMPLE 8

Effect of the Peptide NRI on Interferon-γ Production

Interferons have been shown to have an inhibitory activity in the development of *P.falciparum* in human hepatocytes in culture (Sylvie Mellouk et al., The Journal of Immunology, vol. 139 No. 12: 41–92, 41–95, 1987). The results obtained with the peptides of the invention are as follows:

The chimpanzee Gerda, immunized with the poly-peptide NR2 and boosted with the recombinant DG729, carries PBMCs capable of secreting high levels of IFN-γ in the presence of the LSA-3 peptides, especially the peptide 729NRI. The result was confirmed in the chimpanzee Dirk, immunized with the same protein. The chimpanzee BRAM, an unimmunized control, does not show any interferon in the blood against the LSA-3 peptides.

What is claimed is:

1. An isolated polypeptide molecule comprising the amino acid sequence of SEQ ID NO: 3.

2. An isolated polypeptide molecule consisting essentially of the amino acid sequence of SEQ ID NO: 3.

* * * * *